(12) United States Patent
Jones

(10) Patent No.: US 6,951,939 B2
(45) Date of Patent: Oct. 4, 2005

(54) MULTIVALENT PLATFORM MOLECULES COMPRISING HIGH MOLECULAR WEIGHT POLYETHYLENE OXIDE

(75) Inventor: David S. Jones, San Diego, CA (US)

(73) Assignee: La Jolla Pharmaceutical Company, San Diego, CA (US)

( * ) Notice: Subject to any disclaimer, the term of this patent is extended or adjusted under 35 U.S.C. 154(b) by 116 days.

(21) Appl. No.: 09/877,387

(22) Filed: Jun. 7, 2001

(65) Prior Publication Data

US 2002/0110535 A1 Aug. 15, 2002

Related U.S. Application Data

(60) Provisional application No. 60/210,439, filed on Jun. 8, 2000.

(51) Int. Cl.$^7$ ..................... C07D 241/04; C07C 271/06
(52) U.S. Cl. ..................... 544/357; 530/402; 530/409; 560/26; 560/115; 560/158
(58) Field of Search ................................. 530/402, 409; 544/357; 560/26, 115, 158; 424/422, 423, 424, 426; 514/44; 436/518

(56) References Cited

U.S. PATENT DOCUMENTS

| | | |
|---|---|---|
| 3,225,063 A | 12/1965 | D'Alelio |
| 4,024,222 A | 5/1977 | Ts'o et al. |
| 4,179,337 A | 12/1979 | Davis et al. |
| 4,191,668 A | 3/1980 | Katz |
| 4,220,565 A | 9/1980 | Katz |
| 4,245,110 A | 1/1981 | Engelhard et al. |
| 4,261,973 A | 4/1981 | Lee et al. |
| 4,289,872 A | 9/1981 | Denkewalter et al. |
| 4,349,538 A | 9/1982 | Levy |
| 4,381,239 A | 4/1983 | Chibata et al. |
| 4,388,441 A | 6/1983 | Katz |
| 4,415,590 A | 11/1983 | Gerzon |
| 4,650,675 A | 3/1987 | Borel et al. |
| 4,670,558 A | 6/1987 | Ebel et al. |
| 4,731,373 A | 3/1988 | Barner et al. |
| 4,732,863 A | 3/1988 | Tomasi et al. |
| 4,751,181 A | 6/1988 | Keene |
| 4,766,106 A | 8/1988 | Katre et al. |
| 4,808,705 A | 2/1989 | Ferris |
| 4,820,812 A | 4/1989 | Miyoshi et al. |
| 4,863,713 A | 9/1989 | Goodwin et al. |
| 4,904,582 A | 2/1990 | Tullis |
| 4,913,812 A | 4/1990 | Moriguchi et al. |
| 4,917,888 A | 4/1990 | Katre et al. |
| 4,923,985 A | 5/1990 | Gansow et al. |
| 4,933,288 A | 6/1990 | Greenfield |
| 4,981,979 A | 1/1991 | Sivam |
| 4,987,130 A | 1/1991 | Tsushima et al. |
| 5,053,423 A | 10/1991 | Liu |
| 5,122,614 A | 6/1992 | Zalipsky |
| 5,126,131 A | 6/1992 | Dintzis et al. |
| 5,130,116 A | 7/1992 | Woo et al. |
| 5,135,737 A | 8/1992 | Keana |
| 5,162,515 A | 11/1992 | Conrad et al. |
| 5,185,433 A | 2/1993 | Dean et al. |
| 5,206,344 A | 4/1993 | Katre et al. |
| 5,229,490 A | 7/1993 | Tam |
| 5,238,940 A | 8/1993 | Liu et al. |
| 5,264,209 A | 11/1993 | Mikayama et al. |
| 5,268,454 A | 12/1993 | Barstad et al. |
| 5,274,123 A | 12/1993 | Deruelle et al. |
| 5,276,013 A | 1/1994 | Conrad et al. |
| 5,278,051 A | 1/1994 | Seeman et al. |
| 5,298,403 A | 3/1994 | Danielson et al. |
| 5,359,030 A | 10/1994 | Ekwuribe |
| 5,370,871 A | 12/1994 | Dintzis et al. |
| 5,386,020 A | 1/1995 | Seeman et al. |
| 5,391,785 A | 2/1995 | Jones et al. |

(Continued)

FOREIGN PATENT DOCUMENTS

| | | |
|---|---|---|
| AU | 744085 | 12/1998 |
| CA | 2079109 | 9/1991 |
| DE | 3 937 116 | 5/1991 |
| EP | 0 147 768 | 7/1985 |
| EP | 0 354 323 | 2/1990 |

(Continued)

OTHER PUBLICATIONS

Iverson et al. (1998). A chemically defined, toleragen–based approach for targeting anti–B2–glycoprotein I antibodies. *Lupus.* (7) Suppl. 2, S166–S169.*

Jones, D. S. et al., (2003). "Multivalent Poly(Ethylene Glycol)–Containing Conjugates for In Vivo Antibody Suppression," *Bioconjugate Chem.* 14:1067–1076.

Abaza, M–S. I. et al. (1992). "Effects of Amino Acid Substitutions Outside an Antigenic Site on Protein Binding to Monoclonal Antibodies of Predetermined Specificity Obtained by Peptide Immunization: Demonstration with Region 94–100 (Antigenic Site 3) of Myoglobin," *J. of Protein Chemistry* 11(5):433–444.

(Continued)

*Primary Examiner*—Richard L. Raymond
(74) *Attorney, Agent, or Firm*—Morrison & Foerster LLP

(57) ABSTRACT

Valency platform molecules comprising high molecular weight polyethylene oxide groups are provided, as well as conjugates thereof with biologically active molecules, and methods for their preparation. The high molecular weight polyethylene oxide group has, for example, a molecular weight of greater than 22,000 Daltons, for example at least 40,000 Daltons. In one embodiment, a composition comprising the valency platform molecules is provided, wherein the molecules have a polydispersity less than about 1.2. Conjugates of the valency platform molecule and a biologically active molecule, such as a saccharide, poly (saccharide), amino acid, poly(amino acid), nucleic acid or lipid also are provided. Also provided are pharmaceutically acceptable compositions comprising the conjugates disclosed herein and a pharmaceutically acceptable carrier, as well as methods of making and using the conjugates and compositions.

170 Claims, 20 Drawing Sheets

U.S. PATENT DOCUMENTS

| | | | |
|---|---|---|---|
| 5,447,722 A | 9/1995 | Lang et al. |
| 5,451,576 A | 9/1995 | Sessler et al. |
| 5,455,027 A | 10/1995 | Zalipsky et al. |
| 5,495,006 A | 2/1996 | Climie et al. |
| 5,506,110 A | 4/1996 | Matsuura et al. |
| 5,527,524 A | 6/1996 | Tomalia et al. |
| 5,552,391 A | 9/1996 | Coutts et al. |
| 5,567,422 A | 10/1996 | Greenwald |
| 5,606,047 A | 2/1997 | Coutts et al. |
| 5,612,460 A | 3/1997 | Zalipsky |
| 5,618,528 A | 4/1997 | Cooper et al. |
| 5,633,395 A | 5/1997 | Coutts et al. |
| 5,643,575 A | 7/1997 | Martinez et al. |
| 5,650,234 A | 7/1997 | Dolence et al. |
| 5,663,395 A | 9/1997 | Gobel et al. |
| 5,672,662 A | 9/1997 | Harris et al. |
| 5,674,911 A | 10/1997 | Emanuele et al. |
| 5,681,811 A | 10/1997 | Ekwuribe |
| 5,691,387 A | 11/1997 | Emanuele et al. |
| 5,698,664 A | 12/1997 | Allcock et al. |
| 5,700,919 A | 12/1997 | Seliger et al. |
| 5,726,329 A | 3/1998 | Jones et al. |
| 5,730,990 A | 3/1998 | Greenwald et al. |
| 5,747,244 A | 5/1998 | Sheridan et al. |
| 5,780,319 A | 7/1998 | Maxfield Wilson et al. |
| 5,786,512 A | 7/1998 | Jones et al. |
| 5,840,900 A | 11/1998 | Greenwald et al. |
| 5,844,056 A | 12/1998 | Kennedy et al. |
| 5,859,213 A | 1/1999 | Stefas et al. |
| 5,874,409 A | 2/1999 | Victoria et al. |
| 5,874,500 A | 2/1999 | Rhee et al. |
| 5,874,552 A | 2/1999 | Jones et al. |
| 5,880,131 A | 3/1999 | Greenwald et al. |
| 5,902,588 A | 5/1999 | Greenwald et al. |
| 5,919,455 A | 7/1999 | Greenwald et al. |
| 5,932,462 A | 8/1999 | Harris et al. |
| 5,965,119 A | 10/1999 | Greenwald et al. |
| 5,965,566 A | 10/1999 | Greenwald et al. |
| 5,985,263 A | 11/1999 | Lee et al. |
| 5,990,237 A | 11/1999 | Bentley et al. |
| 5,998,223 A * | 12/1999 | Matsuura et al. ............ 436/518 |
| 6,022,544 A | 2/2000 | Dintzis et al. |
| 6,048,529 A | 4/2000 | Atassi et al. |
| 6,051,648 A | 4/2000 | Rhee et al. |
| 6,060,056 A | 5/2000 | Coutts et al. |
| 6,072,040 A | 6/2000 | Dave et al. |
| 6,077,939 A | 6/2000 | Wei et al. |
| 6,106,828 A | 8/2000 | Bisgard-Frantzen et al. |
| 6,113,906 A | 9/2000 | Greenwald et al. |
| 6,127,355 A | 10/2000 | Greenwald et al. |
| 6,153,655 A | 11/2000 | Martinez et al. |
| 6,177,087 B1 | 1/2001 | Greenwald et al. |
| 6,177,414 B1 | 1/2001 | Tomalia et al. |
| 6,180,095 B1 | 1/2001 | Greenwald et al. |
| 6,207,160 B1 | 3/2001 | Victoria et al. |
| 6,214,966 B1 | 4/2001 | Harris |
| 6,251,382 B1 | 6/2001 | Greenwald et al. |
| 6,258,351 B1 | 7/2001 | Harris |
| 6,258,774 B1 | 7/2001 | Stein et al. |
| 6,284,246 B1 | 9/2001 | Weisgerber et al. |
| 6,303,569 B1 | 10/2001 | Greenwald et al. |
| 6,323,322 B1 | 11/2001 | Filpula et al. |
| 6,340,460 B1 | 1/2002 | Dintzis et al. |
| 6,362,254 B2 | 3/2002 | Harris et al. |
| 6,365,173 B1 | 4/2002 | Domb et al. |
| 6,368,612 B1 * | 4/2002 | Lanza et al. ................ 424/422 |
| 6,375,951 B1 | 4/2002 | Dintzis et al. |
| 6,376,604 B2 | 4/2002 | Kozlowski |
| 6,395,266 B1 | 5/2002 | Martinez et al. |
| 6,399,578 B1 | 6/2002 | Jack et al. |
| 6,413,507 B1 | 7/2002 | Bentley et al. |
| 6,423,685 B1 | 7/2002 | Drummond et al. |
| 6,441,136 B1 | 8/2002 | Pettit |
| 6,458,953 B1 | 10/2002 | Jones |
| 6,461,849 B1 | 10/2002 | Olsen et al. |
| 6,495,659 B2 | 12/2002 | Bentley et al. |
| 6,500,934 B1 | 12/2002 | Lerner et al. |
| 6,537,519 B2 | 3/2003 | Borel et al. |
| 6,548,644 B1 | 4/2003 | Pettit |
| 6,562,787 B1 | 5/2003 | Barney et al. |
| 6,583,267 B2 | 6/2003 | Yamasaki et al. |
| 6,602,498 B2 | 8/2003 | Shen |
| 6,656,906 B1 | 12/2003 | Barney et al. |
| 6,774,180 B2 | 8/2004 | Kozlowski et al. |
| 2001/0007755 A1 | 7/2001 | Borel et al. |
| 2001/0011115 A1 | 8/2001 | Harris et al. |
| 2001/0021763 A1 | 9/2001 | Harris |
| 2001/0027212 A1 | 10/2001 | Bentley et al. |
| 2001/0031873 A1 | 10/2001 | Greenwald et al. |
| 2001/0046481 A1 | 11/2001 | Bentley et al. |
| 2001/0051351 A1 | 12/2001 | Racis |
| 2002/0006898 A1 | 1/2002 | Greenwald et al. |
| 2002/0009426 A1 | 1/2002 | Greenwald et al. |
| 2002/0013266 A1 | 1/2002 | Bentley et al. |
| 2002/0019340 A1 | 2/2002 | Bentley et al. |
| 2002/0025321 A1 | 2/2002 | Shoenfeld et al. |
| 2002/0028912 A1 | 3/2002 | Yamasaki et al. |
| 2002/0037949 A1 | 3/2002 | Harris et al. |
| 2002/0040076 A1 | 4/2002 | Harris et al. |
| 2002/0052009 A1 | 5/2002 | Hornaver et al. |
| 2002/0052430 A1 | 5/2002 | Harris et al. |
| 2002/0052443 A1 | 5/2002 | Greenwald et al. |
| 2002/0082400 A1 | 6/2002 | Coutts et al. |
| 2002/0086819 A1 | 7/2002 | Drummond et al. |
| 2002/0086939 A1 | 7/2002 | Kozlowski |
| 2002/0107389 A1 | 8/2002 | Coutts et al. |
| 2002/0110535 A1 | 8/2002 | Jones |
| 2002/0142964 A1 | 10/2002 | Nissen et al. |
| 2002/0197261 A1 | 12/2002 | Li et al. |
| 2003/0018190 A1 | 1/2003 | Jones |
| 2003/0031674 A1 | 2/2003 | Qiu et al. |
| 2003/0032594 A1 | 2/2003 | Bonny et al. |
| 2003/0103934 A1 | 6/2003 | Sato et al. |
| 2003/0103990 A1 | 6/2003 | Coutts et al. |
| 2003/0130197 A1 | 7/2003 | Smith-Swintosky et al. |
| 2003/0139346 A1 | 7/2003 | Bentley et al. |
| 2003/0162953 A1 | 8/2003 | Coutts et al. |
| 2003/0228275 A1 | 12/2003 | Ekwuribe et al. |
| 2004/0224366 A1 | 11/2004 | Jones et al. |

FOREIGN PATENT DOCUMENTS

| | | |
|---|---|---|
| EP | 0 399 330 | 11/1990 |
| EP | 0 496 074 | 7/1992 |
| EP | 0 510 356 | 10/1992 |
| EP | 0 632 082 | 1/1995 |
| JP | 61-033195 | 2/1986 |
| JP | 62-503171 | 12/1987 |
| JP | 63-005033 | 1/1988 |
| JP | 3-5495 | 1/1991 |
| JP | 3-500530 | 2/1991 |
| JP | 4-218000 | 8/1992 |
| JP | 5-172814 | 7/1993 |
| JP | 5-504761 | 7/1993 |
| JP | 5-505520 | 8/1993 |
| WO | WO 85/03704 | 8/1985 |
| WO | WO 86/04093 | 7/1986 |
| WO | WO 87/02777 | 5/1987 |
| WO | WO 89/09628 | 10/1989 |
| WO | WO 89/12060 | 12/1989 |
| WO | WO 91/08753 | 6/1991 |
| WO | WO 91/14456 | 10/1991 |

| WO | WO 92/02531 | 2/1992 |
| WO | WO 92/11029 | 7/1992 |
| WO | WO 93/12145 | 6/1993 |
| WO | WO 94/25071 | 11/1994 |
| WO | WO 95/14231 | 5/1995 |
| WO | WO 96/04006 | 2/1996 |
| WO | WO 96/41813 | 12/1996 |
| WO | WO 97/30148 | 8/1997 |
| WO | WO 98/05363 | 2/1998 |
| WO | WO 98/32466 | 7/1998 |
| WO | WO 99/25384 | 5/1999 |
| WO | WO 00/01729 | 1/2000 |
| WO | WO 00/20019 | 1/2000 |
| WO | WO 00/66715 | 11/2000 |
| WO | WO 01/18541 | 3/2001 |
| WO | WO 01/26692 | 4/2001 |
| WO | WO 01/79449 | 10/2001 |
| WO | WO 01/88088 | 11/2001 |
| WO | WO 01/93914 | 12/2001 |
| WO | WO 02/09766 | 2/2002 |
| WO | WO 02/20033 | 3/2002 |
| WO | WO 02/26772 | 4/2002 |
| WO | WO 02/27315 | 4/2002 |
| WO | WO 02/27317 | 4/2002 |
| WO | WO 02/40058 | 5/2002 |

OTHER PUBLICATIONS

Aldrich, ed. (2003–2004) *Katalog Handbuch Feinchemikalien Und Laborgeräte* Deutschland, p. 5 (A730–A732); p. 386 (38,202–7), p. 1320 (55,441–3).

Boturyn, D. et al. (2004). "Template Assembled Cyclopeptides as Multimeric System for Integrin Tartgeting and Endocytosis," *J. Am. Chem. Soc.* 126(18):5730–5739.

Datta, B. et al. (Mar. 5, 1992). "I. Cross–Linking of U2 snRNA Using Nitrogen Mustard," *J. Biol. Chem.* 267(7):4497–4502.

Dintzis, H.M. et al. (Oct., 1976). "Molecular Determinants of Immunogenicity: The Immunon Model of Immune Response," *Proc. Natl. Acad. Sci. USA* 73(10):3671–3675.

Döring, T. et al. (1991). "The Three–Dimensional Folding of Ribosomal RNA; Localization of a Series of Intra–RNA Cross–Links in 23S RNA Induced by Treatment of *Escherichia coli* 50S Ribosomal Subunits with *bis*–(2–chloroethyl)–methylamine," *Nucleic Acids Research* 19(13):3517–3524.

European Office Action mailed Dec. 8, 2003, for European Application No. 99964209.3, filed Dec. 9, 1999, five pages.

Falbe, J. et al. eds. (1990). *Rompp Chemie Lexikon* George Thieme Verlag: Stuttgart, p. 1614, under "Glycylgycin.".

Lehninger, A.L. ed. (1975) *Biochemistry*, 2nd Edition. Worth Publishers, Inc. pp. 742–743.

Ngo, J.T. et al. (1994). "Computational Complexity, Protein Structure Prediction, and the Levinthal Paradox," Chapter 14 *In The Protein Folding Problem and Tertiary Structure Prediction*, Merz, K. Jr. and Le Grand, S. eds. pp. 433–506.

Osswald, M. et al. (1990). "Localization of a Series of RNA–Protein Cross–Link Sites in the 23S and 5S Ribosomal RNA from *Escherichia coli*, Induced by Treatment of 50S Subunits with Three Different Bifunctional Reagents," *Nucleic Acids Research* 18(23):6755–6760.

Agrawal, S. et al. (1986). "Efficient Methods for Attaching Non–Radioactive Labels to the 5' Ends of Synthetic Oligodeoxyribonucleotides," *Nucl. Acids Res.* 14(15):6227–6245.

Asseline, U. and Thuong, N.T. (1990). "New Solid–Phase for Automated Synthesis of Oligonucleotides Containing an Amino–Alkyl Linker at Their 3'–End," *Tetrahedron Letts.* 31(1):81–84.

Borel, H. and Borel, Y. (1990). "A Novel Technique to Link Either Proteins or Peptides to Gammaglobulin to Construct Tolerogens," *J. Immunol. Methods* 126:159–168.

Borel, H. et al. (1986). "A Possible New Therapy of Systemic Lupus Erythematosus (SLE)," *Ann. N.Y. Acad. Sci.* 475:296–306.

Borel, H. et al. (1984). "Conjugation of DNA Fragments to Protein Carriers by Glutaraldehyde: Immunogenicity of Oligonucleotide–Hemocyanin Conjugates," *Journal of Immunological Methods* 67:289–302.

Borel, Y. and Borel, H. (1988). "Oligonucleotide Linked to Human Gammaglobulin Specifically Diminishes Anti–DNA Antibody Formation in Cultured Lymphoid Cells from Patients with Systemic Lupus Erythematosus," *J. Clin. Invest.* 82:1901–1907.

Borel, Y. et al. (1973). "Prevention of Murine Lupus Nephritis by Carrier–Dependent Induction of Immunologic Tolerance to Denatured DNA," *Science* 182:76–78.

Brask, J. and Jensen, K.J. (2001). "Carboproteins: A 4–α–Helix Bundle Protein Model Assembled on a D–Galactopyranoside Template," *Bioorganic & Medicinal Chemistry Letters* 11:697–700.

Clark, A.J. et al. (2001). "A Nonisocyanate Route to Monodisperse Branched Polyurethanes," *J. Org. Chem.* 66:8687–8689.

Conrad, M.J. and Coutts, S. (1991). "Conjugates of Stable Polymer and Polynucleotide—Tolerogens for Human Systemic Lupus Erythematosus," Derwents Database records for European Patent No. EP 0 438 259, Jul. 191.

Dintzis, R.Z. et al. (1985). "Inhibition of Anti–DNP Antibody Formation by High Dose of DNP–Polyacrylamide Molecules; Effects of Hapten Density and Hapten Valence," *J. Immunol.* 135(1):423–427.

Dreef, C.E. et al. (1988). "Synthesis of 1–O–(1, 2–DI–O–Palmitoyl–*SN*–Glycero–3–Phospho)–D–*MYO*–Inositol 4, 5–*Bis*phosphate: An Analogue of Naturally Occuring (Ptd)Ins(4,5)$P_2$," *Tetrahedron Letts.* 29(49):6513–6516.

Eshhar, Z. et al. (1975). "Induction of Tolerance to Nucleic Acid Determinants by Administration of a Complex of Nucleoside D–Glutamic Acid and D–Lysine (D–GL)," *J. Immunol.* 144(2):872–876.

Frenkel, G.D. et al. (1987). "Inhibition of RNA and DNA Polymerases by the Product of the Reaction of Selenite with Sulfhydryl Compounds," *Mol. Pharm.* 31(1):112–116.

Gupta, K.C. et al. (Oct. 28, 1991). "A General Method for the Synthesis of 3'–Sulfhydryl and Phosphate Group Containing Oligonucleotides," *Chem. Abstracts* 115(17):976. Abstract No. 183758p.

King, T.P. et al. (1993). "Structure–Immunogenicity Relationship of Melittin and Its N–Terminal Truncated Analogs," *Biochemistry* 32(13):3506–3510.

Kremsky, J.N. et al., (1987). "Immobilization of DNA via Oligonucleotides Containing an Aldehyde or Carboxylic Acid Group at the 5' Terminus," *Nucl. Acids. Res.* 15:2891–2909.

Kuo, J. et al. (1991). "Chemical Modification of Hyaluronic Acid by Carbodiimides," *Biocongjugate Chem.* 2(4):232–241.

Leonetti, J.P. (1988). "Antiviral Activity of Conjugates Between Poly(l-lysine) and Synthetic Oligodeoxyribonucleotides," *Gene* 72:323–332.

McMurry, T.J. et al. (1992). "Convenient Sythesis of Bifunctional Tetraaza Macrocycles," *Bioconjugate Chem.* 3(2):108–117.

Mitsuo, N. et al. (1978). "Permeability of Liposomal Membranes Composed of Unnatural Types of Synthetic Lecithin–Analogues," *Chem. Pharm. Bull.* 26(5):1501–1504.

Nossal, G.J.V. (1989). "Immunologic Tolerance: Collaboration Between Antigen and Lymphokines," *Science* 245(4914):147–153.

Papalian, M. et al. (1980). "Reaction of Systemic Lupus Erythematosus Antinatve DNA Antibodies with Native DNA Fragments from 20 to 1,200 Base Pairs," *J. Clin. Invest.* 65:469–477.

Parker, L.P. et al. (1974). "Modification of NZB/NZW F Autoimmune Disease by Development of Tolerance to DNA," *J. Immunol.* 113(1):292–297.

Sasaki, T. et al. (1982). "Induction of Immunological Tolerance to Single–Stranded and Double–Stranded DNA," *Scand. J. Immunol.* 16:191–200.

Sehon, A.H. (1982). "Suppression of IgE Antibody Responses with Tolerogenic Conjugates of Allergens and Haptens," *Prog. Allergy* 32:161–202.

Stollar, B.D. and Papalian, M. (1980). "Secondary Structure in Denatured DNA is Responsible for its Reaction with Antinative DNA Antibodies of Systemic Lupus Erythematosus Sera," *J. Clin. Invest.* 66:210–219.

Usman, N. et al. (1988). "Preparation of Glyceronucleoside Phosphoramidite Synthons and Their Use in the Solid Phase Synthesis of Acyclic Oligonucleotides," *Tetrahedron Letts.* 29(38):4831–4834.

Vercruysse, K.P. et al. (1997). "Synthesis and in Vitro Degradation of New Polyvalent Hydrazide Cross–Linked Hydrogels of Hyaluronic Acid," *Biocunjugate Chem.* 8:686–694.

Verkade, P.E. et al. (1940). "Synthesen von Glyceriden mit Tritylverbindugen IV," *Recl. Trav. Pays–Bas* 59:1123–1140.

Wilkinson, I. et al. (1987). "Tolerance Induction in Mice by Conjugates of Monoclonal Immunoglobulins and Monomethoxypolyethylene Glycol," *J. Immunol.* 139:326–331.

Blank et al. (1999). "Prevention of Experimental Antiphospholipid Syndrome and Endothelial Cell Activation by Synthetic Peptides," *Proc. National Acad. Sci USA* 96:5164–5168.

Jones, D. et al. (May–Jun. 1999). "Multivalent thioether–peptide conjugates: B cell tolerance of an anti–peptide immune response" *Bioconjugate Chemistry* 10(3):480–488.

\* cited by examiner

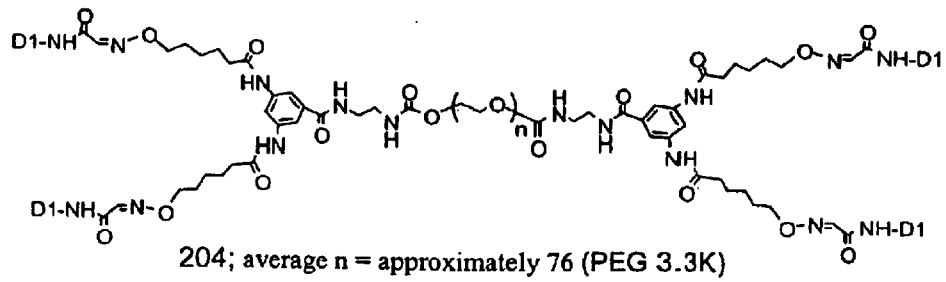
204; average n = approximately 76 (PEG 3.3K)
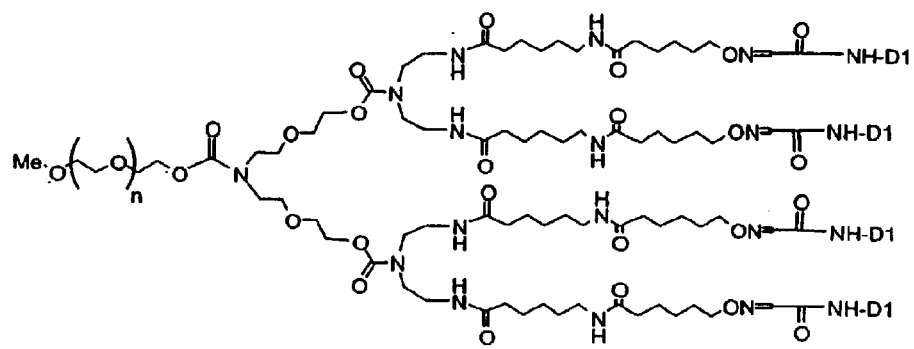
200; average n = approximately 503 (PEG 20K)
201; average n = approximately 114 (PEG 5K)
205; average n = approximately 261 (PEG 12K)
301; average n = approximately 682 (PEG 30K)
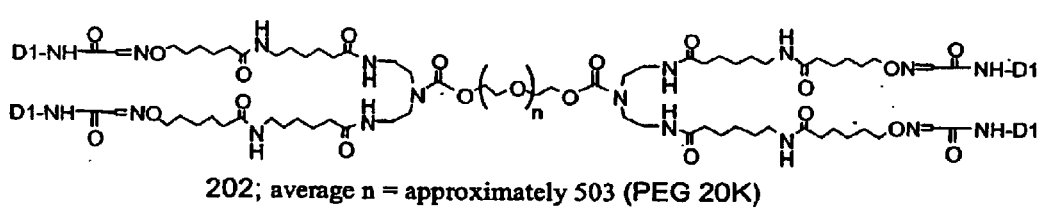
202; average n = approximately 503 (PEG 20K)
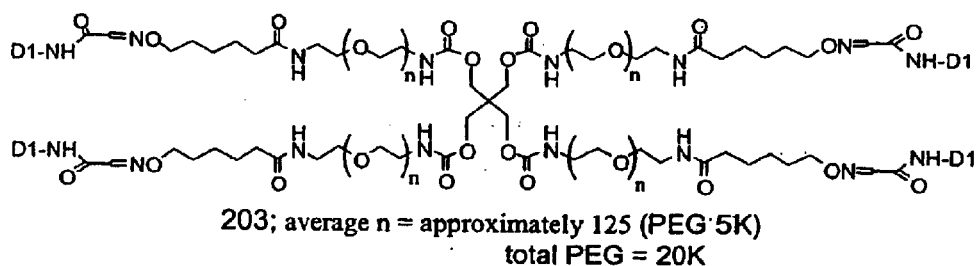
203; average n = approximately 125 (PEG 5K)
total PEG = 20K
Figure 7

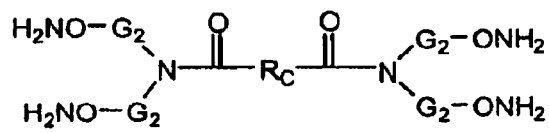
Formula 9
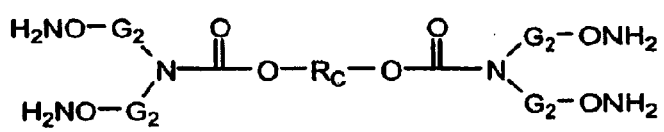
Formula 10
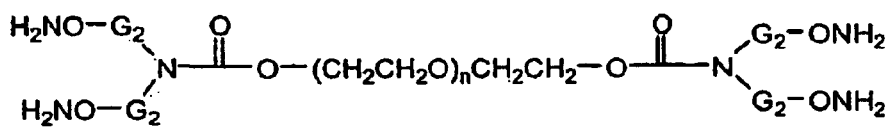
Formula 11
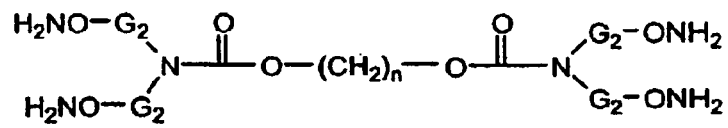
Formula 12
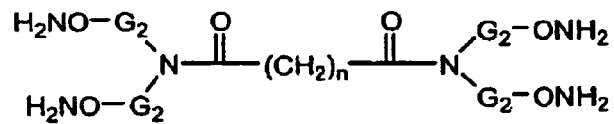
Formula 13
Figure 8

300, n = approx. 503

| | | | | | | | | | | | | | | | |
|---|---|---|---|---|---|---|---|---|---|---|---|---|---|---|---|
| gga | cgg | acc | tgt | ccc | aag | cca | gat | gat | tta | cca | ttt | tcc | aca | gtg | gtc | 48 |
| Gly | Arg | Thr | Cys | Pro | Lys | Pro | Asp | Asp | Leu | Pro | Phe | Ser | Thr | Val | Val | |
| 1 | | | | 5 | | | | | 10 | | | | | 15 | | |
| ccg | tta | aaa | aca | ttc | tat | gag | cca | gga | gaa | gag | att | acg | tat | tcc | tgc | 96 |
| Pro | Leu | Lys | Thr | Phe | Tyr | Glu | Pro | Gly | Glu | Glu | Ile | Thr | Tyr | Ser | Cys | |
| | | | 20 | | | | | 25 | | | | | 30 | | | |
| aag | ccg | ggc | tat | gtg | tcc | cga | gga | ggg | atg | aga | aag | ttt | atc | tgc | cct | 144 |
| Lys | Pro | Gly | Tyr | Val | Ser | Arg | Gly | Gly | Met | Arg | Lys | Phe | Ile | Cys | Pro | |
| | | 35 | | | | | 40 | | | | | 45 | | | | |
| ctc | aca | gga | ctg | tgg | ccc | atc | aac | act | ctg | aaa | tgt | aca | ccc | aga | gta | 192 |
| Leu | Thr | Gly | Leu | Trp | Pro | Ile | Asn | Thr | Leu | Lys | Cys | Thr | Pro | Arg | Val | |
| | 50 | | | | | 55 | | | | | 60 | | | | | |

Figure 19

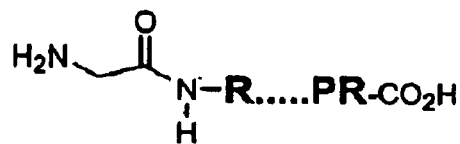
Domain 1 of β2GPI (D₁, where bold letters stand for single letter amino acid code of terminal amino acids of Domain 1 of β2GPI)
↓ pH 5.5
1-2 M NaOAc
CuSO₄
glyoxylic acid
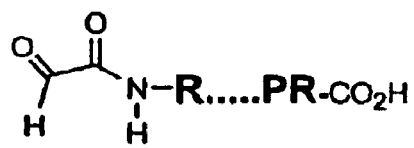
Transaminated Domain 1 (TA/D1)
Comprising a terminal glyoxyl group
Figure 20

MULTIVALENT PLATFORM MOLECULES COMPRISING HIGH MOLECULAR WEIGHT POLYETHYLENE OXIDE

CROSS REFERENCE TO RELATED APPLICATIONS

This application claims priority to U.S. Provisional Application No. Ser. No. 60/210,439, filed Jun. 8, 2000, the disclosure of which is incorporated herein by reference.

TECHNICAL FIELD

This application relates to valency platform molecules comprising polyethylene oxide groups to which one or more molecules, such as biologically active molecules, may be attached to form a conjugate.

BACKGROUND ART

A "valency platform" is a molecule with one or more (and typically multiple) attachment sites which can be used to covalently attach biologically active molecules of interest to a common scaffold. The attachment of biologically active molecules to a common scaffold provides multivalent conjugates in which multiple copies of the biologically active molecule are covalently linked to the same platform. A "defined" or "chemically defined" valency platform is a platform with defined structure, thus a defined number of attachment points and a defined valency. A defined valency platform conjugate is a conjugate with defined structure and has a defined number of attached biologically active compounds. Examples of biologically active molecules include oligonucleotides, peptides, polypeptides, proteins, antibodies, saccharides, polysaccharides, epitopes, mimotopes, drugs, and the like. For example, the biologically active compounds may interact specifically with proteinaceous receptors.

Certain classes of chemically defined valency platforms, methods for their preparation, conjugates comprising them, and methods for the preparation of such conjugates, have been described in U.S. Pat. Nos. 5,162,515; 5,391,785; 5,276,013; 5,786,512; 5,726,329; 5,268,454; 5,552,391; 5,606,047; and 5,663,395. Valency platform molecules comprising carbamate linkages are described in U.S. Pat. No. 6,458,953; and WO 00/34231. Valency platform molecules comprising aminooxy groups are described in U.S. Provisional Patent Application No. 60/138,260, filed Jun. 8, 1999; and PCT/US00/15968.

Polyethylene glycol conjugates are described, for example, in PCT WO 99/45964, published Sep. 16, 1999; U.S. Pat. Nos. 5,672,662; 5,932,462; PCT WO 99/34833; PCT WO 95/34326; and U.S. Pat. No. 5,990,237. Polyether copolymers including linear and dendritic blocks are described in Gitsov et al., *Angew Chem. Int. Ed. Engl.*, 1992, 31:1200–1203. A polyethylene glycol multiblock copolymer as a carrier of the anticancer drug doxorubicin is described in Pechar et al., *Bioconjugate Chem.*, 11:131–139 (2000). A polyethylene glycol copolymer for carrying and releasing multiple copies of peptides is described in Huang et al., *Bioconjugate Chem.* 9:612–617 (1998). Polyethylene glycol copolymers and their self assembly with DNA are described in Choi et al., *J. Am. Chem. Soc.*, 122:474–480 (2000). Polyether dendritic compounds containing folate residues are described in Kono et al., *Bioconjugate Chemistry*, 10:1115–1121 (1999).

Direct PEGylation of polypeptides is generally done by attaching to lysine amino groups or other side chain functionality. This often results in a heterogeneous mixture of products and can lead to loss of bio-activity. Thus, there is a need for improved methods of forming multivalent conjugates of biologically active molecules and polyethylene oxide groups.

DISCLOSURE OF THE INVENTION

Chemically defined valency platform molecules comprising at least one high molecular weight polyethylene oxide group are provided. The valency platform molecule may comprise, e.g., at least 2, 3, 4, or more high molecular weight polyethylene oxide groups. The high molecular weight polyethylene oxide group has, for example, a molecular weight of greater than 18,000 Daltons; greater than 22,000 Daltons; greater than 40,000 Daltons; greater than 50,000 Daltons; greater than 80,000 Daltons; greater than 100,000 Daltons, or at least 40,000 Daltons.

In one embodiment, in the valency platform molecule, the high molecular weight polyethylene oxide group has the formula:

wherein n is greater than 500; n is greater than 400; n is greater than 500; n is greater than 600; n is greater than 700; or n is greater than 800.

In one embodiment, the valency platform molecule comprises a core group and at least three arms wherein each arm comprises a terminus. The core group and/or the arms may comprise a high molecular weight polyethylene oxide group. The high molecular weight polyethylene oxide group also may be attached to the core or arm.

In one embodiment, a composition comprising the valency platform molecules disclosed herein is provided, wherein the molecules have a polydispersity less than 1.2.

In one embodiment, the valency platform molecule may comprise at least three reactive conjugating groups such as hydroxyl, thiol, isocyanate, isothiocyanate, amine, alkyl halide, alkylmercurial halide, aldehyde, ketone, carboxylic acid halide, α-halocarbonyl, α,β-unsaturated carbonyl, haloformate ester, carboxylic acid, carboxylic ester, carboxylic anhydride, O-acyl isourea, hydrazide, maleimide, imidate ester, sulfonate ester, sulfonyl halide, α,β-unsaturated sulfone, aminooxy, semicarbazide, or β-aminothiol. In one embodiment, the valency platform molecule comprises at least 3 aminooxy groups and/or at least 3 carbamate groups.

In one embodiment, there is provided a conjugate of a valency platform molecule as disclosed herein and one or more, for example 3, or more, biologically active molecules, such as a saccharide, poly(saccharide), amino acid, poly (amino acid), nucleic acid or lipid. In one embodiment, the conjugate is a B cell toleragen.

In one embodiment, the biologically active molecule is a nucleic acid or analog thereof, and the conjugate is effective for reducing levels of anti-double stranded DNA antibodies, such as the treatment or alleviation of lupus. In another embodiment, the biologically active molecule is a polypeptide comprising a $\beta_2$GPI domain 1 polypeptide or analog thereof, and, for example, the conjugate is effective for reduction of levels of anti-phospholipid (aPL) antibodies and/or the treatment of diseases associated with, for example, anti-phospholipid syndrome, such as antibody mediated thrombosis. In one embodiment, the biologically active molecule is an αGal epitope or analog thereof that specifically binds to an anti-αGal antibody; and optionally the conjugate is effective to induce immunological tolerance in xenotransplantation.

In one embodiment, the biologically active molecule is an analog of a T cell dependent immunogen wherein the analog binds specifically to surface antibody on B cells to which the T cell dependent immunogen binds specifically and the conjugate lacks T cell epitopes capable of activating T cells in said individual.

Also provided are pharmaceutically acceptable compositions comprising the conjugates disclosed herein and a pharmaceutically acceptable carrier.

A further aspect of the invention is a method for treating an antibody mediated disease or other condition in an individual in need of such treatment comprising administering to the individual an effective amount of the conjugates, wherein optionally the conjugates specifically bind to an antibody associated with an antibody-mediated disease.

Yet another aspect of the invention is a method of inducing specific B cell anergy to an immunogen in an individual comprising administering to the individual an effective amount of the conjugates.

Another aspect of the invention is a method of treating an individual for an antibody-mediated pathology in which undesired antibodies are produced in response to an immunogen comprising administering to the individual an effective amount of the conjugates In one embodiment, it is preferred that the total molecular weight of the conjugate is no greater than about 200,000 Daltons, for example, in order for the conjugate to be effective as a functional toleragen and not act as a T cell independent immunogen.

Also provided are compositions, and methods for their use, wherein the composition comprises valency platform molecules including high molecular weight polyethylene oxide groups, wherein the average molecular weight of the polyethylene oxide groups in the valency platform molecules in the composition, is, for example, greater than about 18,000, greater than about 20,000, greater than about 22,000, greater than about 30,000, greater than about 40,000, greater than about 50,000, or greater than about 100,000 Daltons.

Chemically defined valency platform molecules are provided that comprise polyethylene oxide groups which in combination have a high molecular weight. Also provided are compositions, and methods for their use, wherein the composition comprises valency platform molecules including polyethylene oxide groups that have a high molecular weight in combination, and the average molecular weight of the polyethylene oxide groups in combination on the valency platform molecules in the composition, is, for example, greater than about 18,000, greater than about 20,000, or, for example, greater than about 22,000 Daltons.

There are also provided compositions, and methods for their use, comprising valency platform molecules, wherein the valency platform molecules comprise at least one high molecular weight polyethylene oxide group; wherein the molecules have a polydispersity less than about 1.2; and wherein the average molecular weight of the high molecular weight polyethylene oxide groups in the composition is at least about 18,000.

Also provided are conjugates of a chemically defined valency platform molecule and a polypeptide comprising a $\beta_2$GPI domain 1 polypeptide, wherein the conjugate comprises at least one high molecular weight polyethylene oxide group. The high molecular weight polyethylene oxide group has a molecular weight, for example, greater than 22,000 Daltons. The polypeptide in one embodiment specifically binds to a $\beta_2$GPI-dependent antiphospholipid antibody and optionally lacks a T cell epitope capable of activating T cells in an individual having $\beta_2$GPI dependent antiphospholipid antibodies.

In the conjugate, the $\beta_2$GPI domain 1 polypeptide, for example, comprises at least five contiguous amino acids of FIG. 19 (SEQ ID NO: 2); or amino acids Nos. 2–63 of FIG. 19 (SEQ ID NO: 2). The conjugate is for example compound 200, 202, 203, or 205 shown in FIG. 7 or compound 300 shown in FIG. 16, wherein D1 in said structures is for example a polypeptide consisting of amino acids No. 2–63 of SEQ ID No: 2.

A further aspect of the invention is a method for making the conjugates described above comprising: covalently bonding the biologically active molecule to a chemically-defined valency platform molecule to form a conjugate.

In one embodiment, a conjugate is provided as disclosed herein, wherein the conjugate is suitable for inducing specific B cell anergy to a T cell-dependent immunogen implicated in an antibody-mediated pathology in an individual suffering from said pathology, the conjugate comprising a preferably nonimmunogenic valency platform molecule as described herein and at least two analog molecules of the immunogen wherein (a) the analog molecules bind specifically to surface antibody on B cells to which the T cell-dependent immunogen binds specifically and (b) the conjugate lacks T cell epitopes capable of activating T cells in said individual. The analog molecules are for example peptides, polypeptides, proteins, glycoproteins, lipoproteins, carbohydrates, lipids, or lipopolysaccharides.

In another embodiment, there is provided a composition comprising valency platform molecules comprising high molecular weight polyethylene oxide groups, wherein the average molecular weight of the polyethylene oxide groups is greater than about 18,000, greater than about 20,000 or greater than about 22,000.

BRIEF DESCRIPTION OF THE DRAWINGS

FIG. 1 is a reaction scheme showing the synthesis of compound 8.

FIG. 2 is a reaction scheme showing the synthesis of compound 11.

FIG. 3 is a reaction scheme showing the synthesis of compound 17.

FIG. 4 is a reaction scheme showing the synthesis of compound 23.

FIG. 5 shows exemplary valency platform molecule conjugates comprising high molecular weight polyethylene oxide groups.

FIG. 6 shows exemplary valency platform molecule conjugates comprising high molecular weight polyethylene oxide groups.

FIG. 7 shows exemplary valency platform molecule conjugates comprising polyethylene oxide groups.

FIG. 8 shows illustrative Formulas for valency platform molecules comprising aminoxy groups and polyethylene oxide groups.

FIG. 9 shows a scheme for the synthesis of multivalent platform molecules comprising polyethylene oxide groups of varying molecular weight.

FIG. 10 shows a scheme for the synthesis of multivalent platform molecules comprising polyethylene oxide groups and arms.

FIG. 11 shows a scheme for the synthesis of compound 132.

FIG. 12 shows a scheme for the synthesis of compound 136.

FIG. 19 depicts the nucleotide (SEQ ID NO:1) and amino acid (SEQ ID NO:2) sequence of domain 1 of $\beta_2$GPI. Numbers below the lines indicate amino acid positions.

FIG. 20 is a scheme showing the synthesis of a transaminated polypeptide.

MODES FOR CARRYING OUT THE INVENTION

Figure 1:
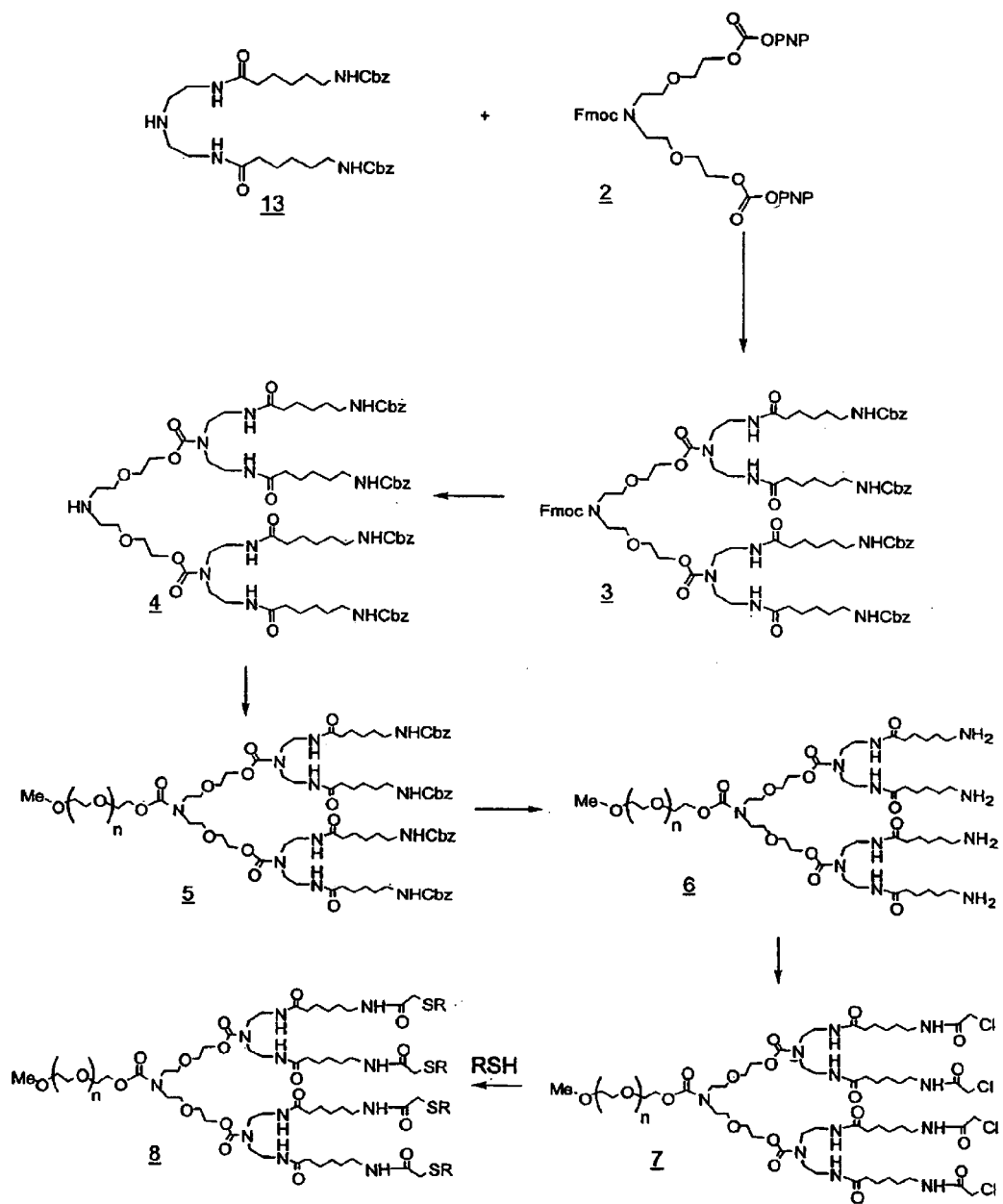

Valency platform molecules comprising high molecular weight polyethylene oxide groups are provided, and conjugates thereof with biologically active molecules, as well as methods for their synthesis and use. Also provided are pharmaceutically acceptable compositions comprising the conjugates disclosed herein, optionally in a pharmaceutically acceptable carrier.

In the complexes of valency platform molecules comprising high molecular weight polyethylene oxide groups with biologically active molecules, advantageously, in a preferred embodiment, the polyethylene oxide groups are not attached directly to the biologically active molecule, such as a polypeptide. Advantageously, the polyethylene oxide group is attached directly to the platform, rather than the protein or other agent, thus potentially reducing the potential of the interference with binding. The attachment of a polyethylene oxide of a selected molecular weight or molecular weight range to the platform is well defined, thus conjugates of biologically active molecules and valency platform molecules comprising high molecular weight polyethylene oxide groups also are homogeneous and well defined.

The valency platform molecules disclosed herein include one or more high molecular weight polyalkylene oxide groups. The presence of the polyalkylene oxide groups on the valency platform molecules also can advantageously improve serum half life and improve activity of biologically active molecules conjugated thereto. In the embodiments described herein, where the term polyethylene oxide is used, also included within the scope of this invention are other polyalkylene oxides such as polypropylene oxide

Pharmaceutically Acceptable Compositions

Pharmaceutically acceptable valency platform molecules comprising high molecular weight polyethylene oxide groups are provided, and conjugates thereof with biologically active molecules, as well as methods for their synthesis and use. Also provided are pharmaceutically acceptable compositions comprising the molecules and conjugates disclosed herein, optionally in a pharmaceutically acceptable carrier.

Carriers for different routes of administration, including oral, intravenous, and aerosol administration are described in the art, for example, in "Remington: The Science and Practice of Pharmacy," Mack Publishing Company, Pennsylvania, 1995, the disclosure of which is incorporated herein by reference. Carriers can include, for example, water, saccharides, polysaccharides, buffers, excipients, and biodegradable polymers such as polyesters, polyanhydrides, polyamino acids and liposomes.

Pharmaceutically acceptable compositions are compositions in a form suitable for administration to an individual, for example, systemic or localized administration to individuals in unit dosage forms, sterile parenteral solutions or suspensions, sterile non-parenteral solutions or oral solutions or suspensions, oil in water or water in oil emulsions and the like.

Polyethylene Oxide

In one embodiment, the valency platform molecules include one or more polyethylene oxide groups with a molecular weight, for example, greater than about 5,000; greater than about 10,000; greater than about 15,000; or greater than about 20,000. The polyethylene oxide group can have a molecular weight, for example, of about 5,000 to 10,000; about 8,000 to 20,000; about 10,000 to 20,000; or about 15,000 to 20,000.

In a composition comprising valency platform molecules, the molecular weight of the polyethylene oxide groups in the valency platform molecule may be a molecular weight that is an average molecular weight of the polyethylene oxide groups, since there may be a molecular weight distribution. Preferably, the molecular weight distribution is narrow. The molecular weights disclosed herein in one embodiment refer to the average molecular weight of a composition comprising the valency platform molecules.

In a preferred embodiment, the valency platform molecule comprises at least one high molecular weight polyethylene oxide group. The valency platform molecule also can include plural high molecular weight polyethylene oxide groups, for example, 2, 3 or more. Alternatively, the high molecular weight polyethylene oxide may be present as a plurality of different polyethylene oxide groups in different locations on the platform which have a high molecular weight in combination. The high molecular weight in combination may be, for example, greater than about 18,000, greater than about 20,000, or for example, greater than about 22,000.

As used herein, the term "high molecular weight polyethylene oxide" group refers to a polyethylene oxide group having a molecular weight greater than about 18,000, greater than about 20,000, or, for example, greater than about 22,000 Daltons. The molecular weight may be, for example, about 20,000–22,000 or about 18,000–22,000.

For example, the high molecular weight polyethylene oxide may be a group having the formula:

$$—(CH_2CH_2O)_n—,$$

wherein n is, for example, greater than about 400, greater than about 450, greater than about 500, or greater than about 550. For example, n is about 400–550, 520 to 600, 550 to 700, 600 to 800, 600 to 900, or 600 to 1000, or more. In another embodiment, n is at least about 600, at least about 700, at least about 800, at least about 900 or at least about 1000.

The high molecular weight polyethylene oxide group can, for example, have a molecular weight greater than about 25,000; greater than about 30,000; or greater than about 40,000 daltons. The high molecular weight polyethylene oxide group further may have, for example, a molecular weight greater than about 50,000, for example about 50,000 to 100,000 or more, for example about 50,000 to 100,000.

In some embodiments, the valency platform molecules include core groups and a plurality of arms extending from the core, wherein said arms comprise a terminus. See, for example, FIGS. 14–16. Optionally, the arms also may branch, increasing the number of termini. The high molecular weight polyethylene groups may be present in the core or in one or more of the arms or may be attached to the valency platform molecule. For example, the valency platform molecule may have the formula:

 Formula 20 wherein Rc represents the core and A represents the two or more arms, wherein Rc and A are independently an organic moiety, and at least one of Rc and A comprises a high molecular weight polyethylene oxide; and $G_1$ if present is an organic moiety;

$G_2$ if present is an organic moiety, for example comprising a reactive conjugating group; and y is two or more, for example, 3, 4, 5, 6, 7, 8, 16 or more.

The core group or one of the arms of the valency platform molecule thus can comprise the polyethylene oxide groups, or the polyethylene oxide group may be optionally attached to a selected location on the valency platform molecule such as on the core or one or more arms. Preferably the arms include a terminus that comprises a reactive group for the attachment of biologically active molecules. The valency platform molecule also may include branching groups that increase the number of arms, and therefore termini of the platform molecule.

Polyethylene oxide groups of molecular weight of for example, about 10,000 to 40,000 Daltons may be useful for promoting suitably long plasma half lives.

Valency Platforms

Any of a variety of valency platform molecules known in the art can be synthesized in a manner to include high molecular weight polyethylene oxide groups as disclosed herein. Methods for making valency platform molecules are described, for example, in U.S. Pat. Nos. 5,162,515; 5,391,785; 5,276,013; 5,786,512; 5,726,329; 5,268,454; 5,552,391; 5,606,047; 5,663,395 and 5,874,409, as well as in U.S. Ser. No. 60/111,641 and PCT US97/10075. In general, these platforms contain core groups or branched core groups which can terminate in, for example, hydroxyl groups, thiols, carboxyl groups, amino groups, aldehydes, ketones, alkyl halides, or aminooxy groups, which optionally can be further modified to provide a preselected reactive conjugating group to permit further attachment of selected molecules thereto. Preferably, the valency platform molecules include at least three reactive conjugating groups. Examples of reactive conjugating groups include hydroxyl, thiol, isocyanate, isothiocyanate, amine, alkyl halide, alkylmercurial halide, aldehyde, ketone, carboxylic acid halide, α-halocarbonyl, α,β-unsaturated carbonyl, haloformate ester, carboxylic acid, carboxylic ester, carboxylic anhydride, O-acyl isourea, hydrazide, maleimide, imidate ester, sulfonate ester, sulfonyl halide, α,β-unsaturated sulfone, aminooxy, semicarbazide, and β-aminothiol.

Valency platforms are prepared from core groups which contain the desired valence, or the valence of a core group can be increased by derivatizing the terminal functionality with branching moieties.

Methods known iA the art for making valency platform molecules, include, for example, a propagation method, or segmental approach. Such methods can be modified, using the appropriate reagents, to provide the desired valency.

In one aspect, valency platform molecules are provided that are substantially monodisperse. The valency platform molecules advantageously have a narrow molecular weight distribution. A measure of the breadth of distribution of molecular weight of a sample of a valency platform molecule is the polydispersity of the sample. Polydispersity is used as a measure of the molecular weight homogeneity or nonhomogeneity of a polymer sample. Polydispersity is calculated by dividing the weight average molecular weight (Mw) by the number average molecular weight (Mn). The value of Mw/Mn is unity for a perfectly monodisperse polymer. Polydispersity (Mw/Mn) is measured by methods available in the art, such as gel permeation chromatography. The polydispersity (Mw/Mn) of a sample of a valency platform molecule is preferably less than 2, more preferably, less than 1.5, or less than 1.2, less than 1.07, less than 1.02, or, e.g., about 1.05 to 1.5 or about 1.05 to 1.2. Typical polymers generally have a polydispersity of 2–5, or in some cases, 20 or more. Advantages of the low polydispersity property of the valency platform molecules include improved biocompatibility and bioavailability since the molecules are substantially homogeneous in size, and variations in biological activity due to a wide variations in molecular weight are minimized. The low polydispersity molecules thus are pharmaceutically optimally formulated and easy to analyze. Further there is controlled valency of the population of molecules in the sample.

In a composition comprising valency platform molecules including high molecular weight polyethylene oxide groups, the average molecular weight of the polyethylene oxide groups on the valency platform molecules in the composition, is, for example, greater than about 18,000, greater than about 20,000, or, for example, greater than about 22,000 Daltons.

In a composition comprising valency platform molecules including polyethylene oxide groups that have a high molecular weight in combination, the average molecular weight of the polyethylene oxide groups in combination on the valency platform molecules in the composition, is, for example, greater than about 18,000, greater than about 20,000, or, for example, greater than about 22,000 Daltons.

In some embodiments, the valency platform molecule may be described as "dendritic," owing to the presence of successive branch points. Dendritic valency platform molecules possess multiple termini, typically 4 or more termini, e.g., 8 termini, or 16 termini.

Note that the Formulas disclosed herein are intended to encompass both symmetric and non-symmetric valency platforms. See, for example, the symmetric molecule M in FIG. 14 and the non-symmetric molecule 300 in FIG. 16.

Using methods described in the detailed description below and the Examples, high molecular weight polyethylene oxide groups can be readily incorporated into the valency platform using the appropriate starting materials and reagents such that the polyethylene oxide units are within the molecule, for example in the core, or in one or more of the arms extending from the core, or are attached to the valency platform molecule via reactive groups present on the molecule.

Exemplary Chemically Defined Valency Platform Molecules

Valency platform molecules can be used that are defined with respect to their chemical structure, valency, homogeneity and a defined chemistry which is amenable to effective conjugation with the appropriate biological and/or chemical molecules.

Chemically-defined, non-polymeric valency platform molecules suitable for use within the present invention include, but are not limited to, biologically compatible and nonimmunogenic carbon-based compounds of the following formulae:

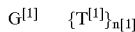  Formula 1a

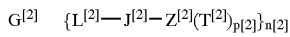  Formula 2a wherein each of $G^{[1]}$ and $G^{[2]}$, if present, is independently a linear, branched or multiply-branched chain comprising 1–2000, or 10,000 or more chain atoms selected from the group C, N, O, Si, P and S;

more preferably, $G^{[2]}$, if present, is a radical derived from a polyalcohol, a polyamine, or a polyglycol; for example, $G^{[2]}$ is selected from the group —$(CH_2)_q$— wherein q=0 to 20, —$CH_2(CH_2OCH_2)_rCH_2$—, wherein r=0 to 300, and $C(CH_2OCH_2CH_2-)_s(OH)_{4-s}$ wherein s=1 to 4, more preferably s=3 to 4;

each of the $n^{[1]}$ moieties shown as $T^{[1]}$ and each of the $p^{[2]} \times n^{[2]}$ moieties shown as $T^{[2]}$ is independently chosen from the group $NHR^{SUB}$ (amine), $C(=O)NHNHR^{SUB}$ (hydrazide), $NHNHR^{SUB}$ (hydrazine), $C(=O)OH$ (carboxylic acid), $C(=O)OR^{ESTER}$ (activated ester), $C(=O)OC(=O)R^B$ (anhydride), $C(=O)X$ (acid halide), $S(=O)_2X$ (sulfonyl halide), $C(=NR^{SUB})OR^{SUB}$ (isidate ester), NCO (isocyanate), NCS (isothiocyanate), $OC(=O)X$ (haloformate), $C(=O)OC(=NR^{SUB})NHR^{SUB}$ (carbodiimide adduct), $C(=O)H$ (aldehyde), $C(=O)R^B$ (ketone), SH(sulfhydryl or thiol), OH (alcohol), $C(=O)CH_2X$ (haloacetyl), $R^{ALK}X$ (alkyl halide), $S(=O)_2OR^{ALK}X$ (alkyl sulfonate), $NR^1R^2$ wherein $R^1R^2$ is —$C(=O)CH=CHC(=O)$-(maleimide), $C(=O)CR^B=CR^B_2$ (α,β-unsaturated carbonyl), $R^{ALK}$—Hg—X (alkyl mercurial), and $S(=O)CR^B=CR^B_2$ (α,β-unsaturated sulfone);

in one embodiment each of the $n^{[1]}$ moieties shown as $T^{[1]}$ and each of the $p^{[2]} \times n^{[2]}$ moieties shown as $T^{[2]}$ is independently chosen from the group $NHR^{SUB}$ (amine), $C(=O)CH_2X$ (haloacetyl), $R^{ALK}X$ (alkyl halide), $S(=O)_2OR^{ALK}X$ (alkyl sulfonate), $NR^1R^2$ wherein $R^1R^2$ is —$C(=O)CHCHC(=O)$-(maleimide), $C(=O)CR^B=CR^B_2$ (α,β-unsaturated carbonyl), $R^{ALK}$—Hg—X (alkyl mercurial), and $S(=O)CR^B=CR^B_2$ (α,β-unsaturated sulfone);

for example each of the $n^{[1]}$ moieties shown as $T^{[1]}$ and each of the $p^{[2]} \times n^{[2]}$ moieties shown as $T^{[2]}$ is independently chosen from the group $NHR^{SUB}$ (amine), $C(=O)CH_2X$ (haloacetyl), $NR^1R^2$ wherein $R^1R^2$ is —$C(=O)CHCHC(=O)$-(maleimide), and $C(=O)CR^B=CR^B_2$ (α,β-unsaturated carbonyl);

in one embodiment, all of the $n^{[1]}$ moieties shown as $T^{[1]}$ and all of the $p^{[2]} \times n^{[2]}$ moieties shown as $T^{[2]}$ are identical; wherein each X is independently a halogen of atomic number greater than 16 and less than 54 or other good leaving group (i.e., weak bases such as alkyl or alkyl-substituted sulfonates or sulfates and the like, aryl or aryl-substituted sulfonates or sulfates and the like that act similarly to a halogen in this setting);

each $R^{ALK}$ is independently a linear, branched, or cyclic alkyl (1–20C) group;

each $R^{SUB}$ is independently H, linear, branched, or cyclic alkyl (1–20C), aryl (6–20C), or alkaryl (7–30C);

each $R^{ESTER}$ is independently N-succinimidyl, p-nitrophenyl, pentafluorophenyl, tetrafluorophenyl, pentachlorophenyl, 2,4,5-trichlorophenyl, 2,4-dinitrophenyl, cyanomethyl and the like, or other activating group such as 5-chloro, 8-quinolone, 1-piperidine, N-benzotriazole and the like;

each $R^B$ is independently a radical comprising 1–50 atoms selected from the group C, H, N, O, Si, P and S;

each of the $n^{[2]}$ moieties shown as $L^{[2]}$, if present, is independently chosen from the group O, $NR^{SUB}$ and S;

each of the $n^{[2]}$ moieties shown as $J^{[2]}$, if present, is independently chosen from the group $C(=O)$ and $C(=S)$;

$n^{[1]}$=1 to 32, more preferably $n^{[1]}$=2 to 16, even more preferably $n^{[1]}$=2 to 8, most preferably $n^{[1]}$=2 to 4;

$n^{[2]}$=1 to 32, more preferably $n^{[2]}$=1 to 16, even more preferably $n^{[2]}$=1 to 8, yet more preferably $n^{[2]}$=1 to 4, most preferably $n^{[2]}$=1 to 2;

$p^{[2]}$=1 to 8, more preferably $p^{[2]}$=1 to 4, most preferably $p^{[2]}$=1 to 2;

with the proviso that the product $n^{[2]} \times p^{[2]}$ be greater than 1 and less than 33;

each of the $n^{[2]}$ moieties shown as $Z^{[2]}$ is independently a radical comprising 1–200 atoms selected from the group C, H, N, O, Si, P and S, containing attachment sites for at least $p^{[2]}$ functional groups on alkyl, alkenyl, or aromatic carbon atoms;

in one embodiment, all of the $n^{[2]}$ moieties shown as $Z^{[2]}$ are identical;

in one embodiment, each of the $n^{[2]}$ moieties shown as $Z^{[2]}$ is independently described by a formula chosen from the group:

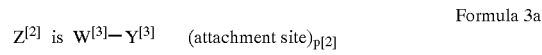  Formula 3a

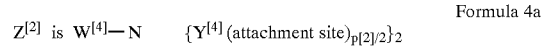  Formula 4a

  Formula 5a wherein each of the $n^{[2]}$ moieties shown as $W^{[3]}$, $W^{[4]}$, or $W^{[5]}$, if present, is independently a radical comprising 1–100 atoms selected from the group C, H, N, O, Si, P and S;

each of the $n^{[2]}$ moieties shown as $Y^{[3]}$, each of the $2 \times n^{[2]}$ moieties shown as $Y^{[4]}$, and each of the $2 \times n^{[2]}$ moieties shown as $Y^{[5]}$ is independently a radical comprising 1–100 atoms selected from the group C, H, N, O, Si, P and S, containing attachment sites for at least $p^{[2]}$ (for $Y^{[3]}$) or $p^{[2]}/2$ (for $Y^{[4]}$ and $Y^{[5]}$, where $p^{[2]}/2$ is an integer) functional groups on alkyl, alkenyl, or aromatic carbon atoms;

in one embodiment, each of the $n^{[2]}$ moieties shown as $W^{[3]}$, if present, is independently chosen from the group $(CH_2)_r$, $(CH_2CH_2O)_r$, $NR^{SUB}(CH_2CH_2O)_rCH_2CH_2$, and $NR_{SUB}(CH_2)_rNR^{SUB}C(=O)$, wherein r=1 to 10;

in one embodiment, each of the $n^{[2]}$ moieties shown as $Y^{[3]}$ is independently linear, branched, or cyclic alkyl (1–20C), aryl (6–20C), or alkaryl (7–30C); most preferably, each of the $n^{[2]}$ moieties shown as $Y^{[3]}$ is independently chosen from the group $C_6H_4$ (phenyl-1,4-diradical), $C_6H_3$ (phenyl-1,3,5-triradical), and $(CH_2)_r$ wherein r=1 to 10;

for example, each of the $n^{[2]}$ moieties shown as $W^{[4]}$, if present, is independently chosen from the group $(CH_2)_rC(=O)$ and $(CH_2)_rNR^{SUB}C(=O)$, wherein r=1 to 10;

for example, each of the $2 \times n^{[2]}$ moieties shown as $Y^{[4]}$, is independently chosen from the group $(CH_2)_r$, $(CH_2)_rNR^{SUB}C(=O)(CH_2)_q$, $(CH_2)_rC(=O)NR^{SUB}(CH_2)_q$, $(CH_2)_rNR^{SUB}C(=O)(CH_2)_qNR^{SUB}C(=O)(CH_2)_r$, $(CH_2)_rC(=O)NR^{SUB}(CH_2)_qNR^{SUB}C(=O)(CH_2)_r$, $(CH_2)_rNR^{SUB}C(=O)(CH_2CH_2O)_qCH_2CH_2$, and $(CH_2)_rC(=O)NR^{SUB}(CH_2CH_2O)_qCH_2CH_2$, wherein r=1 to 10, more preferably r=2 to 6, and q=1 to 10, more preferably q=1 to 3;

in one embodiment, each of the n[2] moieties shown as W[5], if present, is independently chosen from the group $(CH_2)_rC(=O)NR^{SUB}$ and $(CH_2)_rNR^{SUB}C(=O)NR^{SUB}$, wherein r=1 to 10;

in one embodiment, each of the 2×n[2] moieties shown as Y[5], is independently chosen from the group $(CH_2)_r$ and $(CH_2)_rC(=O)NR^{SUB}(CH_2)_q$, wherein r=1 to 10 and q=1 to 10.

In a further embodiment, a conjugate comprises a chemically-defined, non-polymeric valency platform molecule and a biologically active molecule is provided. The biologically active molecule may be coupled to a linker molecule before being coupled to a valency platform molecule.

Exemplary of suitable linker molecules are 6 carbon thiols such as HAD, a thio-6 carbon chain phosphate, and HAD$_p$S, a thio-6 carbon chain phosphorothioate. Chemically-defined valency platform molecules are formed, for example, by reacting amino modified-PEG with 3,5-bis-(iodoacetamido) benzoyl chloride (hereinafter "DABA"); 3-carboxypropionamide-N,N-bis-[(6'-N'-carbobenzyloxyamino-hexyl)acetamide] 4"-nitrophenyl ester (hereinafter "BAHA"); 3-carboxypropionamide-N,N-bis-[(8'-N'-carbobenzyloxyamino-3', 6'-dioxaoctyl)acetamide] 4"-nitrophenyl ester (hereinafter "BAHA$_{OX}$"); or by reacting PEG-bis-chloroformate with N,N-di(2-[6'-N'-carbobenzyloxyamino-hexanoamido]ethyl)amine (hereinafter "AHAB") to form chemically-defined valency platform molecules.

Also provided are chemically-defined, non-polymeric valency platform molecules of the formulae:

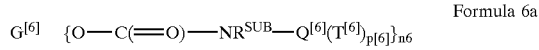

Formula 6a $G^{[6]}\ \{O-C(=O)-NR^{SUB}-Q^{[6]}(T^{[6]})_{p[6]}\}_{n6}$

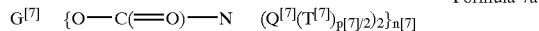

Formula 7a $G^{[7]}\ \{O-C(=O)-N\ (Q^{[7]}(T^{[7]})_{p[7]/2})_2\}_{n[7]}$ wherein each of G[6] and G[7], if present, is independently a linear, branched or multiply-branched chain comprising 1–2000, or 10,000 or more, chain atoms selected from the group C, N, O, Si, P and S; more preferably, each of G[6] and G[7] is a radical derived from a polyalcohol, a polyamine, or a polyglycol; most preferably, each of G[6] and G[7] is selected from the group $-(CH_2)_q-$ wherein q=0 to 20, $-CH_2(CH_2OCH_2)_rCH_2-$, wherein r=0 to 300, and $C(CH_2OCH_2CH_2-)_s(OH)_{4-s}$ wherein s=1 to 4, more preferably s=3 to 4;

each of the n[6]×p[6] moieties shown as T[6] and each of the n[7]×p[7] moieties shown as T[7] is independently chosen from the group NHR$^{SUB}$ (amine), C(=O)NHNHR$^{SUB}$ (hydrazide), NHNHR$^{SUB}$ (hydrazine), C(=O)OH (carboxylic acid), C(=O)OR$^{ESTER}$ (activated ester), C(=O)OC(=O)R$^B$ (anhydride), C(=O)X (acid halide), S(=O)$_2$X (sulfonyl halide), C(=NR$^{SUB}$)OR$^{SUB}$ (isidate ester), NCO (isocyanate), NCS (isothiocyanate), OC(=O)X (haloformate), C(=O)OC(=NR$^{SUB}$)NHR$^{SUB}$ (carbodiimide adduct), C(=O)H (aldehyde), C(=O)R$^B$ (ketone), SH(sulfhydryl or thiol), OH (alcohol), C(=O)CH$_2$X (haloacetyl), R$^{ALK}$X (alkyl halide), S(=O)$_2$OR$^{ALK}$X (alkyl sulfonate), NR$^1$R$^2$ wherein R$^1$R$^2$ is $-C(=O)CHCHC(=O)$-(maleimide), C(=O)CR$^B$=CR$^B_2$ (α,β-unsaturated carbonyl), R$^{ALK}$—Hg—X (alkyl mercurial), and S(=O)CR$^B$=CR$^B_2$ (α,β-unsaturated sulfone);

more preferably, each of the n[6]×p[6] moieties shown as T[6] and each of the n[7]×p[7] moieties shown as T[7] is independently chosen from the group NHR$^{SUB}$ (amine), C(=O)CH$_2$X (haloacetyl), R$^{ALK}$X (alkyl halide), S(=O)$_2$OR$^{ALK}$X (alkyl sulfonate), NR$^1$R$^2$ wherein R$^1$R$^2$ is $-C(=O)CHCHC(=O)$-(maleimide), C(=O)CR$^B$=CR$^B_2$ (α,β-unsaturated carbonyl), R$^{ALK}$—Hg—X (alkyl mercurial), and S(=O)CR$^B$=CR$^B_2$ (α,β-unsaturated sulfone);

even more preferably each of the n[6]×p[6] moieties shown as T[6] and each of the n[7]×p[7] moieties shown as T[7] is independently chosen from the group NHR$^{SUB}$ (amine), C(=O)CH$_2$X (haloacetyl), NR$^1$R$^2$ wherein R$^1$R$^2$ is $-C(=O)CH=CHC(=O)$-(maleimide), and C(=O)CR$^B$=CR$^B_2$ (α,β-unsaturated carbonyl);

most preferably, all of the n[6]×p[6] moieties shown as T[6] and all of the n[7]×p[7] moieties shown as T[7] are identical; wherein each X is independently a halogen of atomic number greater than 16 and less than 54 or other good leaving group;

each R$^{ALK}$ is independently a linear, branched, or cyclic alkyl (1–20C) group;

each R$^{SUB}$ is independently H, linear, branched, or cyclic alkyl (1–20C), aryl (1–20C), or alkaryl (1–30C);

each R$^{ESTER}$ is independently N-hydroxysuccinimidyl, p-nitrophenoxy, pentafluorophenoxy, or other activating group;

each R$^B$ is independently a radical comprising 1–50 atoms selected from the group C, H, N, O, Si, P and S;

n[6]=1 to 32, more preferably n[6]=1 to 16, even more preferably n[6]=1 to 8, yet more preferably n[6]=1 to 4, most preferably n[6]=1 to 2;

p[6]=1 to 8, more preferably p[6]=1 to 4, most preferably p[6]=1 to 2;

with the proviso that the product n[6]×p[6] be greater than 1 and less than 33;

n[7]=1 to 32, more preferably n[7]=1 to 16, even more preferably n[7]=1 to 8, yet more preferably n[7]=1 to 4, most preferably n[7]=1 to 2;

p[7]=1 to 8, more preferably p[7]=1 to 4, most preferably p[7]=1 to 2;

with the proviso that the product n[7]×p[7] be greater than 1 and less than 33;

each of the n[6] moieties shown as Q[6] and each of the 2×n[7] moieties shown as Q[7] is independently a radical comprising 1–100 atoms selected from the group C, H, N, O, Si, P and S, containing attachment sites for at least p[6] (for Q[6]) or p[7]/2 (for Q[7], where p[7]/2 is an integer) functional groups on alkyl, alkenyl, or aromatic carbon atoms;

more preferably, all of the n[6] moieties shown as Q[6] are identical;

more preferably, all of the 2×n[7] moieties shown as Q[7] are identical;

more preferably, each of the n[6] moieties shown as Q[6], is independently chosen from the group CH[(CH$_2$)$_r$ (attachment site)]$_2$ and CH[(CH$_2$)$_r$C(=O)NR$^{SUB}$(CH$_2$)$_q$ (attachment site)]$_2$, wherein r=1 to 10 and q=1 to 10;

more preferably, each of the 2×n[7] moieties shown as Q[7], is independently chosen from the group (CH$_2$)$_r$, (CH$_2$)$_r$NR$^{SUB}$C(=O)(CH$_2$)$_q$, (CH$_2$)$_r$C(=O)NR$^{SUB}$(CH$_2$)$_q$, (CH$_2$)$_r$NR$^{SUB}$C(=O)(CH$_2$)$_q$NR$^{SUB}$C(=O)(CH$_2$)$_r$, (CH$_2$)$_r$C(=O)NR$^{SUB}$(CH$_2$)$_q$NR$^{SUB}$C(=O)(CH$_2$)$_r$, (CH$_2$)$_r$NR$^{SUB}$C(=O)(CH$_2$CH$_2$O)$_q$CH$_2$CH$_2$, and (CH$_2$)$_r$C(=O)NR$^{SUB}$(CH$_2$CH$_2$O)$_q$CH$_2$CH$_2$, wherein r=1 to 10, more preferably r=2 to 6, and q=1 to 10, more preferably q=1 to 3;

These chemically defined platform molecules, as described in U.S. Pat. No. 5,552,391 can be further modified as described herein to include high molecular weight polyethylene oxide groups.

Aminooxy Valency Platform Molecules

In one embodiment, the valency platform molecules comprise one or more high molecular weight polyethylene oxide groups, as well as aminooxy groups, for example, 1 to 100, e.g, 1–50, 2–16, 4–16, or e.g., 2, 3, 4, 8, 16, 32 or more aminooxy groups. In one embodiment, the valency platform molecule has at least 2, 3, 4, 5 or more aminooxy groups. Aminooxy valency platform molecules are described in U.S. Provisional Patent Application No. 60/138,260, filed Jun. 8, 1999.

Also provided are conjugates thereof with other molecules such as biologically active molecules, and methods for their synthesis. The aminooxy groups provide attachment sites for the covalent attachment of other molecules. The molecule may comprise, e.g., at least 3 aminooxy groups, or 4,5 or more aminooxy groups.

In one embodiment, there is provided a valency platform molecule having the formula:

  Formula 1b wherein in one embodiment:

m is 1–50 or more, e.g., 3–50; and

R is an organic moiety comprising 1–10,000 atoms or more selected from the group consisting of H, C, N, O, P, Si and S atoms; and wherein the valency platform molecule comprises at least one high molecular weight polyethylene oxide group, for example having the formula —$(CH_2CH_2O)_n$—, wherein n is greater than 500, for example 500 to 700, or 600 to 800, or 1000, or more.

In another embodiment, there is provided a valency platform molecule having the formula:

  Formula 2b wherein in one embodiment:

y is 1 to 16;

n is 1 to 32;

wherein in one embodiment the product of y*n (y multiplied by n) is at least 3;

$R^c$ and each $G_1$ are independently an organic moiety; and wherein the valency platform molecule comprises at least one high molecular weight polyethylene oxide group, for example having the formula —$(CH_2CH_2O)_n$—, wherein n is greater than 500, for example 500 to 700, or 600 to 800, or 1000, or more.

In one embodiment, $R^c$ and each $G_1$ are independently an organic moiety comprising atoms selected from the group of H, C, N, O, P, Si and S atoms The molecules may be provided for example in a composition having a polydispersity less than 1.2.

In another embodiment, a valency platform molecule is provided having a formula selected from the group consisting of:

  Formula 3b;

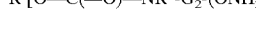  Formula 4b;

  Formula 5b;

  Formula 6b;

  Formula 7b; and

  Formula 8b;

wherein, for example:

y is 1 to 16;

n is 1 to 32, wherein in one embodiment the product of y*n (y multiplied by n) is at least 3;

$R^1$ is H, alkyl, heteroalkyl, aryl, heteroaryl or $G_2$-$(ONH_2)_n$; and $R^c$ and each $G_2$ are independently organic moieties comprising atoms selected from the group of H, C, N, O, P, Si and S atoms; and wherein the valency platform molecule comprises at least one high molecular weight polyethylene oxide group, for example having the formula —$(CH_2CH_2O)_n$—, wherein n is greater than 500, for example 500 to 700, or 600 to 800, or 1000, or more.

In one embodiment, $R^C$ and each $G_2$ independently are selected from the group consisting of:

hydrocarbyl groups consisting only of H and C atoms and having 1 to 5,000 or 1 to 200 carbon atoms;

organic groups consisting only of carbon, oxygen, and hydrogen atoms, and having 1–5,000, or 1 to 200 carbon atoms;

organic groups consisting only of carbon, oxygen, nitrogen, and hydrogen atoms, and having from 1 to 5,000, or 1 to 200 carbon atoms;

organic groups consisting only of carbon, oxygen, sulfur, and hydrogen atoms, and having from 1 to 5,000, or 1 to 200 carbon atoms;

organic groups consisting only of carbon, oxygen, sulfur, nitrogen and hydrogen atoms and having from 1 to 5,000 or 1 to 200 carbon atoms.

In one embodiment of the valency platform molecule, $R^c$ is selected from the group consisting of a C1–200 hydrocarbon moiety; a C1–200 alkoxy moiety; and a C1–200 hydrocarbon moiety comprising an aromatic group.

$R^c$ optionally may comprise an oxyalkylene moiety, such as an oxyethylene moiety (—$CH_2CH_2O$—). In one embodiment $R^c$ comprises oxyethylene units:

wherein n is 1–500, e.g., 1–200, 1–100 or 1–20. Optionally n is greater than 500, for example, 500–700, or 600–800 or 1000 or more.

As used herein "oxyethylene, oxypropylene and oxyalkylene" are used interchangably with "ethylene oxide, propylene oxide and alkylene oxide".

In one embodiment, each $G_2$ independently comprises a functional group selected from the group consisting of alkyl, heteroalkyl, aryl, and heteroaryl.

In another embodiment, each $G_2$ independently comprises a functional group selected from the group consisting of a C1–200 hydrocarbon moiety; a C1–200 alkoxy moiety; and a C1–200 hydrocarbon moiety comprising an aromatic group.

Each $G_2$ independently can comprise an oxyalkylene moiety, such as an oxyethlyene moiety (—$CH_2CH_2O$—). In one embodiment, each $G_2$ independently comprises oxyethylene units:

wherein n is 1–500, e.g., 1–200, 1–100 or 1–20. Optionally n is greater than 500, for example, 500–700, or 600–800 or 1000 or more.

In one embodiment of the valency platform molecule each $G_2$ independently comprises a functional group selected from the group consisting of: amine; amide; ester; ether; ketone; aldehyde; carbamate; thioether; piperazinyl; piperidinyl; alcohol; polyamine; polyether; hydrazide; hydrazine; carboxylic acid; anhydride; halo; sulfonyl; sulfonate; sulfone; cyanate; isocyanate; isothiocyanate; formate; carbodiimide; thiol; oxime; imine; aminooxy; and maleimide.

In another embodiment, compounds of Formulas 9–13 shown in FIG. 8 are provided. In Formulas 9–13, in one embodiment, $R_c$ and $G_2$ are as defined above, and n is about 1–500, e.g., 1–200, 1–100 or 1–50. Optionally n is greater than 500, for example, 500–700, or 600–800 or 1000 or more.

In one embodiment, in Formulas 3b–8b and 9–13, at least one of $R_c$ and $G_2$ comprises at least one high molecular weight polyethylene oxide group, for example having the formula $-(CH_2CH_2O)_n-$, wherein n is greater than 500, for example 500 to 700, or 600 to 800, or 1000, or more.

Valency Platform Molecules Comprising Carbamate Linkages

In another embodiment, valency platform molecules comprising carbamate linkages, as described in PCT US99/29338 and U.S. Ser. No. 09/47,607, filed Dec. 8, 1999 can be modified to include high molecular weight polyethylene oxide.

In one embodiment, the valency platform compounds comprise a carbamate linkage, for example having the structure shown in Formulae Ic, IIc, and IIIc, IVc, Vc, and VIc, wherein the valency platform compound further comprises at least one high molecular weight polyethylene oxide group:

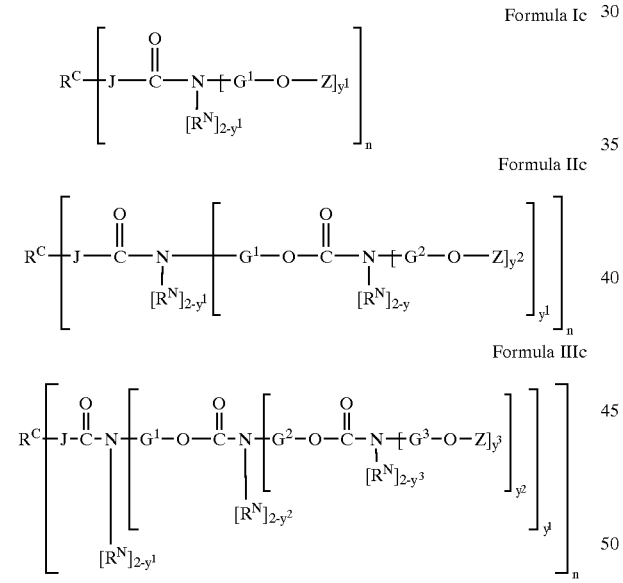

wherein:
n is a positive integer from 1 to 10;
$y^1$, $y^2$, and $y^3$ are independently 1 or 2;
J independently denotes either an oxygen atom or a covalent bond;
$R^C$ is selected from the group consisting of:
  hydrocarbyl groups having from 1 to 20 carbon atoms;
  organic groups consisting only of carbon, oxygen, and hydrogen atoms, and having from 1 to 20 carbon atoms;
  organic groups consisting only of carbon, oxygen, nitrogen, and hydrogen atoms, and having from 1 to 20 carbon atoms;
  organic groups consisting only of carbon, oxygen, sulfur, and hydrogen atoms, and having from 1 to 20 carbon atoms;

each $G^1$, $G^2$, and $G^3$ is independently selected from the group consisting of:
  hydrocarbyl groups having from 1 to 20 carbon atoms;
  organic groups consisting only of carbon, oxygen, and hydrogen atoms, and having from 1 to 20 carbon atoms;
  organic groups consisting only of carbon, oxygen, nitrogen, and hydrogen atoms, and having from 1 to 20 carbon atoms;
each $R^N$ is independently selected from the group consisting of:
  hydrogen;
  linear or branched alkyl groups having from 1 to 15 carbon atoms;
  alkyl groups comprising an alicyclic structure and having from 1 to 15 carbon atoms;
  aromatic groups having from 6 to 20 carbon atoms;
  heteroaromatic groups having from 3 to 20 carbon atoms;
each Z is independently selected from the group consisting of:

—H

—C(=O)OR$^{CARB}$

—C(=O)R$^{ESTER}$

—C(=O)NR$^A$R$^B$ wherein:
each R$^{CARB}$ is organic groups comprising from 1 to about 20 carbon atoms;
each R$^{ESTER}$ is organic groups comprising from 1 to about 20 carbon atoms;
each group —NR$^A$R$^B$ is independently selected from the group consisting of:

—NH$_2$

—NHR$^A$

—NR$^A$R$^B$

—NR$^{AB}$ wherein each monovalent R$^A$ and R$^B$ and each divalent R$^{AB}$ is independently an organic group comprising from 1 to 20 carbon atoms, and further comprising a reactive conjugating functional group; and wherein the valency platform molecule comprises at least one high molecular weight polyethylene oxide group, for example having the formula $-(CH_2CH_2O)_n-$, wherein n is greater than 500, for example 500 to 700, or 600 to 800, or 1000, or more.

In one embodiment, said compound has the structure of Formula Ic. In one embodiment, said compound has the structure of Formula IIc. In one embodiment, said compound has the structure of Formula IIIc. In one embodiment, said compound has the structure of Formula IVc. In one embodiment, n is a positive integer from 2 to 4. In one embodiment, $y^1$, $y^2$, and $y^3$ are each 2. In one embodiment, J is an oxygen atom. In one embodiment, J is a covalent bond. In one embodiment, $R^C$ is selected from the group consisting of hydrocarbyl groups having from 1 to 20 carbon atoms. In one embodiment, $R^C$ is selected from the group consisting of:

—CH₂—;   —CH₂CH₂—;   —CH₂CH₂CH₂—;

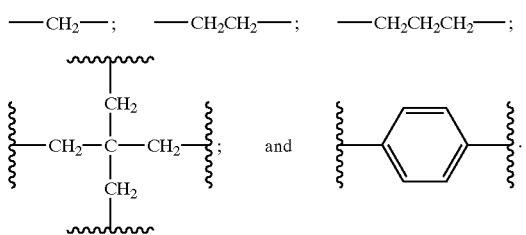 and 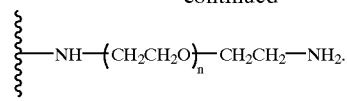

In one embodiment, $R^C$ is selected from the group consisting of organic groups consisting only of carbon, oxygen, and hydrogen atoms, and having from 1 to 20 carbon atoms. In one embodiment, $R^C$ is:

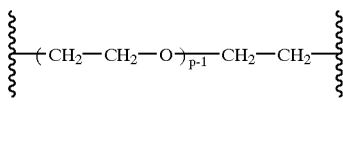

wherein p is a positive integer from 2 to 20. In one embodiment, each $G^1$, $G^2$, and $G^3$ is independently selected from the group consisting of hydrocarbyl groups having from 1 to 20 carbon atoms. In one embodiment, each $G^1$, $G^2$, and $G^3$ is —$(CH_2)_q$— wherein q is a positive integer from 1 to 20. In one embodiment, each $G^1$, $G^2$, and $G^3$ is independently selected from the group consisting of organic groups consisting only of carbon, oxygen, and hydrogen atoms, and having from 1 to 20 carbon atoms. In one embodiment, each $G^1$, $G^2$, and $G^3$ is:

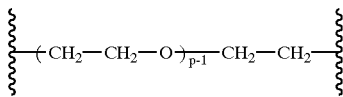

wherein p is a positive integer from 2 to 20. In one embodiment, $R^N$ is independently selected from the group consisting of —H, —$CH_3$, and —$CH_2CH_3$. In one embodiment, each group —$NR^A R^B$ is independently selected from the group consisting of:

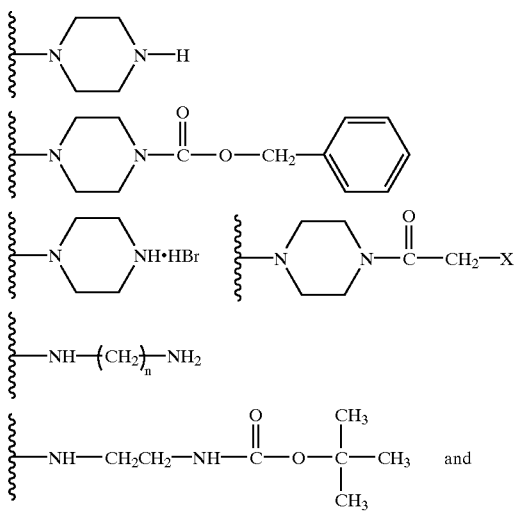

-continued

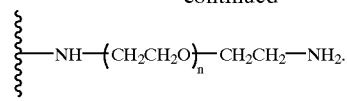

Another aspect of the present invention pertains to a valency platform compound having the structure of one of the following formulae:

Formula IVc
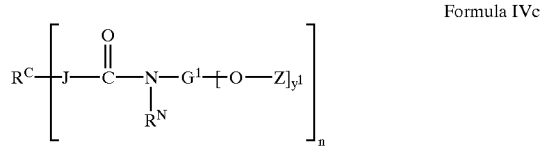

Formula Vc
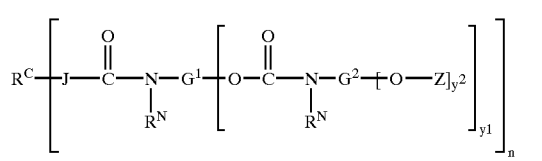

Formula VIc
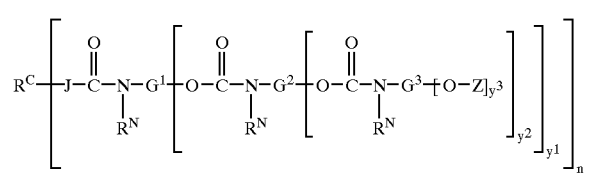

wherein:
n is a positive integer from 1 to 10;
$y^1$, $y^2$, and $y^3$ are independently a positive integer from 1 to 10;
J independently denotes either an oxygen atom or a covalent bond;
$R^C$ is selected from the group consisting of:
  hydrocarbyl groups having from 1 to 20 carbon atoms;
  organic groups consisting only of carbon, oxygen, and hydrogen atoms, and having from 1 to 20 carbon atoms;
  organic groups consisting only of carbon, oxygen, nitrogen, and hydrogen atoms, and having from 1 to 20 carbon atoms;
  organic groups consisting only of carbon, oxygen, sulfur, and hydrogen atoms, and having from 1 to 20 carbon atoms;
each $G^1$, $G^2$, and $G^3$ is independently selected from the group consisting of:
  hydrocarbyl groups having from 1 to 20 carbon atoms;
  organic groups consisting only of carbon, oxygen, and hydrogen atoms, and having from 1 to 20 carbon atoms;
  organic groups consisting only of carbon, oxygen, nitrogen, and hydrogen atoms, and having from 1 to 20 carbon atoms;
each $R^N$ is independently selected from the group consisting of:
  hydrogen;
  linear or branched alkyl groups having from 1 to 15 carbon atoms;
  alkyl groups comprising an alicyclic structure and having from 1 to 15 carbon atoms;
  aromatic groups having from 6 to 20 carbon atoms;
  heteroaromatic groups having from 3 to 20 carbon atoms;

each Z is independently selected from the group consisting of:

—H

—C(=O)OR$^{CARB}$

—C(=O)R$^{ESTER}$

—C(=O)NR$^A$R$^B$ wherein:
each R$^{CARB}$ is organic groups comprising from 1 to about 20 carbon atoms;
each R$^{ESTER}$ is organic groups comprising from 1 to about 20 carbon atoms;
each group —NR$^A$R$^B$ is independently selected from the group consisting of:

—NH$_2$

—NHR$^A$

—NR$^A$R$^B$

—NR$^{AB}$ wherein each monovalent R$^A$ and R$^B$ and each divalent R$^{AB}$ is independently an organic group comprising from 1 to 20 carbon atoms, and further comprising a reactive conjugating functional group; and
wherein the valency platform molecule comprises at least one high molecular weight polyethylene oxide group, for example having the formula —(CH$_2$CH$_2$O)$_n$—, wherein n is greater than 500, for example 500 to 700, or 600 to 800, or 1000, or more.

In one embodiment, said compound has the structure of Formula IVc. In one embodiment, said compound has the structure of Formula Vc. In one embodiment, said compound has the structure of Formula VIc. In one embodiment, n is a positive integer from 2 to 4. In one embodiment, y$^1$, y$^2$, and y$^3$ are each 2. In one embodiment, J is an oxygen atom. In one embodiment, J is a covalent bond. In one embodiment, R$^C$ is selected from the group consisting of hydrocarbyl groups having from 1 to 20 carbon atoms. In one embodiment, R$^C$ is selected from the group consisting of:

—CH$_2$—; —CH$_2$CH$_2$—; —CH$_2$CH$_2$CH$_2$—;

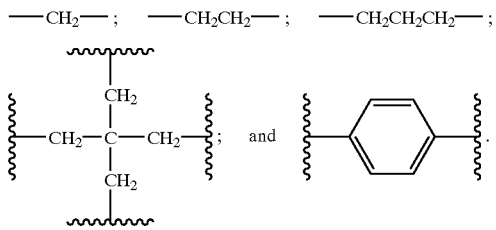 and 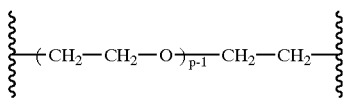

In one embodiment, R$^C$ is selected from the group consisting of organic groups consisting only of carbon, oxygen, and hydrogen atoms, and having from 1 to 20 carbon atoms. In one embodiment, R$^C$ is:

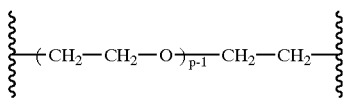

wherein p is a positive integer from 2 to 20. In one embodiment, each G$^1$, G$^2$, and G$^3$ is independently selected from the group consisting of hydrocarbyl groups having from 1 to 20 carbon atoms. In one embodiment, each G$^1$, G$^2$, and G$^3$ is selected from the group consisting of:

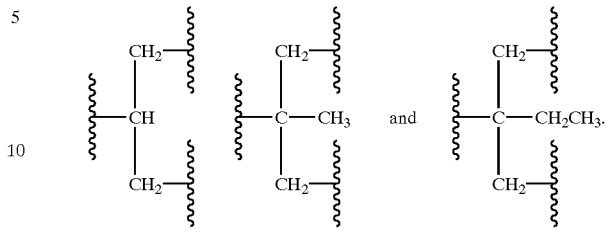

In one embodiment, each G$^1$, G$^2$, and G$^3$ is independently selected from the group consisting of organic groups consisting only of carbon, oxygen, and hydrogen atoms, and having from 1 to 20 carbon atoms. In one embodiment, each R$^N$ is independently selected from the group consisting of —H, —CH$_3$, and —CH$_2$CH$_3$. In one embodiment, each group —NR$^A$R$^B$ is independently selected from the group consisting of:

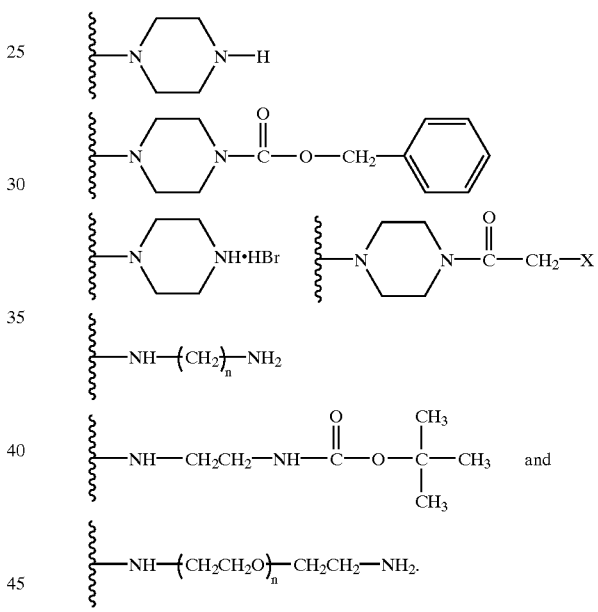

In Formulas Ic, IIc, IIIc, IVc, Vc, and VIc, in one embodiment at least one of R$^c$, G$^1$, G$^2$ and G$^3$ comprise at least one high molecular weight polyethylene oxide group, for example having the formula —(CH$_2$CH$_2$O)$_n$—, wherein n is greater than 500, for example 500 to 700, or 600 to 800, or 1000, or more.

Preparation of Valency Platform Molecules

Methods known in the art to make valency platform molecules may be modified to permit the incorporation of high molecular weight polyethylene oxides in the molecule. Methods for making valency platform molecules are described, for example, in U.S. Pat. Nos. 5,162,515; 5,391,785; 5,276,013; 5,786,512; 5,726,329; 5,268,454; 5,552,391; 5,606,047; 5,663,395; and 5,874,409; as well as U.S. Ser. Nos. 60/111,641; 09/457,607; PCT WO 00/34231; PCT US97/10075; U.S. Ser. No. 09/590,592; and PCT/US/00/15968.

Methods known the art for making valency platform molecules, include, for example, a propagation method, or segmental approach. Such methods can be modified, using the appropriate reagents, to provide polyethylene oxide groups on the resulting molecule. Exemplary methods are demonstrated in the Examples herein.

The valency platforms can be prepared from a segmental approach in which segments are independently synthesized and subsequently attached to a core group. An alternative to the core propagation process is an iterative process that may be used to generate a dendritic structure.

Examples of core compounds include alcohol containing core compounds methanol, ethanol, propanol, isopropanol, and methoxypolyethylene glycol, mono-hydroxylamines, ethylene glycol, diethylene glycol, triethylene glycol, tetraethylene glycol, pentaethylene glycol, hexaethylene glycol, 1,4-bis-(hydroxymethyl)benzene and polyethylene glycol $HO(CH_2CH_2O)_nH$, wherein, for example, n is about 1–200, e.g., 1–10, or 1 to 5, or primary or secondary amines having two hydroxyl groups. Core compounds also may be high molecular weight polyethylene oxide molecules as disclosed herein.

The following are exemplary syntheses of valency platform molecules which include high molecular weight polyethylene oxide groups, and conjugates thereof. These examples involve the preparation of a polyethylene oxide-containing platform intermediate with amino groups at the temini. These amino groups are derivatized with appropriate reactive groups for conjugation with biologically active molecules.

FIG. 1 shows how a tetrameric platform is synthesized with the terminal amino groups protected with Cbz and an Fmoc-protected amino group in the core. Compound 1 is obtained as described in U.S. Pat. No. 5,552,391. The Fmoc group is removed and replaced with a methoxy-PEG chain. Removal of the Cbz groups yields the free tetra-amine, compound 6, which is converted to the tetra-chloroacetyl derivative, 7. Compound 7 can be reacted with any thiol containing molecule to form a tetavalent conjugate compound 8. In FIG. 1, n is, for example, greater than 500, e.g., 500–800 or 500–1000.

Figure 2:
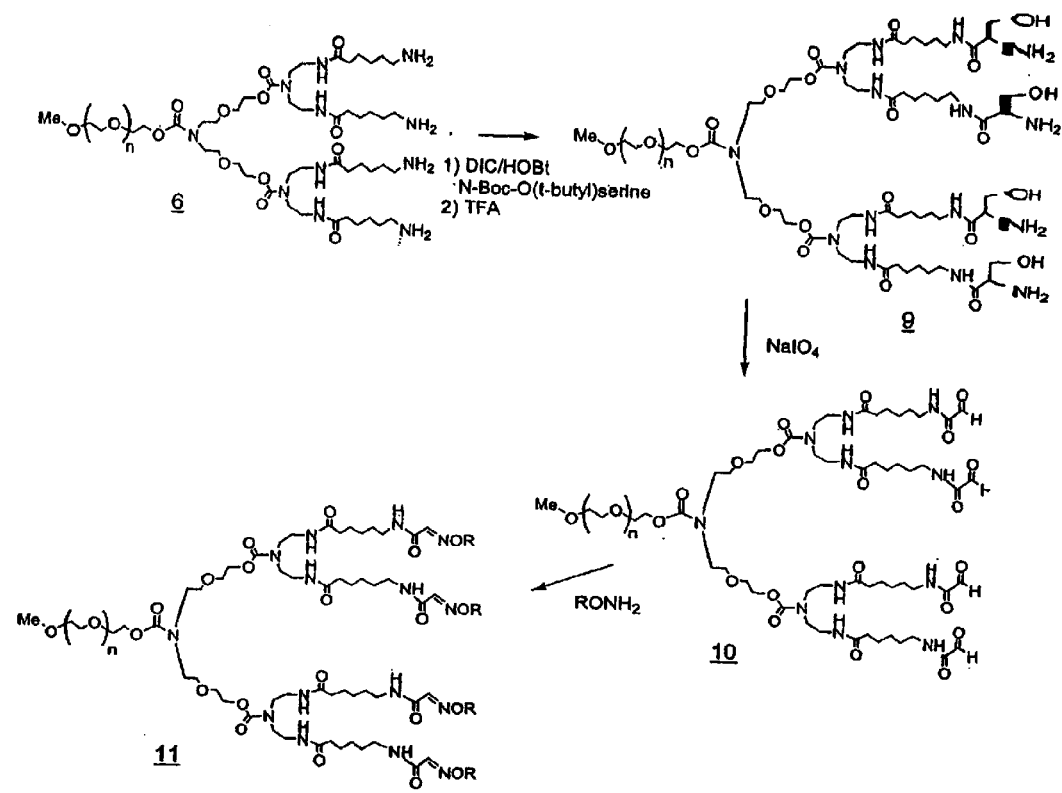

FIG. 2 shows how the tetra-amine, 6, can be modified with serine to give compound 9. The serines of compound 9 undergo oxidative cleavage with periodate to provide terminal aldehyde groups which can react with biologically active molecules containing aminooxy groups, or other groups which form stable imines (hydrazides, semicarbazides, carbazides, etc.), to form oxime conjugates represented by 11. In FIG. 2, n is, for example, greater than 500, e.g., 500–800 or 500–1000.

Figure 3:
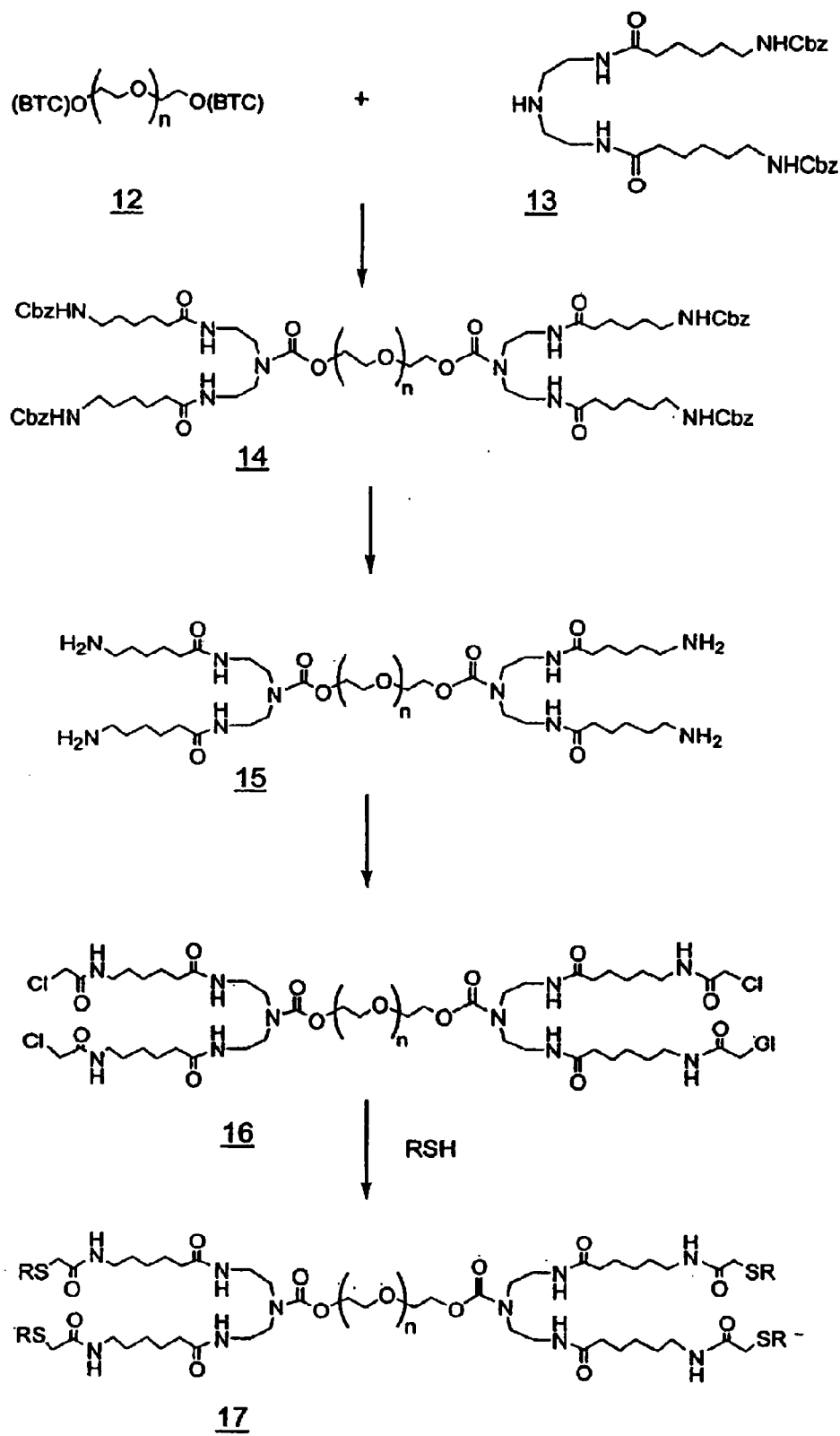

FIG. 3 demonstrates how a high molecular weight PEG platform can be prepared with PEG placed internally, as part of the core of the platform. In this embodiment, compound 14 is prepared by reacting two equivalents of compound 13 (prepared as described in U.S. Pat. No. 5,552,391) with one equivalent of compound 12 ($PEG_{20K}$-bis-BTC, Shearwater Polymers). The Cbz-protecting groups are removed by hydrogenation or acidolysis to provide the tetra-amine, compound 15. Chloroacetylation with chloroacetic anhydride yields the chloroacetylated platform, compound 16. Compound 16 is treated with a thiol containing biologically active molecule to provide 17, a tetravalent platform conjugate of the biologically active molecule. In FIG. 3, n is, for example, greater than 500, e.g., 500–800 or 500–1000.

Figure 4:
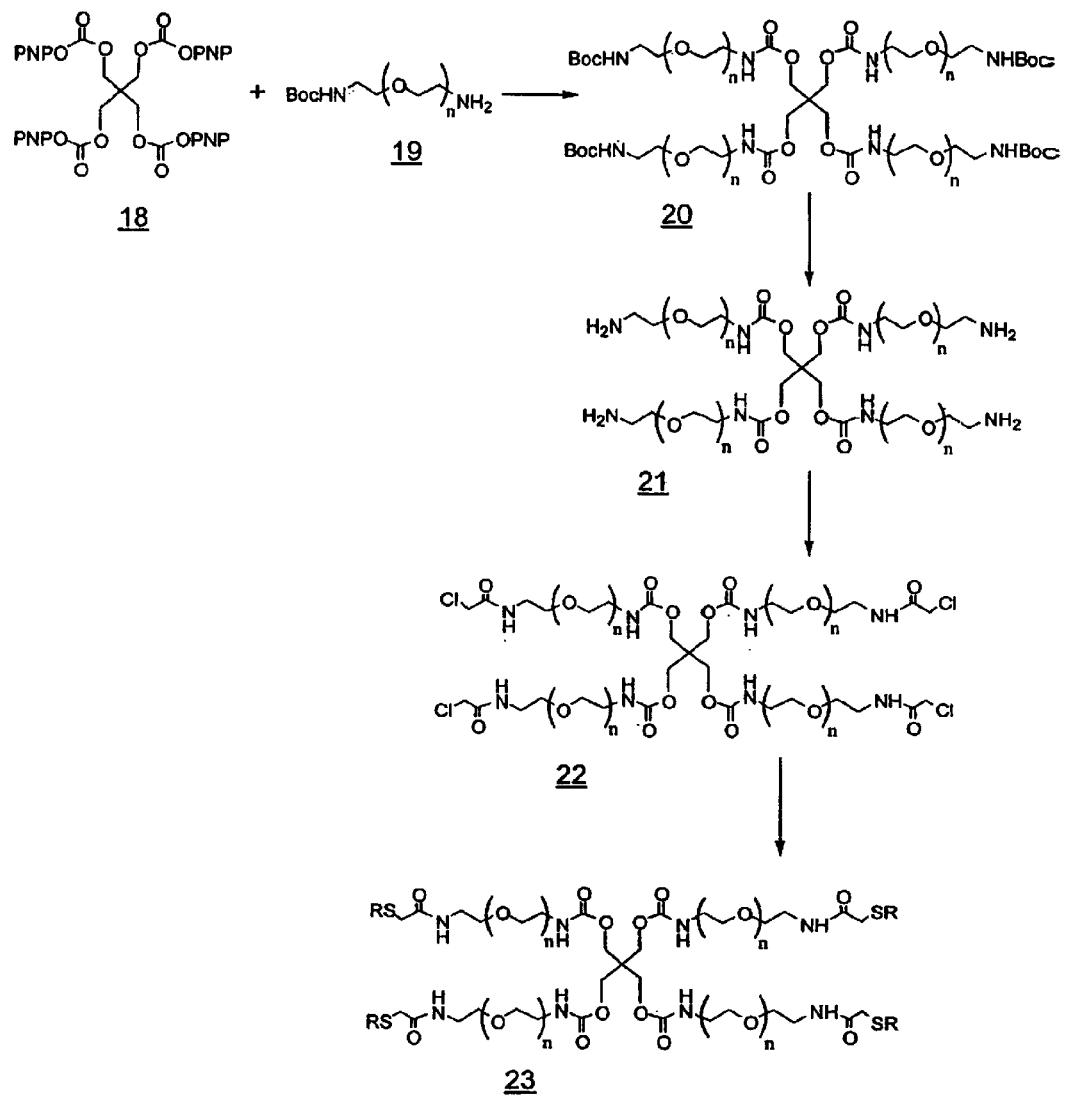

FIG. 4 demonstrates how a high molecular weight PEG platform can be prepared with PEG placed internally in the arms of the platform. "PEG" or "polyethylene glycol" or "polyethylene oxide" are used interchangably herein to refer to polymers of ethylene oxide. The Boc-protecting groups are removed from compound 20 with TFA, and the resulting tetra-amine, compound 21, is chloroacetylated with chloroacetic anhydride to yield the chloroacetylated platform, compound 22. Compound 22 is treated with a thiol containing biologically active molecule to provide 23 a tetravalent platform conjugate of the biologically active molecule. In FIG. 4, n is, for example, greater than 500, e.g., 500–800 or 500–1000.

Figure 14:
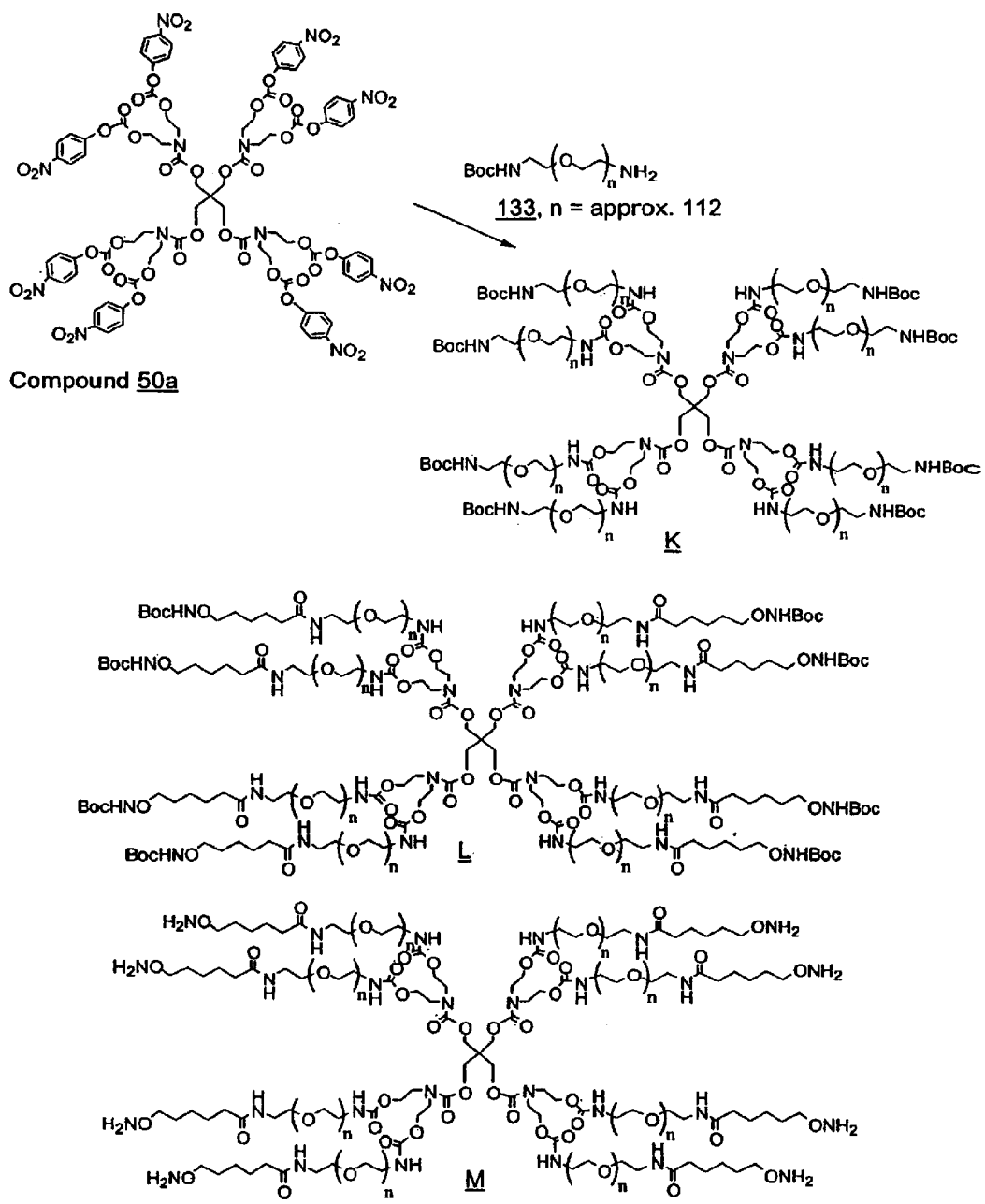
FIG. 14 shows the synthesis of an exemplary octameric bPEG platform, where n is, for example, 112, or more, e.g., 500 or more.

As shown in FIG. 14, a bPEG 8-mer platform, M is synthesized by a process wherein a octameric PNP carbonate ester (compound 50a) is reacted with compound 133 resulting in the formation of compound K. The Boc-protecting groups are removed from compound K, and the resulting octa-amine is treated with compound 106 resulting in the formation of compound L. Removal of the Boc-protecting groups from compound M results in the formation of compound M.

Figure 15:
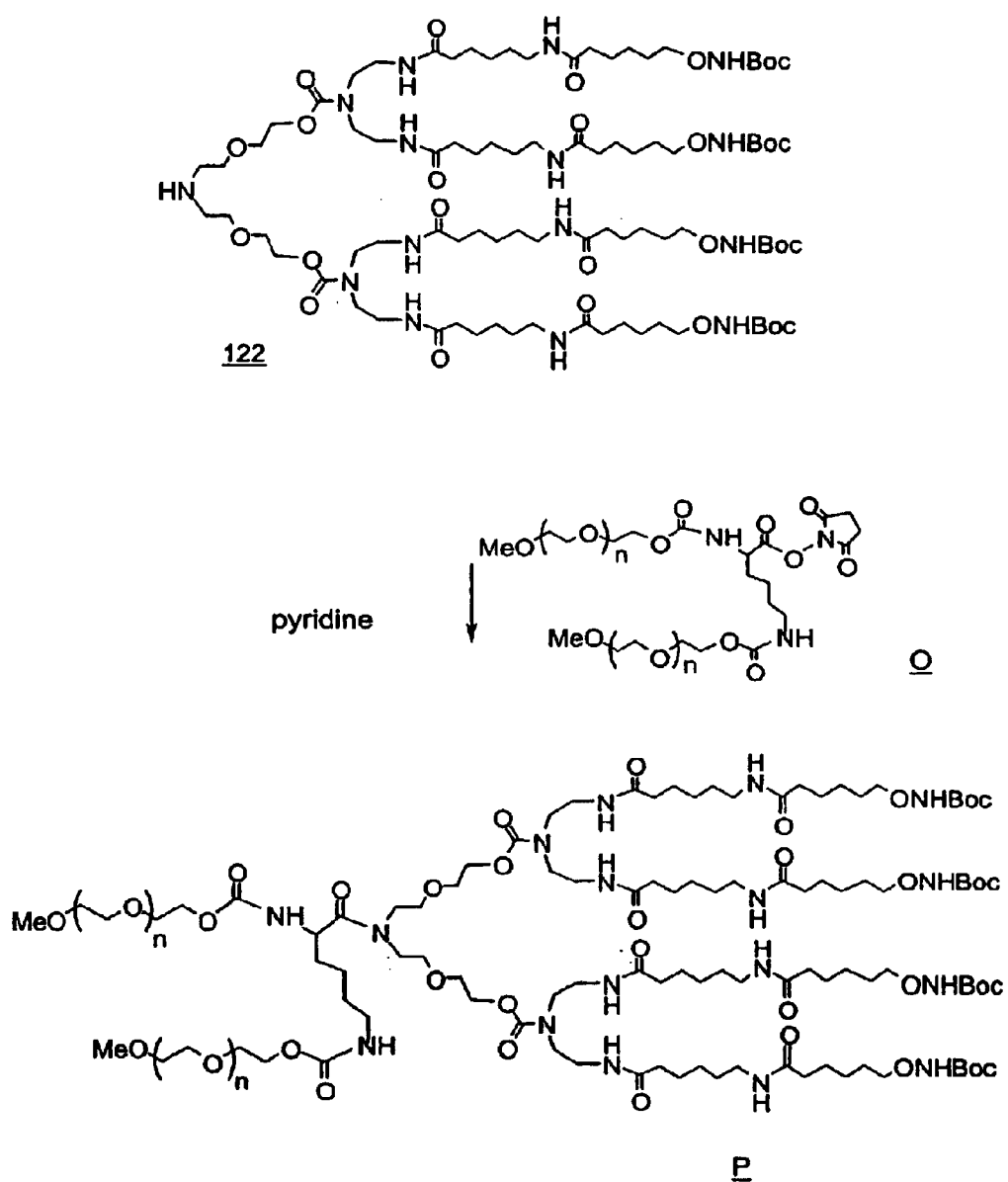
FIG. 15 shows the synthesis of a valency platform molecule comprising two polyethylene oxide groups, wherein n is, for example, 500 or more.

A tetravalent aminooxy platform with two PEG chains attached is synthesized as shown in FIG. 15 from intermediate 122 which has two PEG chains attached. Thus compound 122 is reacted with NHS ester O (Shearwater Polymers) to form platform P.

Conjugates, Methods of Preparation, and Uses Thereof

The term "biologically active molecule" is used herein to refer to molecules which have biological activity, preferably in vivo. For example, a biological activity includes binding to a target. In one embodiment, the biologically active molecule is one which interacts specifically with receptor proteins. In another embodiment, the biologically active molecule binds to an antibody which, if used in vivo, may be circulating or on a cell surface, such as a B cell surface. Biologically active molecules include one or more nucleic acids of any length (polynucleotides) including oligonucleotides; peptides; polypeptides; proteins; antibodies of any type (such as monoclonal, polyclonal, and anti-idiotype) including fragments thereof; saccharides; polysaccharides; epitopes; mimotopes; enzymes (including domains thereof); hormones; drugs; lipids; fatty acids; and mixtures thereof.

Depending on the valency of the platform, the platform molecule conjugate may include, for example, 1, 2, 3, 4, 5, 6, 7, 8, 9, 10, 11, 12 or more biologically active molecules, or e.g., 16, 18, 32, 36 or more.

Figure 5:
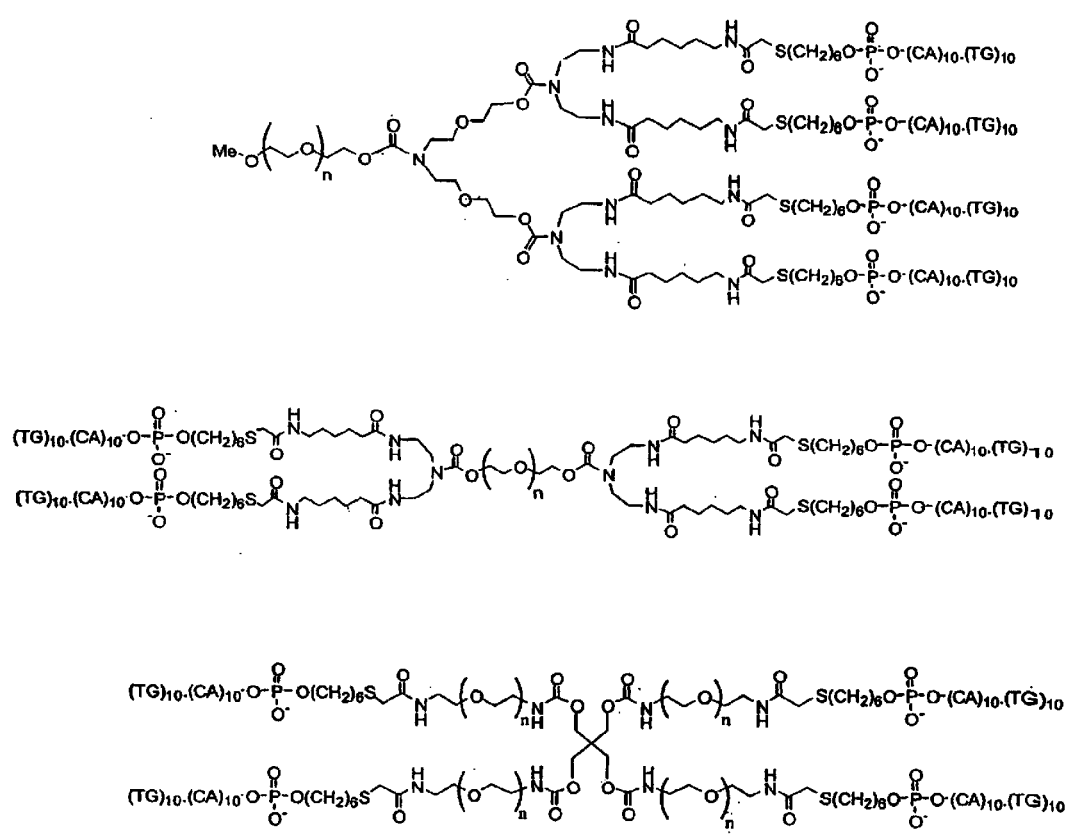
Figure 6:
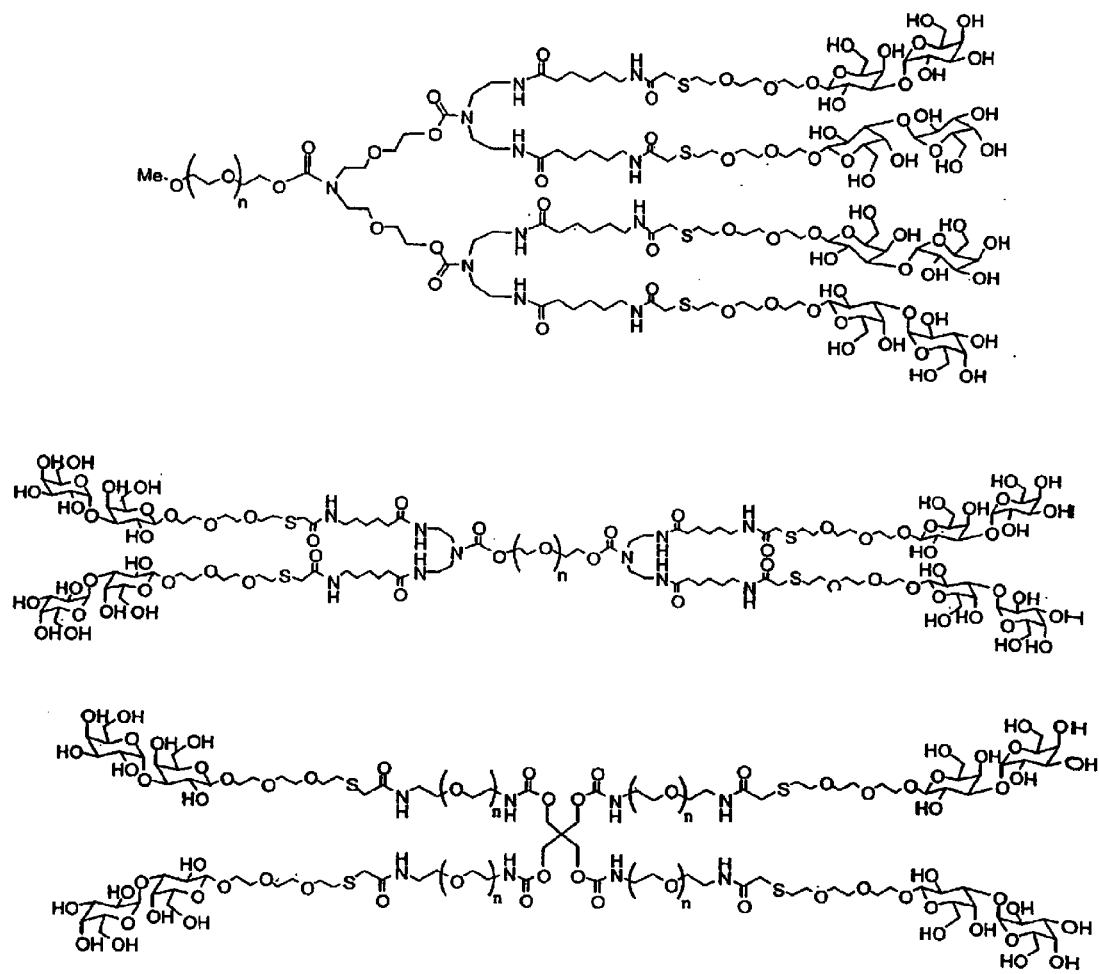

The conjugates of biologically active molecules and valency platform molecules comprising high molecular weight polyethylene oxide may be used as toleragens (which cause reduction and/or stabilization of the extent of an immune response to an immunogen) and may be used in a variety of applications for lowering levels of an antibody associated with disease and thus the treatment of antibody mediated diseases. Examples of conjugates for treating lupus, which are useful as B cell toleragens, are shown in FIG. 5. In these embodiments, the biologically active molecule generally comprises a nucleic acid which specifically binds to an anti-double stranded DNA antibody, as described, for example, in U.S. Pat. No. 5,552,391. Examples of conjugates for use in xenotransplantation, which are useful as B cell toleragens, are shown in FIG. 6 and in PCT WO 00/34296. Alternatively the conjugates disclosed herein can include other biologically active molecules such as active domain 1 $\beta_2$ GPI polypeptide sequences.

As used herein "an effective amount for treatment" refers to an amount sufficient to palliate, ameliorate, stabilize, reverse, slow or delay progression of a condition such as a disease state.

In one embodiment, the biologically active molecule comprises a domain 1 polypeptide of $\beta_2$GPI or analog thereof, as described, e.g., in U.S. Ser. Nos. 60/103,088, 09/328,199, filed Jun. 8, 1999 and PCT WO 99/64595. Exemplary structures of conjugates are shown in FIG. 7. In one embodiment, the polypeptide does not include domain 4 of $\beta_2$GPI.

The domain 1 $\beta_2$GPI polypeptide contains at least five (or more) contiguous amino acids of FIG. 19 (SEQ ID NO:2), which depicts domain 1. In one embodiment, the domain 1 $\beta_2$GPI polypeptide consists of (or, in some embodiments, consisting essentially of) the amino acid sequence shown in FIG. 19 (SEQ ID NO:2), which represents domain 1.

The domain 1 $\beta_2$GPI polypeptide preferably specifically binds to a $\beta_2$GPI-dependent antiphospholipid antibody. In some embodiments, the polypeptide comprises fragments of domain 1. In other embodiments, the polypeptide comprises a conformational epitope. In yet other embodiments, the polypeptide consists of domain 1. There further is provided a polypeptide comprising a domain 1 $\beta_2$GPI polypeptide, wherein the polypeptide lacks a (detectable) T cell epitope capable of activating T cells in an individual having $\beta_2$GPI dependent antiphospholipid antibodies.

The domain 1 $\beta_2$GPI polypeptide may, for example, range from (a) about the first cysteine to about the fourth cysteine (when determined from the N-terminus); (b) about the N terminus to about the fifth cysteine (more precisely, the last amino acid before the fifth cysteine); (c) about the first cysteine to about the fifth cysteine. In some embodiments, an additional cysteine may be added in any suitable position, to serve as a reactive group for conjugation. Accordingly, an additional cysteine (which in some embodiments is the fifth cysteine of $\beta_2$GPI) may be included in any position, particularly near or at the C terminus or N terminus. A domain 1 $\beta_2$GPI polypeptide may also comprise (or consist of, or consist essentially of) any of the following: (a) amino acid 1 to amino acid 59 of SEQ ID NO:2; (b) amino acid 2 to amino acid 60 of SEQ ID NO:2; (c) amino acid 2 to amino acid 63 of SEQ ID NO:2; (d) about amino acid 1 to about amino acid 60 of SEQ ID NO:2; (e) amino acid 1 to amino acid 61 of SEQ ID NO:2; and (f) amino acid 1 to amino acid 62 of SEQ ID NO:2. Domain 1 $\beta_2$GPI polypeptides which contain the fifth cysteine are particularly convenient for conjugation.

The domain 1 $\beta_2$GPI polypeptide specifically binds to a $\beta_2$GPI-dependent antiphospholipid antibody. The domain 1 $\beta_2$GPI polypeptide need only bind to one $\beta_2$GPI-dependent antiphospholipid antibody, although it may be desirable (for example, in the detection context), for the domain 1 $\beta_2$GPI polypeptide to bind to more than one $\beta_2$GPI-dependent antiphospholipid antibody.

The size of a domain 1 $\beta_2$GPI polypeptide may vary widely, as long as the requisite functionality (based on specific binding to a $\beta_2$GPI-dependent antiphospholipid antibody is met For example, the length sufficient to effect specific binding to a $\beta_2$GPI-dependent antiphospholipid antibody could be as small as, for example, a 5-mer amino acid sequence. In some embodiments, the domain 1 $\beta_2$GPI polypeptide is less than about 350 amino acids in length; less than about 250 amino acids in length; less than about 150 amino acids in length, less than about 100 amino acids in length; less than about 50 amino acids in length; less than about 25 amino acids in length; less than about 15 amino acids in length; or less than about 10 amino acids in length.

It is also understood that certain sequence variations may be introduced into a domain 1 $\beta_2$GPI polypeptide which may preserve or enhance its reactivity. These variant and modified sequences are collectively denoted as "functionally equivalent variants", which may have the same, enhanced, or diminished binding when compared to another domain 1 $\beta_2$GPI polypeptide, and are denoted "equivalent" because they maintain the ability to specifically bind to a $\beta_2$GPI-dependent antiphospholipid antibody.

The domain 1 conjugates can be used in methods for detection of a $\beta_2$GPI-dependent antiphospholipid antibody (or an antibody that specifically binds to a domain 1 $\beta_2$GPI polypeptide) in a sample by contacting antibody in the sample with the conjugate under conditions that permit the formation of a stable antigen-antibody complex; and detecting stable complex formed if any. The conjugates also can be used in methods of inducing tolerance in an individual which comprise administering an effective amount of a conjugate to an individual, particularly a conjugate comprising a domain 1 $\beta_2$GPI polypeptide(s) that lacks a T cell epitope, wherein an effective amount is an amount sufficient to induce tolerance. The compositions may be used, for example, in the treatment of antibody mediated thrombosis.

In another embodiment, there is provided a conjugate of a valency platform molecule and at least one αGal epitope or analog thereof that specifically binds to an anti-αGal antibody. In another aspect, a method of reducing circulating levels of anti-αGal antibodies in an individual is provided comprising administering an effective amount of the conjugate to the individual, wherein an effective amount is an amount sufficient to reduce the circulating levels of anti-αGal antibodies, or to neutralize circulating levels of anti-αGal antibodies. In another aspect, a method of inducing immunological tolerance (generally to a xenotransplantation antigen, more specifically to αGal), is provided, the method comprising administering an effective amount of the conjugate comprising the αGal epitope or analog thereof. The conjugates also can be used to detect the presence and/or amount of anti-αGal antibody in a biological sample. Methods of performing a xenotransplantation in an individual also are provided, comprising administering a conjugate to the individual; and introducing xenotissue to the individual. In another aspect, methods of suppressing rejection of a transplanted tissue are provided comprising administering the conjugate to the individual in an amount sufficient to suppress rejection. These methods are described generally in PCT US99/29338.

The conjugates also may be used for immunotolerance treatment of lupus, optionally based on assessment of initial affinity of antibody from the individual (i.e., antibody associated with lupus, namely, anti double stranded DNA antibodies) and used as a basis for selecting the individual for treatment, or in methods of identifying individuals suitable (or unsuitable) for treatment based on assessing antibody affinity. Methods of treating systemic lupus erythematosus (SLE) in an individual comprise administering to the individual a conjugate comprising (a) a non-immunogenic valency platform molecule and (b) two or more polynucleotides or analogs thereof which specifically bind to an antibody from the individual which specifically binds to double stranded DNA. These methods are described generally in PCT US99/29336.

Thus, the valency platform may be covalently linked with one or more biologically active molecules to form a conjugate. Biologically active molecules include one or more nucleic acids of any length (polynucleotides) including oligonucleotides; peptides; polypeptides; proteins; antibodies of any type (such as monoclonal, polyclonal, and anti-idiotype) including fragments thereof; saccharides; polysaccharides; epitopes; mimotopes; enzymes (including domains thereof); hormones; drugs; lipids; fatty acids; and mixtures thereof.

The terms "protein", "polypeptide", and "peptide" are used interchangeably herein to refer to polymers of amino acids of any length. The polymer may be linear or branched, it may comprise modified amino acids, and it may be interrupted by non-amino acids. It also may be modified naturally or by intervention; for example, disulfide bond formation, glycosylation, myristylation, acetylation, alkylation, phosphorylation or dephosphorylation. Also included within the definition are polypeptides containing one or more analogs of an amino acid (including, for example, unnatural amino acids) as well as other modifications known in the art.

One advantage of the conjugates of valency platforms is the ability to introduce enhanced affinity of the tethered biologically active molecules for their binding partners, for example when the binding partners are associated in a cluster. The covalent attachment of plural biological molecules to the valency platform molecule provides an enhanced local concentration of the biomolecules as they are associated together for example on the platform molecule. Another advantage of the valency platforms is the ability to facilitate binding of multiple ligands, as is useful in B cell tolerance. For example, the conjugates can be used as toleragens to present multivalent epitopes to induce clustering on the surface of a B cell. Thus, for use as a toleragen, it is preferred that the conjugate includes two or more biologically active molecules, or epitopes. Another advantage of the valency platforms is the ability to include functionality on the "core" that can be independently modified to enable the preparation of conjugates which can be tailored for specific purposes.

To form a conjugate, in general a molecule comprising a reactive group such as an aminooxy group is reacted with a second molecule comprising a reactive group such as a carbonyl group, e.g., an aldehyde or ketone, to form, for example, an oxime conjugate.

In one embodiment, a method of preparing chemically defined multivalent conjugates of native polypeptides or proteins with multivalent preferably non-immunogenic valency platform molecules comprising aminooxy groups is provided, wherein, if needed, the polypeptide is selectively modified to generate an aldehyde or ketone moiety at a specific position on the polypeptide. The polypeptide then is reacted with the multivalent valency platform molecule which contains aminooxy groups to form one or more oxime linkages between the platform and the polypeptide. Amines, for example at the N-terminus, of virtually any polypeptide or other molecule can be converted to an aldehyde or a ketone by a reaction which is known in the art as a transamination reaction.

Another way to generate an glyoxyl group at the N-terminus is to oxidize an N-terminal serine or threonine with sodium periodate. This oxidation cleaves the carbon-carbon bond between the hydroxyl and amino groups of the N-terminal serine or threonine providing a glyoxyl group. Thus in one embodiment, polypeptides can be site specifically modified by forming a ketone or aldehyde at the N-terminus. Synthetic polypeptides and other drugs or biologically active molecules can be modified similarly to include aldehydes or ketones which can be used to form oxime linkages.

Multivalent platforms containing aminooxy reactive groups permit covalent attachment of the selectively modified polypeptides to the platforms. The aminooxy groups may be, e.g., aminooxyacetyl groups or aminooxyalkyl groups. In one preferred embodiment, the aminooxy groups in the platform molecule are aminooxyalkyl groups, such as —$CH_2CH_2ONH_2$.

Attachment of biomolecules with aldehyde or ketone functionality to aminooxy platforms via oxime bond formation can be implemented. Transaminated polypeptides, or polypeptides otherwise modified with aldehyde or ketone groups can be reacted with aminooxy platforms In one embodiment, transaminated Domain 1 is attached to tetravalent platforms by treating the platforms with the glyoxyl-polypeptide in acidic aqueous solution. A preferred acidic condition is 100 mM pH 4.6 sodium acetate. In the case of making a tetravalent Domain 1 conjugate, an excess of four equivalents, for example six equivalents, of transaminated Domain 1 is used.

The conjugates of FIG. 5 are prepared as described for compound 20-II in FIG. 6B of U.S. Pat. No. 5,552,391. The appropriate haloacetylated platform 7, 17, or 23 is treated with oligonucleotide with thiol linker at the 5'-end (HS($CH_2$)$_6$OPO$_3^-$(CA)$_{10}$), prepared as described in Example 5 of U.S. Pat. No. 5,552,391. The resulting oligonucleotide conjugate is annealed with a complimentary strand ((TG)$_{10}$) to provide the corresponding tetrameric double-stranded oligonucleotide conjugate. In FIG. 5, n is, for example, greater than 500, e.g., 500–800 or 500–1000.

The conjugates of FIG. 6 are prepared as described for the conjugates of FIG. 5 using 2-[2-(2-thioethoxy)ethoxy]ethyl 3-O-(α-D-galactopyranosyl)-β-D-galactopyranoside (described in PCT US99/29338) instead of an oligonucleotide with thiol linker at the 5'-end. Thus the appropriate haloacetylated platform 7, 17, or 23 is treated with 2-[2-(2-thioethoxy)ethoxy]ethyl 3-O-(α-D-galactopyranosyl)-β-D-galactopyranoside to provide the corresponding α-1,3-digal conjugate. In FIG. 6, n is, for example, greater than 500, e.g., 500–800 or 500–1000.

The disclosures of all publications, patents, patent applications and published patent applications referred to herein by an identifying citation are hereby incorporated herein by reference in their entirety.

The invention will be further understood by the following nonlimiting examples.

EXAMPLES

In the following examples, the following abbreviations are used: DCC, 1,3-dicyclohexylcarbodiimide; DIC, 1,3-diisopropylcarbodiimide; DBU, 1,8-diazabicyclo[5.4.0]undec-7-ene; NHS, N-hydroxysuccinimide; HOBt, 1-hydroxybenzotriazole; DMF, dimethylformamide.

Example 1

Transamination of a Domain 1 Polypeptide

Synthesis of Transaminated Domain 1 (TA/D1): The synthesis is shown in FIG. 20. Water and sodium acetate buffer is sparged with helium before use. A Domain 1 β2GPI polypeptide having the sequence of amino acids 1 to 63 of SEQ ID NO.:2 shown in FIG. 19 is used, which is described in U.S. Provisional Appl. Ser. No. 60/103,088, filed Jun. 9, 1998; U.S. Ser. No. 09/328,199, filed Jun. 8, 1999; and PCT WO 99/64595. Domain 1 has an N-terminal glycine. The Domain 1 polypeptide (10.55 mg, 1.49 μmol) is dissolved in 0.5 mL of $H_2O$ in a polypropylene tube, and 4.0 mL of 2 M pH 5.5 NaOAc buffer is added. A solution of 3.73 mg (14.9 μmol) of $CuSO_4$ in 0.5 mL of $H_2O$ is added to the mixture, followed by a solution of 2.75 mg (29.9 μmol) of glyoxylic acid in 0.5 mL of 2 M pH 5.5 NaOAc buffer. The mixture is kept under nitrogen atmosphere and agitated gently for 18 h at which time the reaction appears complete by analytical HPLC using a 4.6 mm×250 mm, 300 Å, 5 μm, diphenyl column (Vydac, Hesperia, Calif.) with detection at 280 nm (1 mL/min; gradient 25%–45% B, 0–20 min, A=0.1% TFA/$H_2O$, B=0.1% TFA/$CH_3CN$). Approximate retention times are as follows: D1, 13.2 min; TA/D1, 13.7 min; oxidized TA/D1, 13.4 min). The mixture is diluted to a volume of 20 mL with $H_2O$, filtered, and purified by HPLC (22.4 mm×250 mm, 300 Å, 10 µm, diphenyl column (Vydac) (12 mL/min; gradient 25%–40% B, 0–40 min, A=0.1% $TFA/H_2O$, B=0.1% $TFA/CH_3CN$). Fractions containing pure TA/D1, as evidenced by analytical HPLC, are pooled and lyophilized to provide 5.0 mg (48%) of TA/D1. The reaction converts the N-terminal glycine to an N-terminal glyoxyl in TA D1, thus the D1 portion has the sequence of amino acids 2 to 63 of SEQ ID NO.:2 (see FIG. 20).

Example 2

Synthesis of Compound 125

Compound 115: To a solution of 8.00 g (13.4 mmol) of compound 13 (prepared as described in U.S. Pat. No. 5,552,391) in 80 mL of anhydrous DMF was added 4.00 g (16.1 mmol) of N-(benzyloxycarbonyloxy)succinimide (Aldrich Chemical Co.). The mixture was stirred for 2 hours under nitrogen at room temperature, at which time it was poured into 600 mL of ice water and extracted with four 100 mL portions of $CH_2Cl_2$. The combined $CH_2Cl_2$ layers were washed with 100 mL of $H_2O$, dried ($Na_2SO_4$), filtered, and concentrated. Concentration from heptane helped to solidify the crude product. Recrystallization from EtOAc gave compound 115 as a white solid: $^1H$ NMR($CDCl_3$) δ 1.26 (m, 4H), 1.43–1.62 (m, 8H), 2.05 (m, 4H), 3.16 (q, 4H), 3.40 (brd s, 8H), 4.98 (s, 2H) overlapped with 5.08 (s, 4H) and 5.11 (s, 2H), 6.31 (s, 1H), 6.44 (s, 1H), 7.26–7.38 (m, 15H).

Synthesis of triamine, compound 116: A solution of 9.0 g (12.3 mmol) of compound 115 in 18 mL of cyclohexane and 36 mL of anhydrous ethanol was deoxygenated by bubbling $N_2$ gas through it. To the solution was added 1.80 g of 10% Pd/C, and the mixture was heated at reflux for 3 hours. When cool, the mixture was filtered through Celite® using MeOH to rinse. The filtrate was concentrated, and the concentrate was concentrated from $CH_2Cl_2$ to provide 4.20 g (87%) of compound 116 as an off white solid.

Synthesis of compound 117: To a solution of 5.39 g (21.8 mmol) of compound 105 in 10 mL of anhydrous acetonitrile was added 3.02 g (23.9 mmol) of CDI (carbonyldiimidazole), and the mixture was stirred for 1.5 hours under nitrogen atmosphere. The resulting solution was added to a solution of 4.20 g (10.7 mmol) of compound 116 in 15 mL of anhydrous DMF, and the mixture was stirred for 2 hours and poured into 500 mL of ice water. The resulting mixture was extracted with four 100 mL portions of $CH_2Cl_2$. The combined $CH_2Cl_2$ layers were washed with 100 mL of $H_2O$, dried ($Na_2SO_4$), filtered, and concentrated. The resulting semisolid residue was crystallized from 10% isopropyl alcohol/EtOAc to provide 4.0 g (44%) of 117 as a white solid: $^1H$ NMR $CDCl_3$ (δ) 1.35 (m, 4H), 1.42 (m, 4H), 1.49 (s, 18H), 1.63 (m, 16H), 2.01 (brd s, 1H), 2.20 (t, 4H), 3.23 (m, 4H), 3.34 (m, 4H), 3.85 (t, 4H), 6.34 (t, 2H), 6.70 (t, 2H), 7.98 (brd s, 1H).

Compound 119: To a solution of 3.65 g (14.11 mmol) of 9-fluorenylmethylchloroformate (Fmoc-Cl) in 15 mL of dioxane was added a solution of 3.00 g (15.5 mmol) of compound 118 (Bondunov et al., J. Org. Chem. 1995, Vol. 60, pp. 6097–6102) in 15 mL of dioxane followed by a solution of 1.95 g (14.11 mmol) of potassium carbonate in 30 mL of $H_2O$. The mixture was stirred for 18 hours at room temperature and concentrated. The resulting oil was partitioned between 50 mL of 1 N NaOH solution and three 150 mL portions of $CH_2Cl_2$. The combined $CH_2Cl_2$ layers were dried ($MgSO_4$), filtered, and concentrated to a yellow oil. Purification by silica gel chromatography (step gradient; 90/10 EtOAc/AcOH to 90/10/1 EtOAc/AcOH/MeOH) to give 3.85 g (66%) of 119 as a viscous oil: $^1H$ NMR $CDCl_3$ (δ) 3.26 (m, 4H), 3.39 (m, 2H), 3.49 (m, 2H), 3.59 (m, 2H), 3.65 (m, 4H), 3.69 (m, 2H), 4.25 (t, 1H), 4.60 (d, 2H), 7.35 (t, 2H), 7.41 (t, 2H), 7.59 (d, 2H), 7.78 (d, 2H).

Compound 120: To a solution of 3.77 g (9.08 mmol) of compound 119 and 7.32 g (36.3 mmol) of 4-nitrophenylchlorofornate in 50 mL of $CH_2Cl_2$ at 0° C. was added 5.88 mL (5.75 g, 72.6 mmol) of pyridine. The mixture was stirred at room temperature under nitrogen atmosphere for 72 hours, and the mixture was partitioned between 200 mL of $CH_2Cl_2$ and four 100 ml portions of 10% aqueous sodium bicarbonate solution. The $CH_2Cl_2$ layer was washed successively with 100 mL of $H_2O$, 100 mL of 1 N HCl, then 100 mL of brine. The solution was dried ($MgSO_4$), filtered, and concentrated to yield an orange oil. Purification by silica gel chromatography (15/50/35/1 $EtOAc/CH_2Cl_2$/hexane/ AcOH) to provide 2.67 g (39%) of compound 120 as a yellow gum: $^1H$ NMR ($CDCl_3$) δ 3.32 (m, 4H), 3.52 (m, 2H). 3.60 (m, 4H), 3.74 (m, 2H), 4.23 (t, 1H), 4.38 (m, 2H), 4.41 (m, 2H), 4.57 (d, 2H), 7.37 (m, 8H), 7.59 (d, 2H), 7.78 (d, 2H), 8.26 (overlapping d, 4H); mass spectrum (ESI) (M+H) calculated for $C_{37}H_{36}N_3O_{14}$: 746. Found 746.

Compound 121: To a solution of 482 mg (0.612 mmol) of compound 117 in 5 mL of $CH_2Cl_2$ was added 182 mg (0.245 mmol) of compound 120 followed by 171 µL (124 mg, 1.22 mmol) of $Et_3N$ and 26 mg (0.490 mmol) of HOBt. The mixture was stirred at room temperature until the reaction was complete as judged by TLC (1/9 $MeOH/CH_2Cl_2$). The mixture was partitioned between 300 mL of $CH_2Cl_2$ and three 50 mL portions of 1 N HCl. The $CH_2Cl_2$ layer was washed with brine, dried ($MgSO_4$), filtered, and concentrated to a yellow oil. Purification by silica gel chromatography (multiple step gradient; 5/1/94 to 10/1/89 to 15/1/84 to 20/1/79 $MeOH/HOAc/CH_2Cl_2$) to provide 317 mg (63%) of compound 121 as a sticky white solid: $^1H$ NMR ($CD_3OD$) δ 1.34 (m, 16H), 1.43 (m, 8H), 1.48 (s, 36H), 1.64 (m, 24H), 2.20 (m, 16H), 3.19 (m, 12H), 3.25–3.52 (m, 18H), 3.55 (m, 2H), 3.79 (t, 8H), 4.16 (m, 4H), 4.28 (t, 1H), 4.59 (d, 2H), 7.33 (t, 2H), 7.41 (t, 2H), 7.60 (d, 2H), 7.84 (d, 2H); $^{13}C$ NMR ($CD_3OD$) δ 14.6, 23.8, 26.7, 26.7, 26.9, 27.7, 28.8, 28.9, 30.3, 37.1, 38.8, 39.1, 40.3, 65.8, 66.0, 68.1, 70.2, 70.3, 77.3, 82.0, 121.2, 126.0, 128.4, 129.0, 142.9, 145.6, 157.9, 158.2, 159.2, 176.1, 176.3; mass spectrum (ESI) (M+2Na)/2 calculated for $C_{101}H_{171}Na_2N_{15}O_{28}$: 1044. Found 1044.

Compound 122: To a solution of 163 mg (79.8 mmol) of compound 121 in 2.4 mL of DMF was added 600 µL of diethylamine. The mixture was stirred for 3 hours and concentrated. Purification by silica gel chromatography (multi-step gradient; 10/1/89 to 12.5/6/86.5/ to 15/1/84 MeOH/con $NH_4OH/CH_2Cl_2$) gave 127 mg (81%) of compound 122 as a glassy gum: $^1H$ NMR ($CD_3OD$) δ 1.38 (m, 16H), 1.48 (m, 44H), 1.65 (m, 24H), 2.20 (t, 16H), 2.83 (t, 4H), 3.17 (t, 8H), 3.38 (m, 16H), 3.63 (t, 4H), 3.69 (t, 4H), 3.78 (t, 4H), 4.21 (m, 4H); $^{13}C$ NMR ($CD_3OD$) δ 26.7, 27.0, 27.8, 28.8, 28.9, 30.3, 37.1, 38.8, 39.1, 40.3, 49.9, 66.0, 70.4, 70.9, 77.3, 82.0, 158.2, 159.2, 176.1, 176.3; mass spectrum (ESI) (M+H) calculated for $C_{86}H_{162}N_{15}O_{26}$: 1821. Found 1821.

Compound 124b: To a solution of 20 mg (11.0 µmol) of compound 122 in 5 mL of DMF was added 103 mg (8.8 µmol) of methoxypolyethyleneglycol benzotriazolylcarbonate of molecular weight 11,690 g/mol ($mPEG_{12K}$-BTC, compound 123b, Shearwater Polymers) followed by 5 µL (3.6 mg, 35.9 µmol) of $Et_3N$. The mixture was stirred at room temperature for 18 hours and concentrated. The residue was purified by silica gel chromatography (multi-step gradient; 5/95 to 15/85 to 20/80 MeOH/CH$_2$Cl$_2$) to provide 109 mg of compound 124b as a waxy off white solid: $^1$H NMR (CDCl$_3$) δ 1.37 (m, 16H), 1.49 (m, 44H), 1.65 (m, 24H), 2.20 (t, 16H), 3.20 (q, 8H), 3.36 (m, 16H), 3.61 (m, 4H), 3.68 (m, approximately 1056H), 3.84 (t, 8H), 3.91 (m, 4H), 4.23 (m, 4H).

Compound 124a: This compound was prepared using essentially the same procedure used for the preparation of compound 124b; however, methoxypolyethyleneglycol benzotriazolylcarbonate of molecular weight 5,215 g/mol (mPEG$_{5K}$-BTC, compound 123a, Shearwater Polymers) was used: $^1$H NMR (4:1 CDCL$_3$/CD$_3$OD) δ 1.37 (m, 16H), 1.49 (m, 44H), 1.65 (m, 24H), 2.20 (t, 16H), 3.20 (q, 8H), 3.36 (m, 16H), 3.61 (m, 4H), 3.68 (m, approximately 468H), 3.84 (t, 8H), 3.91 (m, 4H), 4.23 (m, 4H).

Compound 124c: This compound was prepared using essentially the same procedure used for the preparation of compound 124b; however, methoxypolyethyleneglycol benzotriazolylcarbonate of molecular weight 22, 334 g/mol (mPEG$_{20K}$-BTC, compound 123c, Shearwater Polymers) was used: $^1$H NMR (5:1 CDCl$_3$/CD$_3$OD) δ 1.37 (m, 16H), 1.49 (m, 44H), 1.65 (m, 24H), 2.20 (t, 16H), 3.20 (q, 8H), 3.36 (m, 16H), 3.61 (m, 4H), 3.68 (m, approximately 2024H), 3.84 (t, 8H), 3.91 (m, 4H), 4.23 (m, 4H).

Analogously, the synthesis can be conducted with mPEG-BTC of the desired molecular weight, for example, 23,000, 25,000, 40,000 or more. Thus, in FIG. 9, n is optionally greater than 500, for example, 550, 600, 800 or more.

Figure 9:
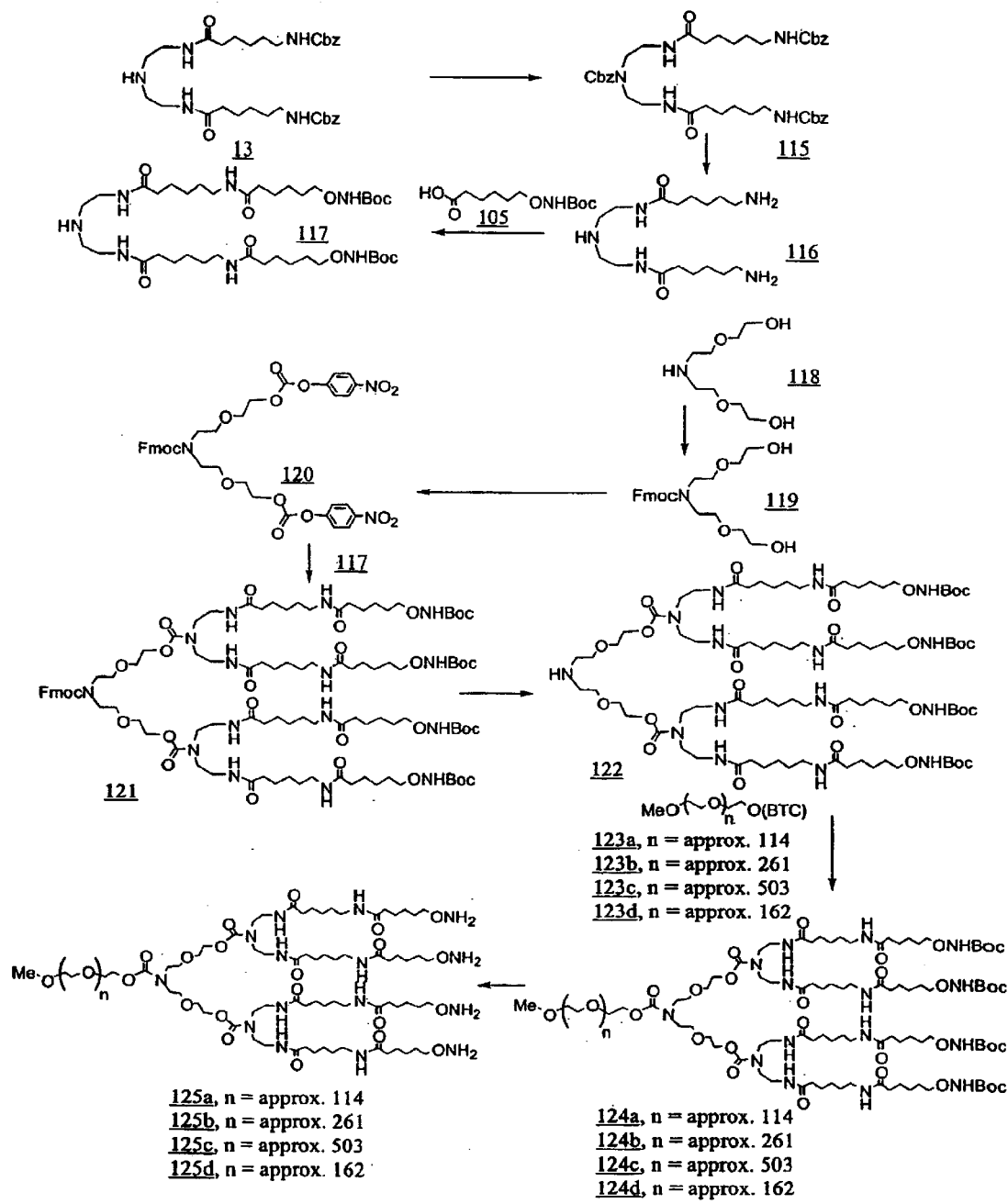

Compound 125b: The Boc-protecting groups are removed from compounds 124a–c in a manner essentially similar to that described for the preparation of compound 16 to provide compounds 125a–c, The reaction scheme is shown in FIG. 9.

Example 3

Synthesis of Compound 129

Compound 126: To a solution of 14 mg (18.6 μmol) of compound 120 and 29 mg (186.3 μmol) of HOBT in 5 mL of anhydrous DMF was added 56 μL (38 mg, 373 μmol) of Et$_3$N. The mixture was stirred for 1 hour and a solution of 85 mg (46.6 μmol) of compound 122 in 1 mL of DMF was added. The mixture was stirred at room temperature for 5 hours and partitioned between 150 mL of CH$_2$Cl$_2$ and 50 mL of 1 N HCl. The CH$_2$Cl$_2$ layer was washed with brine, dried (MgSO$_4$), filtered, and concentrated. Purification by silica gel chromatography provided 34 mg (44%) of compound 126 as a waxy white solid: $^1$H NMR (CD$_3$OD) δ 1.37 (m, 32H), 1.49 (m overlapping s at 1.48, 88H) 1.62 (m, 48H), 2.20 (t, 32H), 3.18 (t, 16H), 3.36 (m, 32H), 3.50 (m, 12H), 3.64 (m, 24H), 3.79 (t, 16H) 4.17 (m, 12H), 4.29 (t, 1H), 4.60 (d, 2H), 7.37 (t, 2H), 7.43 (t, 2H), 7.65 (d, 2H), 7.84 (d, 2H); mass spectrum (ESI) (M+3Na)/3 calculated for C$_{197}$H$_{347}$Na$_3$N$_{31}$O$_{60}$: 1393. Found 1393.

Alternative synthesis of compound 126: Pyridine (5 mL) was added to a flask charged with 136 mg (74.7 umol) of compound 122, 22.3 mg (29.9 umol) of compound 120, and 18.3 mg (119.5 umol) of hydroxybenzotniazole monohydrate (HOBt). The resulting solution was stirred for 18 hours, and the pyridine was removed by rotory evaporation under vacuum. Purification by silica gel chromatography (gradient 1/13/86 to 1/20/79 AcOH/MeOH/CH$_2$Cl$_2$) provided 104 mg (85%) of compound 126 as a white solid.

Compound 127: To a solution of 34 mg (8.27 μmol) of compound 126 in 1.6 mL of DMF was added 400 μL of diethylamine. The mixture was stirred at room temperature for 4 hours and concentrated. The concentrate was purified by silica gel chromatography (1/10/89 con NH$_4$OH/MeOH/ CH$_2$Cl$_2$) to provide 13 mg (40%) of compound 127: $^1$H NMR (CD$_3$OD) δ 1.35 (m, 32H), 1.49 (m overlapping s at 1.48, 88H), 1.63 (m, 48H), 2.19 (t, 32H), 3.08 (brd t, 4H) 3.17 (t, 16H), 3.38 (m, 36H), 3.52 (m, 8H), 3.63 (t, 8H), 3.70 (m, 12H), 3.78 (t, 16H), 4.21 (m, 12H); mass spectrum (ESI) (M+3Na)/3 calculated for C$_{182}$H$_{337}$Na$_3$N$_{31}$O$_{58}$: 1319. Found 1319.

Compound 128: To a solution of 13 mg (3.34 μmol) of compound 127 in 5 mL of pyridine was added 60 mg (2.68 μmol) of methoxypolyethyleneglycol benzotriazolylcarbonate of molecular weight 22,334 g/mol (mPEG$_{20K}$-BTC, Shearwater Polymers) followed by 5 μL (3.6 mg, 35.9 μmol) of Et$_3$N. The mixture was stirred at room temperature for 18 hours and concentrated. The residue was purified by silica gel chromatography (multi-step gradient; 10/90 to 15/85 to 20/80 MeOH/CH$_2$Cl$_2$) to provide 45 mg of compound 128 as a waxy solid: $^1$H NMR (CDCl$_3$) δ 1.30 (m, 32H), 1.50 (m overlapping s at 1.48, 88H), 1.67 (m, 48H), 2.24 (t, 32H), 3.23 (m, 16H), 3.41 (m, 32H), 3.65 (m, approximately 2024H), 3.70 (t, 24H), 3.89 (m, 16H), 4.21 (m, 12H).

Analogously, the synthesis can be conducted with mPEG-BTC of the desired molecular weight, for example, 23,000, 25,000, 40,000 or more. Thus, in FIG. 10, n is optionally greater than 500, for example, 550, 600, 800 or more.

Figure 10:
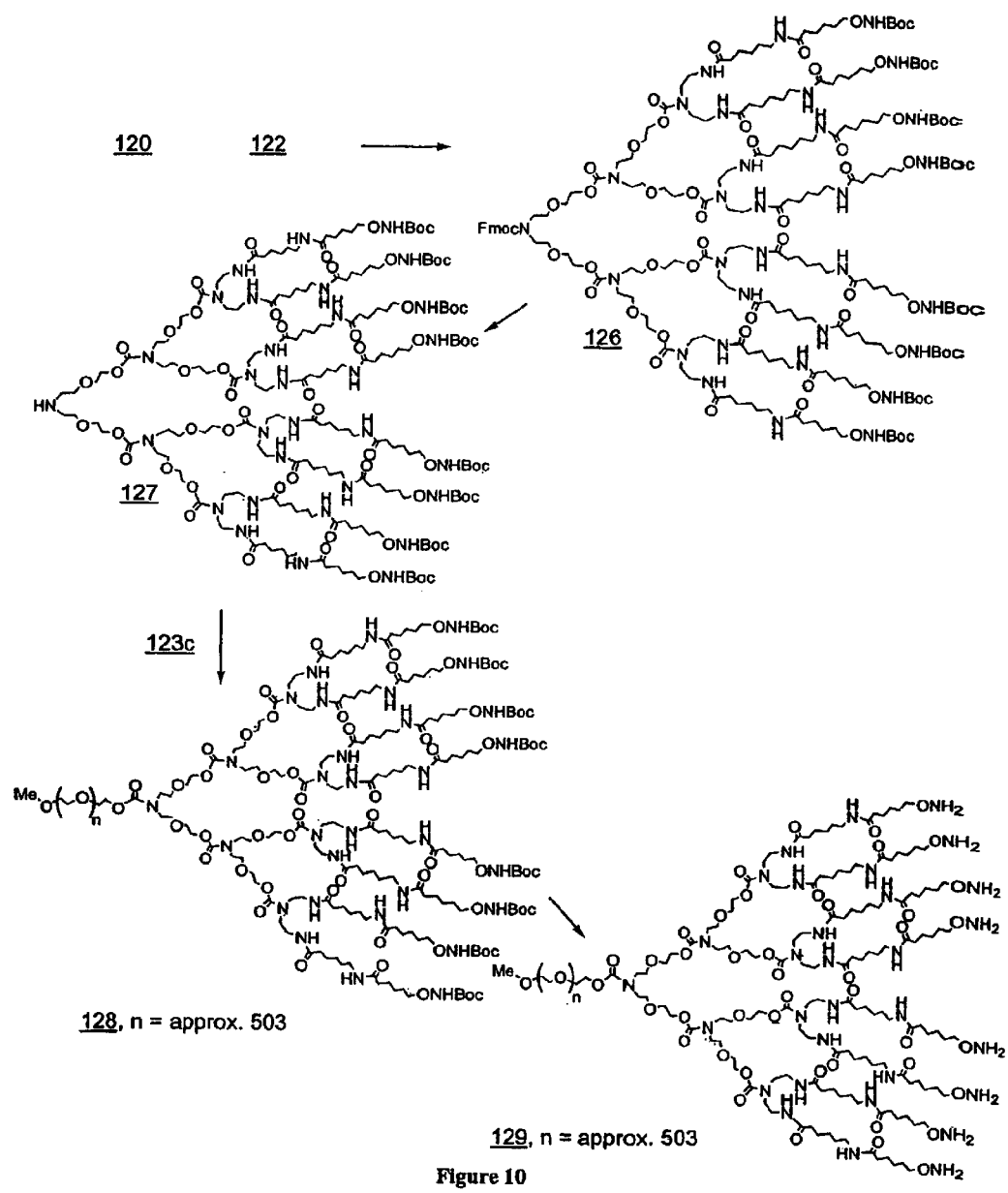

Compound 129: The Boc-protecting groups are removed from compound 128 in a manner essentially similar to that described for the preparation of compound 16 to provide compounds 129, as shown in FIG. 10.

Example 4

Synthesis of Compound 132

Compound 131: To a solution of 22 mg (27.3 μmol) of compound 117 in 5 mL of pyridine was added 236 mg (10.9 μmol) of polyethyleneglycol bis-benzotriazolylcarbonate of molecular weight 21,529 g/mol (PEG$_{20K}$-bis-BTC, compound 130, Shearwater Polymers) followed by 8 μL (5.8 mg, 57.4 μmol) of Et$_3$N. The mixture was stirred at room temperature for 18 hours and concentrated. The residue was purified by silica gel chromatography (multi-step gradient; 5/95 to 10/90 to 15/85 to 20/80 MeOH/CH$_2$Cl$_2$) to provide 242 mg (96%) of compound 131 as a white solid: $^1$H NMR (CDCl$_3$) δ 1.35 (m, 16H), 1.48 (m, 44H), 1.61 (m, 24H), 2.20 (m, 16H), 3.22 (m, 8H), 3.52–3.96 (m, approximately 2000H), 4.23 (m, 4H).

Analogously, the synthesis can be conducted with PEG-bis-BTC of the desired molecular weight, for example, 23,000, 25,000, 40,000 or more. Thus, in FIG. 11, n is optionally greater than 500, for example, 550, 600, 800 or more.

Compound 132: The Boc-protecting groups are removed from compound 131 in a manner essentially similar to that described for the preparation of compound 16 to provide compound 132.

Figure 11:
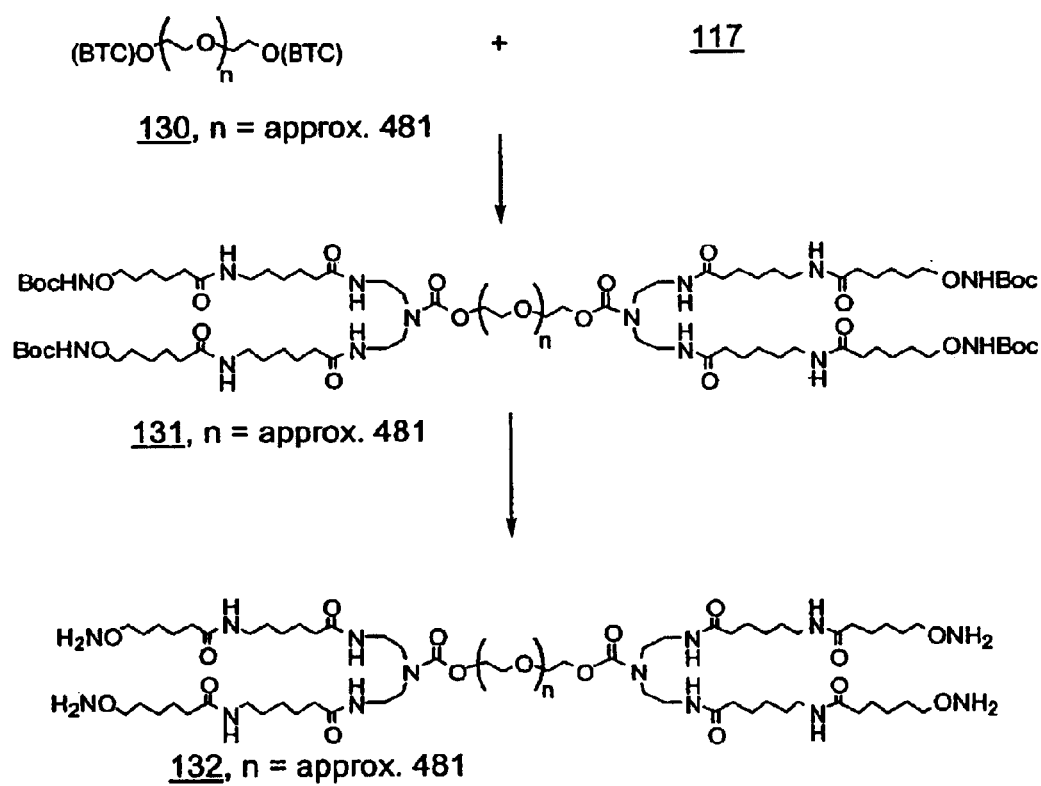

The reaction scheme is shown in FIG. 11.

Example 5

Synthesis of Compound 136

Compound 134: To a solution of 3.87 mg (4.85 μmol) of pentaerythritol tetrakis-(4-nitrophenylcarbonate ester), (prepared by reaction of pentaerythritol with paranitrophenylchloroformate to yield the tetra para-nitrophenylcarbonate compound), in 5 mL of pyridine was added 124 mg (24.2 µmol) of mono-Boc-protected diaminopolyethylene glycol of molecular weight 5094 g/mol (compound 133, BocNH—PEG$_{(5K)}$—NH$_2$, Shearwater), and 5 µL (3.63 mg, 35.9 µmol) of Et$_3$N. The mixture was stirred for 18 hours and concentrated. The residue was purified by silica gel chromatography (step gradient; 5/95 to 15/85 MeOH/CH$_2$Cl$_2$) to provide 77 mg (77%) of compound 134 as a white solid: $^1$H NMR (CDCl$_3$) δ 1.48 (s, 36H), 3.32 (m, 16H), 3.52–3.96 (m, approximately 1818H), 4.10 (m, 8H).

Analogously, the synthesis can be conducted with BocNH—PEG—NH$_2$ of the desired molecular weight, for example, 23,000, 25,000, 40,000 or more. Thus, in FIG. 12, n is optionally greater than 500, for example, 550, 600, 800 or more.

Synthesis of compound 106: To a magnetically stirred solution of 5.2 g (20.2 mmol, 1.1 eq.) of di-succinimidyl carbonate in 200 mL of acetonitrile was added 4.54 g (18.3 mmol, 1.0 eq.) of a solution of compound 105 in 100 mL of acetonitrile. Pyridine (2.67 mL, 2.61 g, 33.03 mmol, 1.8 eq.) was added, and the mixture was stirred overnight. The mixture was concentrated, and the residue was dissolved in 20 mL of dichloromethane. The organic layer was washed with two 20 mL portions of 1 N HCl and 20 mL sat. aq. NaCl. The organic layer was dried (MgSO$_4$), filtered, and concentrated to provide 5.7 g of yellow oil. A portion of this material (2.732 g) was further purified by silica gel chromatography (15/85 acetone/toluene) to give 4.38 g (68%) of compound 106 as a colorless oil. $^1$H NMR CDCl$_3$ (δ) 1.48 (s, 9H), 1.51 (m, 2H), 1.68 (p, 2H), 1.79 (p, 2H), 2.63 (t, 2H), 2.84 (br. s, 4H), 3.87 (t, 2H), 7.18 (br. s, 1H); $^{13}$C NMR CDCl$_3$ (δ) 24.32, 25.07, 25.53, 27.42, 28.16, 30.77, 76.13, 81.51, 156.89, 168.45, 169.15.

Compound 135: Compound 134 (77 mg, 3.73, µmol) was dissolved in 5 mL of trifluoroacetic acid, and the mixture was allowed to stand for three hours. The TFA was removed under a stream of N$_2$ and the residue was dissolved in 5 mL of CH$_2$Cl$_2$. To the resulting solution was added a solution of 7.72 mg (22.4 µmol) of compound 106 in 5 mL of CH$_2$Cl$_2$ followed by 35 µL (25.4 mg, 251 µmol) of Et$_3$N. (Note: The pH of the mixture should be checked and adjusted accordingly with Et$_3$N to make sure it is basic.) The mixture was stirred under nitrogen for 18 hours. The mixture was partitioned between 50 mL of CH$_2$Cl$_2$ and three 25 mL portions of 1 N HCl. The CH$_2$Cl$_2$ layer was washed with brine, dried (MgSO$_4$), filtered and concentrated. Purification by silica gel chromatography (step gradient; 5/95 to 10/90 MeOH/CH$_2$Cl$_2$) provided 42 mg (53%) of compound 135 as waxy solid: $^1$H NMR (CDCl$_3$) δ 1.40 (m, 8H), 1.48 (s, 36H), 1.66 (m, 16H), 2.18 (t, 8H), 3.32 (m, 16H), 3.38–3.89 (m, approximately 1818H), 4.10 (m, 8H), 4.97 (t, 4H), 6.43 (t, 4H), 7.47 (s, 4H).

Figure 12:
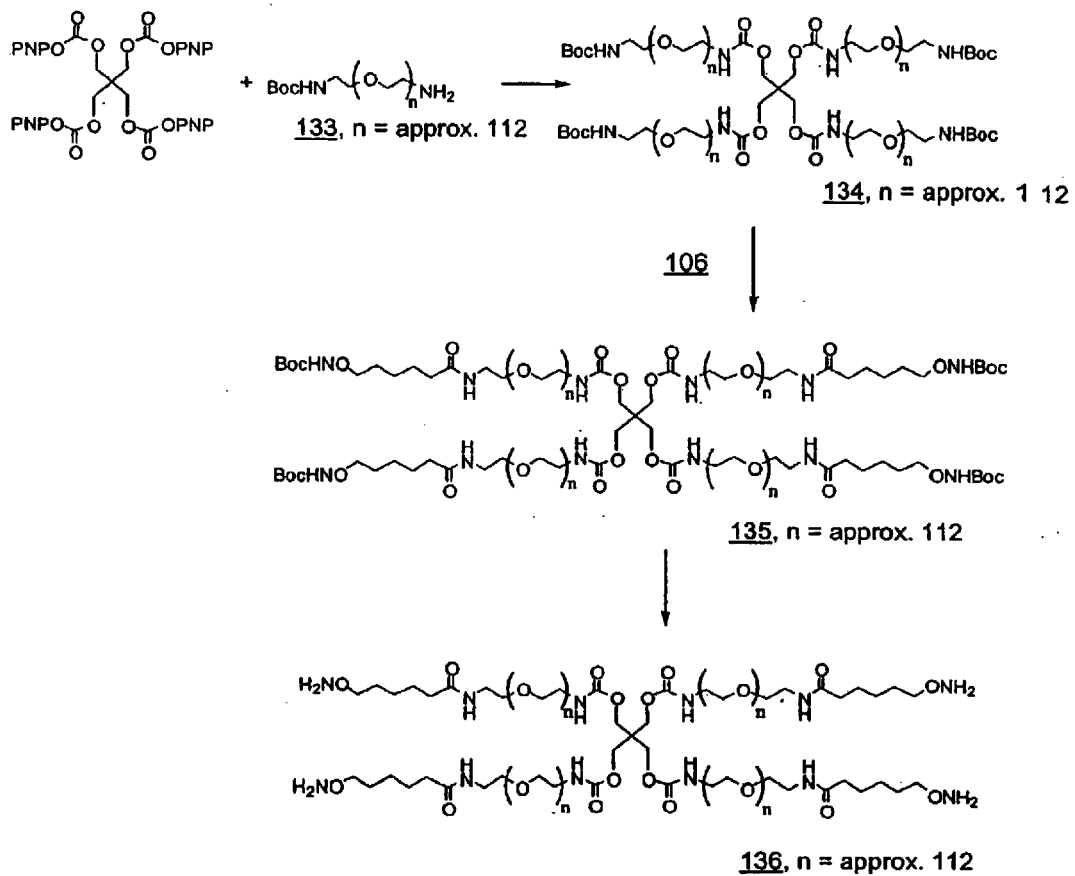

Compound 136: The Boc-protecting groups are removed from compound 135 in a manner essentially similar to that described for the preparation of compound 16 to provide compound 136, as shown in FIG. 12.

Example 6

Synthesis of Compound 143

Compound 137: To a 0° C. solution of 200 mg (1.11 mmol) of ethyl 3,5-diaminobenzoate in 5 mL of CH$_2$Cl$_2$ under nitrogen atmosphere was added 928 µL (674 mg, 6.66 mmol) of Et$_3$N. To the mixture was added dropwise a solution of 510 µL (710 mg, 3.33 mmol) of 6-bromohexanoyl chloride in 5 mL of CH$_2$Cl$_2$. The mixture was stirred at room temperature for 1.5 hours and partitioned between 50 mL of 1 N HCl and two 50 mL portions of CH$_2$Cl$_2$. The CH$_2$Cl$_2$ layers were washed with saturated sodium bicarbonate solution, dried (MgSO$_4$), filtered and concentrated. The product was purified by silica gel chromatography (6/4 hexane/EtOAc) to give 554 mg (93%) of compound 137 as an oil: $^1$H NMR (CDCl$_3$): δ1.39 (t, 3H), 1.52 (m, 4H), 1.75 (m, 4H), 1.90 (m, 4H), 2.40 (t, 4H), 3.42 (t, 4H), 4.36 (q, 2H), 7.60 (s, 2H), 7.88 (s, 2H), 8.17 (s, 1H).

Compound 138: DBU (612 µL, 623 mg, 4.01 mmol) was added to a solution of 547 mg (1.02 mmol) of compound 137 and 272 mg (2.05 mmol) of N-(tert-butyloxycarbonyl) hydroxylamine (Aldrich Chemical Co.). The mixture was stirred for 18 hours at room temperature and partitioned between 50 mL of 1 N HCl and three 50 mL portions of CH$_2$Cl$_2$. The combined CH$_2$Cl$_2$ layers were dried (MgSO$_4$), filtered, and concentrated. The product was purified by silica gel chromatography (1/1 hexane/EtOAc) to give 216 mg (33%) of compound 138 as a white solid: mp 55–60° C.; $^1$H NMR (CDCl$_3$): δ 1.38 (t, 3H), 1.48 (s, 18H; burried m, 4H), 1.60 (m, 4H), 1.73 (m, 4H), 2.40 (m, 4H), 3.86 (t, 4H), 4.36 (q, 2H), 7.41 (s, 2H), 7.90 (s, 2H), 8.06 (s, 2H), 8.11 (s, 1H); mass spectrum (ESI) (M+Na) calculated for C$_{31}$H$_{50}$NaN$_4$O$_{10}$: 661. Found 661.

Compound 139: To a solution of 205 mg (0.32 mmol) of compound 138 in 1/1 acetone/EtOH was added 256 µL (2.56 mmol) of 10 N NaOH, and the mixture was heated to 60° C. for 4 hours. When cool, the mixture was partitioned between 50 mL of 1 N HCl and four 50 mL portions of 4/1 CH$_2$Cl$_2$/MeOH. The combined organic layers were dried (MgSO$_4$), filtered, and concentrated. The product was purified by silica gel chromatography (3/97/1 MeOH/CH$_2$Cl$_2$/HOAc) to give 184 mg (94%) of compound 139 as a viscous oil: $^1$H NMR (CDCl$_3$): δ 1.38 (m, 4H), 1.42 (s, 18H), 1.60 (m, 4H), 1.70 (m, 4H), 2.38 (m, 4H), 3.80 (t, 4H), 7.77 (s, 2H), 8.00 (s, 2H), 8.11 (s, 1H), 8.91 (s, 2H); mass spectrum (ESI) (M+Na) calculated for C$_{29}$H$_{46}$NaN$_4$O$_{10}$:633. Found 633.

Compound 140: To a 0° C. solution of 164 mg (0.268 mmol) of compound 139 in 2.0 mL of dry THF was added 31 mg (0.268 mmol) of N-hydroxysuccinimide, followed by 83 mg (0.403 mmol) of DCC. The mixture was allowed to come to room temperature and stirred for 18 hours under nitrogen atmosphere, and 200 µL of HOAc was added. The mixture was stirred for another hour, diluted with approximately 5 mL of EtOAc, and allowed to stand for an hour. The resulting precipitate was removed by filtration, and the filtrate was concentrated. Purification by silica gel chromatography (3/97/ MeOH/CH$_2$Cl$_2$) provided 129 mg (68%) of compound 140 as a white solid: $^1$H NMR (CDCl$_3$): δ 1.40 (m, 4H), 1.43 (s, 18H), 1.65 (m, 4H), 1.80 (m, 4H), 2.34 (m, 4H), 2.93 (s, 4H), 3.85 (t, 4H), 7.68 (s, 2H), 7.87 (s, 2H), 8.36 (s, 1H), 8.61 (s, 2H).

Compound 142: To a solution of 60 mg (0.85 mmol) of compound 140 in 0.5 mL of CH$_2$Cl$_2$ was added 14 µL (13.3 mg, 0.168 mmol) of pyridine. The mixture was cooled to 0° C. and a solution of 71 mg (0.021 mmol) of diamino-PEG, compound 141, in 0.5 mL of CH$_2$Cl$_2$ was added. The mixture was stirred under nitrogen atmosphere at room temperature for 18 hours, and partitioned between 10 mL of 1 N HCl and three 10 mL portions of CH$_2$Cl$_2$. The combined CH$_2$Cl$_2$ layers were dried (MgSO$_4$), filtered, and concentrated. Purification by silica gel chromatography (step gradient 5/95 MeOH/CH$_2$Cl$_2$ to 10/90 MeOH/CH$_2$Cl$_2$) provided 66 mg (69%) of compound 142 as a viscous oil: $^1$H NMR (CDCl$_3$): δ 1.45 (s, 36H), 1.60–1.80 (m, 24H), 2.39 (t, 8H), 3.39 (m, 8H), 3.50–3.80 (brd s, approx. 318H), 3.87 (t, 8H), 4.22 (t, 4H), 7.50 (brd s, 2H), 7.63 (s, 4H), 7.77 (s, 2H), 8.08 (s, 2H), 8.60 (s, 2H); mass spectrum (MALDI) (M+H) calculated for C$_{207}$H$_{389}$N$_{12}$O$_{93}$: 4535. Found distribution centered at approximately 4324.

Figure 13:
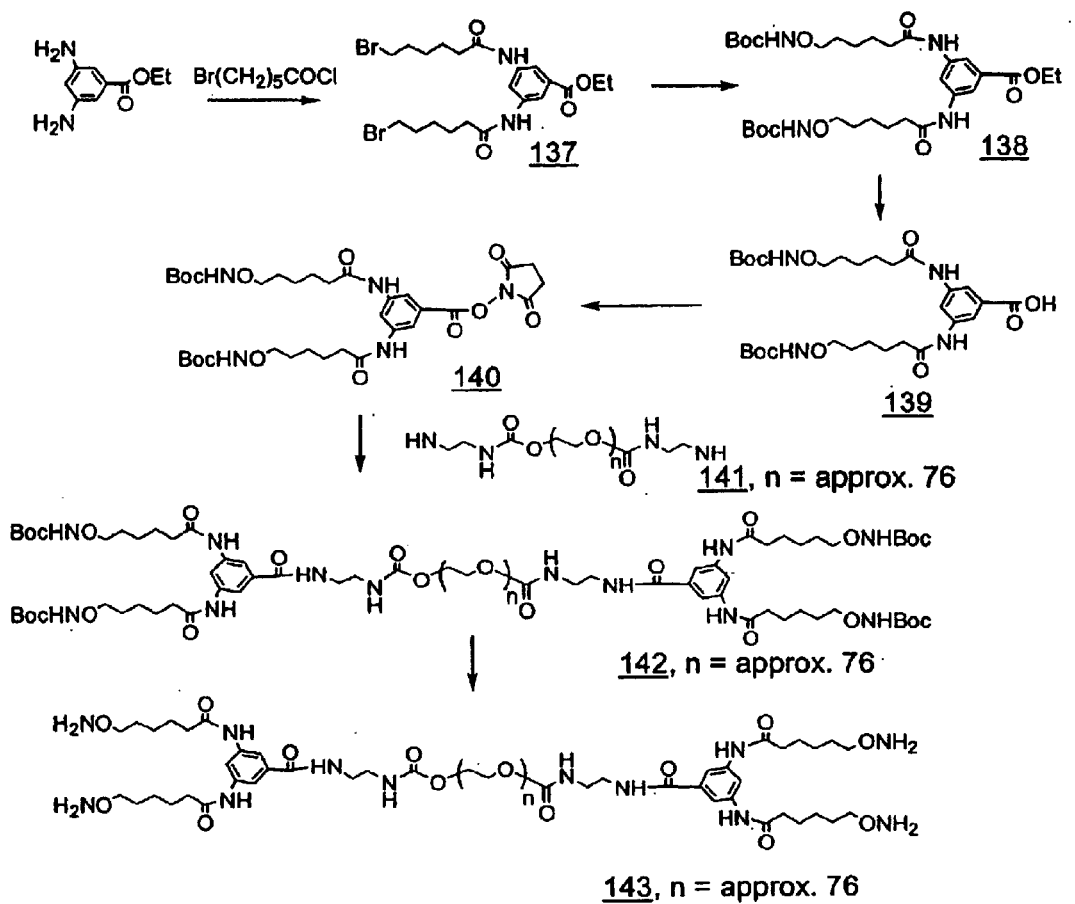
FIG. 13 shows a scheme for the synthesis of compound 143.

Analogously, the synthesis can be conducted with compound 141 of the desired molecular weight, for example, where n is optionally greater than 500, for example, 550, 600, 800 or more, as shown in FIG. 13.

Compound 143: The Boc-protecting groups are removed from compound 142 in a manner essentially similar to that described for the preparation of compound 16 to provide 143 as shown in FIG. 13.

Synthesis of compound 302: To a solution of 209 mg (9.36 μmol) of compound 123c and 8.84 mg (11.2 μmol) of compound 117 in 5 mL of anhydrous pyridine was added 3.26 uL (2.36 mg, 23.4 μmol) of triethylamine. The mixture was stirred for 18 hours under a N$_2$ atmosphere, the pyridine was removed by rotory evaporation under vacuum, and the residue was purified by preparative HPLC on a 22 mm×250 mm aminopropyl silica column (gradient, 10% A to 30% B over 60 minutes; A=H$_2$O, B=CH$_3$CN) to provide 200 mg (93%) of compound 302.

Synthesis of compound 303: The Boc-protecting groups are removed from compound 302 in a manner essentially similar to that described for the preparation of compound 16 to provide compound 303.

Synthesis of compound 304: To a solution of 4.43 mL (4.48 g, 30.2 mmol) of 2,2'-(ethylenedioxy)bis(ethylamine) (Aldrich Chemical Co.) in 50 mL of EtOAc was added a solution of 1.04 g (3.0 mmol) of compound 106. A precipitate formed which was removed by filtration. The filtrate was concentrated and the residue was dissolved in 100 mL of CH$_2$Cl$_2$ and shaken with 50 mL of 1 N NaOH. The aqueous layer was extracted with four 50 mL portions of CH$_2$Cl$_2$, and all the CH$_2$Cl$_2$ extracts were combined and concentrated to a yellow oil. Purification by silica gel chromatography (1.25/13.75/85 con NH$_4$OH/MeOH/CH$_2$Cl$_2$) provided 520 mg (46%) of compound 304 as a yellowish oil.

Synthesis of compound 305: To a solution of 500 mg (23.2 umol) of compound 130 in 9 mL of anhydrous pyridine was added a solution of 21.9 mg (58.1 umol) of compound 304 in 1 mL of pyridine followed by 26 uL (18.8 mg, 186 umol) of triethylamine, and the mixture was stirred under nitrogen atmosphere for 18 hours. The pyridine was removed by rotory evaporation under vacuum, and the residue was purified by preparative HPLC on a 22 mm×250 mm aminopropyl silica column (gradient, 13% A to 33% B over 60 minutes; A=H$_2$O, B=CH$_3$CN) to provide 428 mg (84%) of compound 305.

Figure 17:
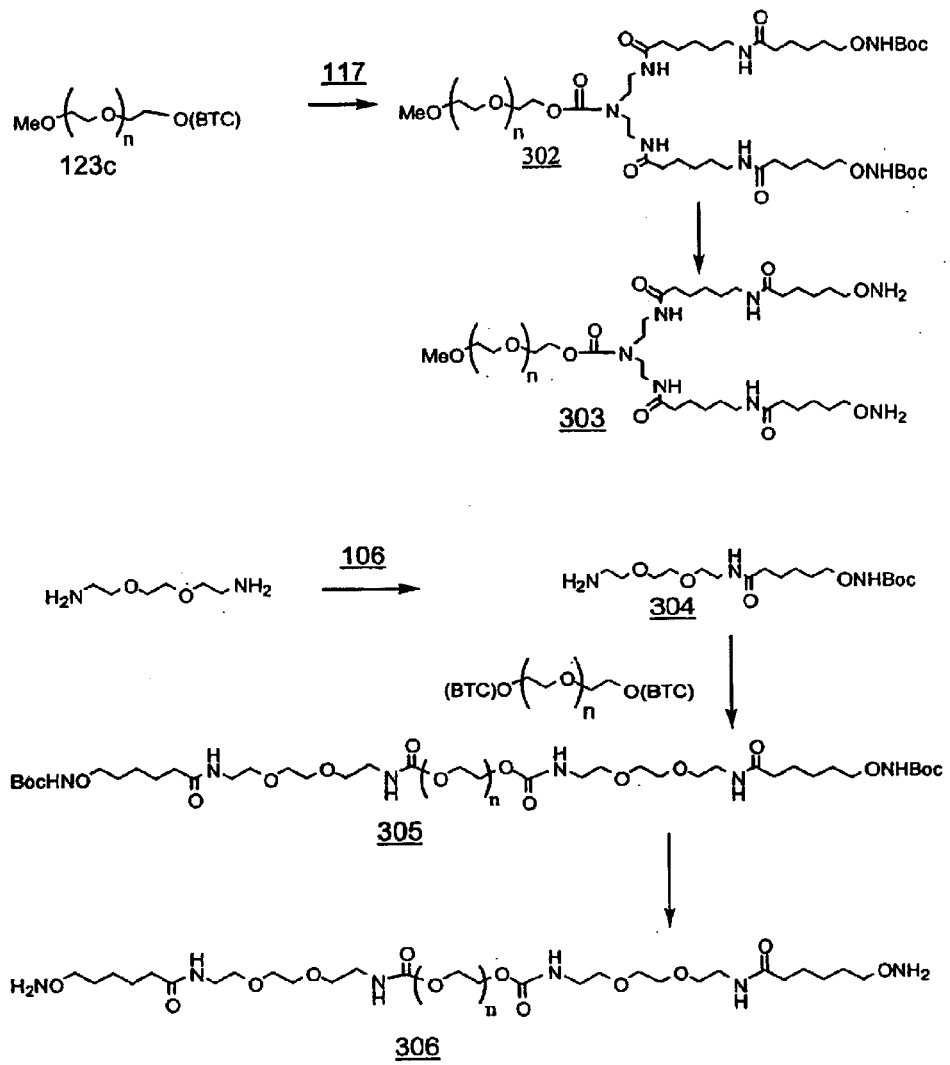
FIG. 17 is a scheme for the synthesis of compounds 303 and 306.

Synthesis of compound 306: The Boc-protecting groups are removed from compound 305 in a manner essentially similar to that described for the preparation of compound 16 to provide compound 306 (FIG. 17).

Example 7

Method of Preparation of Conjugates

Conjugates 200, 201, 202, 203, 204, and 205 (FIG. 7) were prepared as follows.

Compound 200: To a solution of 68.8 mg (9.74 μmol 6 equivalents) of TA/D1 in 10 mL of helium sparged 0.1 M, pH 4.6 sodium acetate buffer was added a solution of 36.8 mg (1.62 μmol) of compound 125c in 6.15 mL of 1/1 acetonitrile/0.1 M, pH 8.0 tris acetate buffer. Care was taken to keep the mixture under nitrogen atmosphere while stirring at room temperature for 18 hours. When the reaction was complete, it was directly purified by cation exchange chromatography using a PolyCat A WCX column manufactured by PolyLC Inc. (gradient 10% B to 25% B, A=10 mM sodium phosphate pH 7 in 1/9 acetonitrile/H$_2$O) to provide 57 mg (40%) of compound 200.

Compound 201: Compound 201 was prepared in a manner essentially similar to compound 200. Thus, to an approximately 1 mM solution of 6 equivalents of TA/D1 in helium sparged 0.1 M, pH 4.6 sodium acetate buffer was added 1 equivalent of compound 125a as a 0.25 to 10 mM solution in 1/1 acetonitrile/0.1 M, pH 8.0 tris acetate buffer. Care was taken to keep the mixture under nitrogen atmosphere while stirring at room temperature for 18 hours. When the reaction was complete, it was directly purified by cation exchange chromatography to provide compound 201.

Compound 202: Compound 202 was prepared in a manner essentially similar to 200. Thus, to an approximately 1 mM solution of 6 equivalents of TA/D1 in helium sparged 0.1 M, pH 4.6 sodium acetate buffer was added 1 equivalent of compound 132 as a 0.25 to 10 mM solution in 1/1 acetonitrile/0.1 M, pH 8.0 tris acetate buffer. Care was taken to keep the mixture under nitrogen atmosphere while stirring at room temperature for 18 hours. When the reaction was complete, it was directly purified by cation exchange chromatography to provide compound 202.

Also isolated were two lower valent species as minor impurities. A compound with three domain 1 polypeptides attached, as evidenced by polyacrylamide gel electrophoresis and mass spectroscopy, was isolated and is referred to as 202 trimer. A compound with two domain 1 poly peptides attached, as evidenced by polyacrylamide gel electrophoresis and mass spectroscopy, was isolated and is referred to as 202 dimer.

Compound 203: Compound 203 was prepared in a manner essentially similar to 200. Thus, to an approximately 1 mM solution of 6 equivalents of TA/D1 in helium sparged 0.1 M, pH 4.6 sodium acetate buffer was added 1 equivalent of compound 136 as a 0.25 to 10 mM solution in 1/1 acetonitrile/0.1 M, pH 8.0 tris acetate buffer. Care was taken to keep the mixture under nitrogen atmosphere while stirring at room temperature for 18 hours. When the reaction was complete, it was directly purified by cation exchange chromatography to provide compound 203.

Compound 204: Compound 204 was prepared in a manner essentially similar to 200. Thus, to an approximately 1 mM solution of 6 equivalents of TA/D1 in helium sparged 0.1 M, pH 4.6 sodium acetate buffer was added 1 equivalent of compound 143 as a 0.25 to 10 mM solution in 1/1 acetonitrile/0.1 M, pH 8.0 tris acetate buffer. Care was taken to keep the mixture under nitrogen atmosphere while stirring at room temperature for 18 hours. When the reaction was complete, it was directly purified by cation exchange chromatography to provide compound 204.

Compound 205: Compound 205 was prepared in a manner essentially similar to 200. Thus, to an approximately 1 mM solution of 6 equivalents of TA/D1 in helium sparged 0.1 M, pH 4.6 sodium acetate buffer was added 1 equivalent of compound 125b as a 0.25 to 10 mM solution in 1/1 acetonitrile/0.1 M, pH 8.0 tris acetate buffer. Care was taken to keep the mixture under nitrogen atmosphere while stirring at room temperature for 18 hours. When the reaction was complete, it was directly purified by cation exchange chromatography to provide compound 205.

Figure 16:
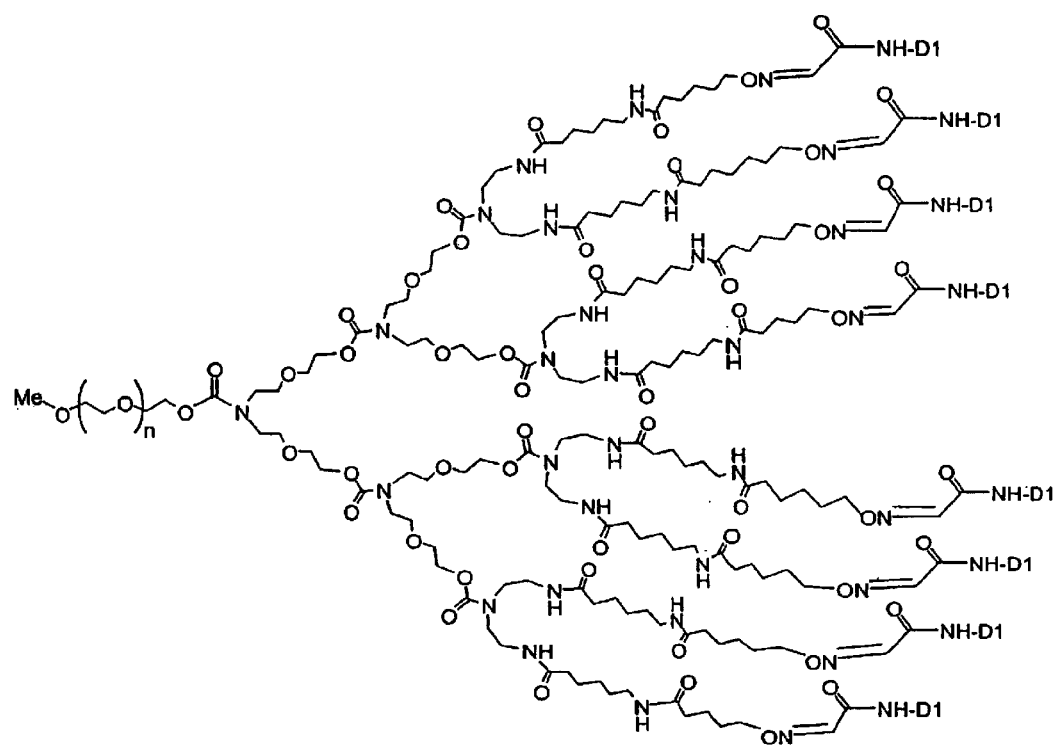
FIG. 16 shows the structure of exemplary conjugate 300.

Synthesis of compound 300: Compound 300 was prepared in a manner essentially similar to compound 200. Thus, to an approximately 1 mM solution of 12 equivalents of TA/D1 in helium sparged 0.1 M, pH 4.6 sodium acetate buffer was added 1 equivalent of compound 129 as a 0.25 to 10 mM solution in 1/1 acetonitrile/0.1 M pH 8.0 tris acetate buffer. Care was taken to keep the mixture under nitrogen atmosphere while stirring at room temperature for 18 hours. When the reaction was complete, it was directly purified by cation exchange chromatography to provide compound 300 (FIG. 16).

Synthesis of compound 309: Compound 309 was prepared in a manner essentially similar to compound 200. Thus, to an approximately 1 mM solution of 3 equivalents of TA/D1 in helium sparged 0.1 M, pH 4.6 sodium acetate buffer was added 1 equivalent of compound 303 as a 0.25 to 10 mM solution in 1/1 acetonitrile/0.1 M pH 8.0 tris acetate buffer. Care was taken to keep the mixture under nitrogen atmosphere while stirring at room temperature for 18 hours. When the reaction was complete, it was directly purified by cation exchange chromatography to provide compound 303.

Figure 18:
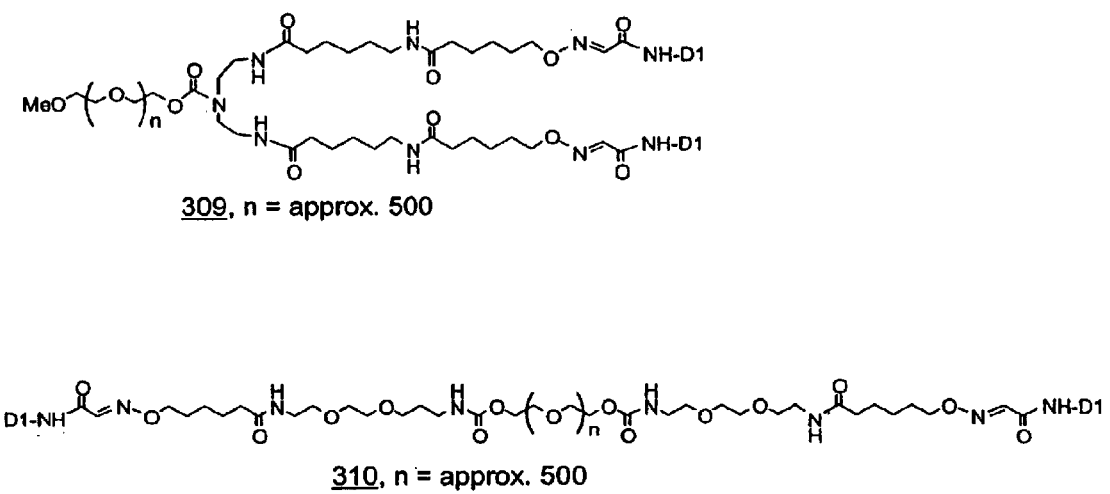
FIG. 18 shows the structure of some exemplary conjugates 309 and 310.

Synthesis of compound 310: Compound 310 was prepared in a manner essentially similar to compound 200. Thus, to an approximately 1 mM solution of 3 equivalents of TA/D1 in helium sparged 0.1 M, pH 4.6 sodium acetate buffer was added 1 equivalent of compound 306 as a 0.25 to 10 MM solution in 1/1 acetonitrile/0.1 M pH 8.0 tris acetate buffer. Care was taken to keep the mixture under nitrogen atmosphere while stirring at room temperature for 18 hours. When the reaction was complete, it was directly purified by cation exchange chromatography to provide compound 310 (FIG. 18).

Example 8

Evaluation of Toleragen Efficiency and Serum Half-Life

Domain 1—keyhole limpet hemocyanin conjugate (D1 CYS-KLH) was prepared for use in animal immunization. Recombinant Domain 1 with a fifth cysteine was expressed as a glutathione mixed disulfide in insect cells using the baculovirus expression vector system. The structure consists of the first 66 amino-terminal amino acids present in native human $\beta_2$-glycoprotein I followed by a C-terminal leu-(his)$_5$ expression tag. The polyhistidine expression tag at the C-terminus was the basis for a purification procedure by nickel affinity chromatography. Iverson et al. (1998) *Proc. Nat'l. Acad. Sci.* 95: 15542–15546.

The resulting Domain 1 with a free sulfhydryl (D1 CYS-SH) was alkylated by maleimidyl-KLH. Maleimidyl-activated KLH (Pierce Chemical Co.; Rockford, Ill.) was dissolved at 10 mg/mL in water as per the manufacturer's instructions. Immediately, the KLH was added to D1 CYS-SH at a ratio of 1027 mg per mg D1-SH. The tube containing the KLH and D1 CYS was mixed by rotation at 2 h×RT. At the end of the incubation the contents were dialyzed against cold PBS at 4° C. using a >25,000 MW cut-off membrane for the removal of unconjugated D1 CYS. An aliquot of the dialyzed sample was removed and tested for the presence of immunoreactive D1 by an ELISA with patient-derived affinity purified antiphospholipid antibodies (aPL).

An immunized rat model was used for measuring toleragen efficacy. Lewis rats (Harlan Sprague Dawley, Indianapolis, Ind.) were immunized i.p. with 10 µg of D1 CYS-KLH in alum with pertussis adjuvant. Three weeks after priming, groups of four animals were treated i.v. with toleragen or PBS control. Five days after treatment animals were boosted i.p. with 10 µg D1 CYS-KLH, and sera samples were collected seven days after boost.

An ELISA was used for detection of anti-domain 1 antibody in rat sera. Nunc Maxisorp Immunoplates (Nalge Nunc International, Rochester, N.Y.) were coated overnight with 50 µl of 5 µg/ml recombinant human $\beta_2$-GPI in carbonate buffer (Sigma, St. Louis, Mo.) pH 9.6 at 4° C. Subsequent steps were carried out at room temperature. Plates were washed 3× with phosphate buffered saline (PBS), then blocked 1 h with 250 µl 2% nonfat dry milk (Carnation, Solon, Ohio) in PBS. After washing, wells were incubated 1 h with 50 µl serial dilutions in PBS of each sera sample in triplicate. Non-immunized serum was used as control, and a pool of sera from immunized animals was used to generate a standard curve. After washing, the wells were incubated 1 h with 50 µl alkaline phosphatase-conjugated goat anti-rat IgG (Jackson ImmunoResearch, West Grove, Pa.) diluted 1:2000 in PBS/0.1% BSA. Wells were washed 3× with dIH$_2$O and were developed 20 minutes with PPMP solution ((10 gm phenolphthalein monophosphate (Sigma, St. Louis, Mo.), 97.4 ml 2-amino-2-methyl-1-propanol (Sigma), 9.62 ml dIH$_2$O, 21 ml HCl)). Color development was stopped with 50 µl 0.2 M Na$_2$HPO$_4$ and the OD$_{550}$ was read on a Bio-Tek Instruments PowerWave 340 Microplate Spectrophotometer (Winooski, Vt.). Nominal antibody units were assigned to the standard pool and the concentrations of anti-domain 1 antibody (units/ml) in test sera were derived from the standard curve. Percent suppression of anti-domain 1 antibody by multivalent platform conjugate, using conjugates 200, 201, 202 and 203 treatment was calculated by comparison to PBS-treated controls. The results are shown in Table 1, below.

TABLE 1

Percent Suppression of Anti-Domain 1 Antibody in Immunized Rats

| | nanomoles drug/rat | | | | |
|---|---|---|---|---|---|
| Compound | 0.17 | 1.7 | 17 | 2.4 | 3.5 |
| 200 | 61 | 82 | 89 | | |
| 201 | 34 | 73 | 86 | | |
| 202 | 72 | 89 | 96 | | |
| 203 | 73 | 93 | 94 | | |
| 202 trimer | | | | 83 | |
| 202 dimer | | | | | 70 |

By definition, PBS control = 0% suppression

The plasma pharmacokinetics of the compounds were measured in mice, rats and macaques. The compounds were radiolabeled with $^{125}I$ by the iodine monochloride method. Contreras et al., 1983, *Methods in Enzymology* 92: 277–292. The labeled compound was injected i.v. into female Balb/c mice, male Sprague-Dawley rats and female Cynomologous macaques. Plasma samples were collected over one hour in mice and over twenty-four hours in rats and macaques. The amount of radiolabeled drug was detected using a Packard Instruments Cobra Gamma counter (Dowers Grove, Ill.) Pharmacokinetic parameters were calculated using Pharsight WinNonLin software (Mountain View, Calif.) The overall plasma half life was calculated using the formula $t_{1/2}$=ln2(AUC/0.5*Cmax). The Clearance rate (CL, ml/hour and half-life ($t_{1/2}$, hours) for all three species are shown below in Table 2.

TABLE 2

Pharmacokinetic Parameters in mice, rats and macaques

| # | Mice Cl | t½ | Rats Cl | t½ | Macaques Cl | t½ |
|---|---|---|---|---|---|---|
| 204 | 62 | 0.05 | 1.70 | 8.0 | 64 | 3.3 |
| 200 | 1.2 | 0.61 | 0.67 | 20.2 | 34 | 7.5 |
| 201 | 9.0 | 0.28 | 1.48 | 9.8 | 89 | 2.2 |
| 205 | 6.7 | 0.30 | 0.78 | 14.0 | 48 | 4.7 |
| 202 | 2.3 | 0.73 | 0.69 | 18.4 | 28 | 5.7 |
| 203 | 1.5 | 1.84 | 0.65 | 20.0 | 12 | 13.2 |
| 300 | 4.2 | 0.27 | 0.98 | 14.7 | ND | ND |
| 301 | 1.1 | 2.07 | 0.52 | 37.7 | ND | ND |

What is claimed is:

1. A composition comprising chemically defined valency platform molecules, wherein the valency platform molecules individually comprise a high molecular weight polyethylene oxide group having a molecular weight of at least about 18,000 Daltons, and wherein said valency platform molecules have a polydispersity less than 1.2.

2. The composition of claim 1, wherein the valency platform molecules individually comprise a second high molecular weight polyethylene oxide group having a molecular weight of at least about 18,000 Daltons.

3. The composition of claim 1, wherein the high molecular weight polyethylene oxide group has a molecular weight of greater than about 22,000 Daltons.

4. The composition of claim 1, wherein the high molecular weight polyethylene oxide group has a molecular weight of greater than about 40,000 Daltons.

5. The composition of claim 1, wherein the high molecular weight polyethylene oxide group has the formula:

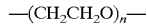

wherein n is greater than about 500.

6. The composition of claim 5, wherein n is greater than about 600.

7. The composition of claim 5, wherein n is greater than about 700.

8. The composition of claim 5, wherein n is greater than about 800.

9. The composition of claim 1, wherein the valency platform molecules individually comprise a core group and at least three arms wherein each arm comprises a terminus.

10. The composition of claim 9, wherein the core group comprises the high molecular weight polyethylene oxide group.

11. The composition of claim 9, wherein an arm comprises the high molecular weight polyethylene oxide group.

12. The composition of claim 9, wherein the high molecular weight polyethylene oxide group is attached to the core or one of said arms.

13. The composition of claim 1, wherein the valency platform molecules individually comprise at least three reactive conjugating groups selected from the group consisting of hydroxyl, thiol, isocyanate, isothiocyanate, amine, alkyl halide, alkylmercurial halide, aldehyde, ketone, carboxylic acid halide, α-halocarbonyl, α,β-unsaturated carbonyl, haloformate ester, carboxylic acid, carboxylic ester, carboxylic anhydride, O-acyl isourea, hydrazide, maleimide, imidate ester, sulfonate ester, sulfonyl halide, α,β-unsaturated sulfone, aminooxy, semicarbazide, and β-aminothiol.

14. The composition of claim 1, wherein the valency platform molecules individually comprise at least 3 aminooxy groups.

15. The composition of claim 1, wherein the valency platform molecules individually comprise at least 3 carbamate groups.

16. A composition comprising conjugates comprising biologically active molecules and the valency platform molecules according to claim 1.

17. The composition of claim 16, wherein the biologically active molecules are selected from the group consisting of polysaccharides, polypeptides, nucleic acids, and lipids.

18. The composition of claim 16, wherein the conjugates are B cell toleragens.

19. The composition of claim 17, wherein the biologically active molecules comprise a nucleic acid or analog thereof, which specifically binds to an anti-double stranded DNA antibody.

20. The composition of claim 18, wherein the biologically active molecules are $\beta_2$GPI domain 1 polypeptides or analogs thereof that specifically bind to a $\beta_2$GPI-dependent antiphospholipid antibody.

21. The composition of claim 20, wherein the conjugates are effective for the treatment of antibody mediated thrombosis.

22. The composition of claim 17, wherein the biologically active molecules are $\alpha_1$ Gal epitopes or analogs thereof that specifically bind to an anti-$\alpha_1$ Gal antibody.

23. A pharmaceutically acceptable composition comprising the composition of claim 16 and a pharmaceutically acceptable carrier.

24. A conjugate comprising a chemically defined valency platform molecule and a polypeptide comprising a $\beta_2$GPI domain 1 polypeptide, wherein the conjugate comprises a high molecular weight polyethylene oxide group having a molecular weight of at least about 18,000 Daltons.

25. The conjugate of claim 24, wherein the valency platform molecule comprises at least 3 aminooxy groups.

26. The conjugate of claim 24, wherein the valency platform molecule comprises at least 3 carbamate groups.

27. The conjugate of claim 24, wherein the high molecular weight polyethylene oxide group has a molecular weight greater than about 22,000 Daltons.

28. The conjugate of claim 24, wherein the valency platform molecule comprises a core group and at least three arms, wherein each arm comprises a terminus.

29. The conjugate of claim 24, wherein the polypeptide specifically binds to a $\beta_2$GPI-dependent antiphospholipid antibody.

30. The conjugate of claim 29, wherein the polypeptide lacks a T cell epitope capable of activating T cells in an individual having $\beta_2$GPI dependent antiphospholipid antibodies.

31. The conjugate of claim 24, wherein the $\beta_2$GPI domain 1 polypeptide comprises at least five contiguous amino acids of FIG. 19 (SEQ ID NO: 2).

32. The conjugate of claim 24, wherein the $\beta_2$GPI domain 1 polypeptide comprises amino acids Nos. 2–63 of SEQ ID NO: 2.

33. The conjugate of claim 24, wherein the conjugate is selected from the group consisting of compounds 200, 202, 203, and 205 shown in FIG. 7 and compound 300 shown in FIG. 16, wherein D1 in said structures is a polypeptide consisting of amino acids No. 2–63 of SEQ ID NO: 2.

34. The composition of claim 22, wherein the biologically active molecules are said $\alpha_1$ Gal epitopes.

35. The conjugate of claim 24, wherein the conjugate is effective for the treatment of antibody mediated thrombosis.

36. The composition of claim 16, wherein the average total molecular weight of the conjugates is no greater than about 200,000 Daltons.

37. The composition of claim 16, wherein the high molecular weight polyethylene oxide group has a molecular weight of greater than about 22,000 Daltons.

38. The composition of claim 1, wherein the high molecular weight polyethylene oxide group has a molecular weight of greater than about 30,000 Daltons.

39. The composition of claim 16, wherein the high molecular weight polyethylene oxide group has a molecular weight of greater than about 40,000 Daltons.

40. The composition of claim 1, wherein the high molecular weight polyethylene oxide group has a molecular weight of greater than about 50,000 Daltons.

41. The composition of claim 1, wherein the high molecular weight polyethylene oxide group has a molecular weight of greater than about 100,000 Daltons.

42. The composition of claim 16, wherein the high molecular weight polyethylene oxide group has the formula:

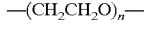

$$—(CH_2CH_2O)_n—$$

wherein n is greater than about 500.

43. The composition of claim 42, wherein n is greater than about 600.

44. The composition of claim 42, wherein n is greater than about 700.

45. The composition of claim 42, wherein n is greater than about 800.

46. The composition of claim 5, wherein n is greater than about 900.

47. The composition of claim 5, wherein n is about 400 to 550.

48. The composition of claim 5, wherein n is 520 to 600.

49. The composition of claim 5, wherein n is 600 to 800.

50. The composition of claim 5, wherein n is 600 to 1000.

51. The composition of claim 16, wherein the valency platform molecules individually comprise a second high molecular weight polyethylene oxide group having a molecular weight of at least about 18,000 Da.

52. The composition of claim 16, wherein the valency platform molecules individually comprise a core group and at least three arms wherein each arm comprises a terminus.

53. The composition of claim 52, wherein the core group comprises the high molecular weight polyethylene oxide group.

54. The composition of claim 52, wherein an arm comprises the high molecular weight polyethylene oxide group.

55. The composition of claim 52, wherein the high molecular weight polyethylene oxide group is attached to the core or one of said arms.

56. The composition of claim 16, wherein the valency platform molecules prior to conjugation individually comprise at least three reactive conjugating groups selected from the group consisting of hydroxyl, thiol, isocyanate, isothiocyanate, amine, alkyl halide, alkylmercurial halide, aldehyde, ketone, carboxylic acid halide, α-haloearbonyl, α,β-unsaturated carbonyl, haloformate ester, carboxylic acid, carboxylic ester, carboxylic anhydride, O-acyl isourea, hydrazide, maleimide, imidate ester, sulfonate ester, sulfonyl halide, α,β-unsaturated sulfone, aminooxy, semicarbazide, and β-aminothiol.

57. The composition of claim 16, wherein the valency platform molecules prior to conjugation individually comprise at least 3 aminooxy groups.

58. The composition of claim 16, wherein the valency platform molecules individually comprise at least 3 carbamate groups.

59. A composition comprising chemically defined valency platform molecules, wherein the chemically defined valency platform molecules individually comprise a first and a second polyethylene oxide group, wherein the first and the second polyethylene oxide groups each have a molecular weight of greater than about 5,000 Da, and wherein the total of the molecular weights of all polyethylene oxide groups in each valency platform molecule in combination is greater than about 18,000 Da, and wherein said valency platform molecules have a polydispersity less than 1.2.

60. The composition of claim 59, wherein the molecular weight of all polyethylene oxide groups in each valency platform molecule in combination is greater than about 20,000 Da.

61. The composition of claim 59, wherein the molecular weight of all polyethylene oxide groups in each valency platform molecule in combination is greater than about 22,000 Da.

62. The composition of claim 59, wherein the molecular weight of all polyethylene oxide groups in each valency platform molecule in combination is greater than about 30,000 Da.

63. The composition of claim 59, wherein the molecular weight of all polyethylene oxide groups in each valency platform molecule in combination is greater than about 40,000 Da.

64. The composition of claim 59, wherein the molecular weight of all polyethylene oxide groups in each valency platform molecule in combination is greater than about 35,200 Da.

65. The composition of claim 59, wherein the molecular weight of all polyethylene oxide groups in each valency platform molecule in combination is greater than about 39,600 Da.

66. The composition of claim 59, wherein the molecular weight of all polyethylene oxide groups in each valency platform molecule in combination is greater than about 44,000 Da.

67. The composition of claim 59, wherein the molecular weight of all polyethylene oxide groups in each valency platform molecule in combination is 22,900–26,400 Da.

68. The composition of claim 59, wherein the molecular weight of all polyethylene oxide groups in each valency platform molecule in combination is 24,200–30,800 Da.

69. The composition of claim 59, wherein the molecular weight of all polyethylene oxide groups in each valency platform molecule in combination is 26,400–44,000 Da.

70. The composition of claim 59, wherein the molecular weight of all polyethylene oxide groups in each valency platform molecule in combination is 26,400–39,600 Da.

71. The composition of claim 59, wherein the molecular weight of all polyethylene oxide groups in each valency platform molecule in combination is 26,400–35,200 Da.

72. The composition of claim 59, wherein the first and the second polyethylene oxide groups each have a molecular weight of greater than about 10,000 Da.

73. The composition of claim 59, wherein the first and the second polyethylene oxide groups each have a molecular weight of about 5,000–10,000 Da.

74. The composition of claim 59, wherein the first and the second polyethylene oxide groups each have a molecular weight of about 8,000–20,000 Da.

75. The composition of claim 59, wherein the first and the second polyethylene oxide groups each have a molecular weight of about 10,000–20,000 Da.

76. The composition of claim 59, wherein the chemically defined valency platform molecules individually comprise a third and a fourth polyethylene oxide group.

77. The composition of claim 76, wherein the first, second, third, and fourth polyethylene oxide groups each have a molecular weight of about 8,000–20,000 Da.

78. The composition of claim 76, wherein the molecular weight of the first, second, third, and fourth polyethylene oxide groups in each valency platform molecule in combination is 26,400–44,000 Da.

79. A composition comprising conjugates comprising biologically active molecules and the valency platform molecules of claim 78, wherein the biologically active molecules are β₂GPI domain I polypeptides.

80. A chemically defined valency platform molecule having the formula:

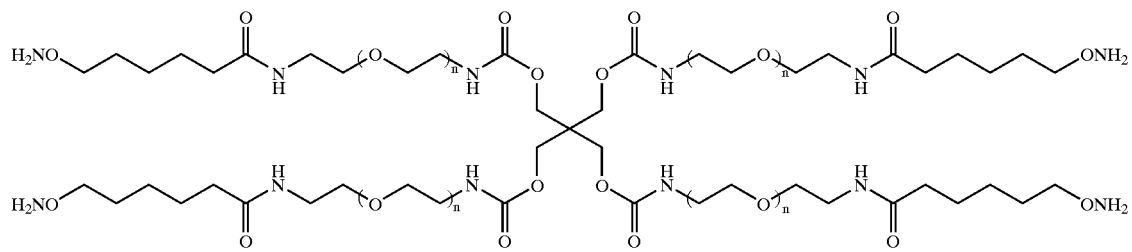

or an aminooxy protected form thereof; wherein the molecular weight of the polyethylene oxide groups in combination is 26,400–44,000 Da.

81. A chemically defined valency platform molecule having the formula:

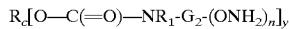

or an aminooxy protected form thereof;

wherein y is 2 to 16;

n is 1 to 32;

$R_1$ is H;

$R_c$ is a hydrocarbyl group having from 1 to 200 carbon atoms;

each $G_2$ independently comprises a polyethylene oxide group having a molecular weight of 44 to 22,000 Da;

wherein each $G_2$ further comprises an amide group;

with the proviso that the formula comprises at least a first and a second $G_2$ group, wherein the molecular weight of the polyethylene oxide groups in the first and the second $G_2$ groups are greater than about 5,000 Da; and wherein the total of the molecular weights of all polyethylene oxide groups in the valency platform molecule in combination is greater than about 18,000 Da.

82. A chemically defined valency platform molecule having the structure of one of the following formulae:

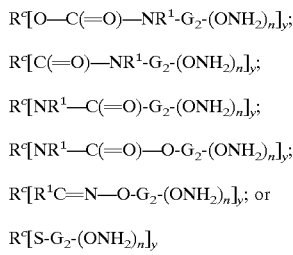

or an aminooxy protected form thereof;
wherein:
y is 1 to 16;
n is 1 to 32;
$R^1$ is H, alkyl, heteroalkyl, aryl, heteroaryl or $G_2$-$(ONH_2)_n$;
$R^c$ is an organic moiety comprising atoms selected from the group consisting of H, C, N, O, P, Si and S atoms, and optionally comprising one or more polyethylene oxide groups; and
$G_2$ is an organic moiety comprising atoms selected from the group consisting of H, C, N, O, P, Si and S atoms, and optionally comprising one or more polyethylene oxide groups;
with the proviso that at least one of the $R^c$ or $G_2$ groups comprises a high molecular weight polyethylene oxide group having a molecular weight of greater than about 18,000 Da.

83. A chemically defined valency platform molecule having the structure of one of the following formulae:

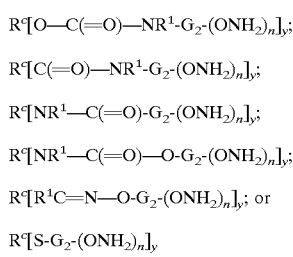

or an aminooxy protected form thereof;
wherein:
y is 1 to 16;
n is 1 to 32;
$R^1$ is H, alkyl, heteroalkyl, aryl, heteroaryl or $G_2$-$(ONH_2)_n$;
$R^c$ is an organic moiety comprising atoms selected from the group consisting of H, C, N, O, P, Si and S atoms, and optionally comprising one or more polyethylene oxide groups; and
$G_2$ is an organic moiety comprising atoms selected from the group consisting of H, C, N, O, P, Si and S atoms, and optionally comprising one or more polyethylene oxide groups;

with the proviso that the valency platform molecule comprises at least 2 polyethylene oxide groups each having a molecular weight of greater than about 5,000 Da, and wherein the total of the molecular weights of all polyethylene oxide groups in the valency platform molecule in combination is greater than about 18,000 Da.

84. A chemically defined valency platform molecule having the structure of one of the following formulae:

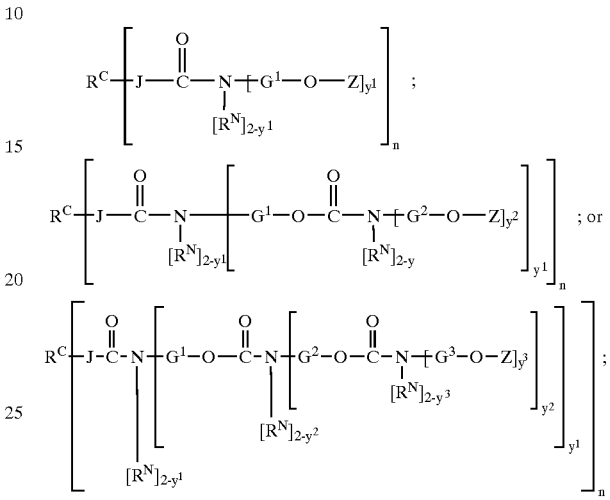

wherein:
n is an integer from 1 to 10;
$y^1$, $y^2$, and $y^3$ are independently 1 or 2;
J independently denotes either an oxygen atom or a covalent bond;
$R^c$ is selected from the group consisting of:
hydrocarbyl groups having from 1 to 20 carbon atoms;
organic groups consisting only of carbon, oxygen, and hydrogen atoms, and having from 1 to 20 carbon atoms;
organic groups consisting only of carbon, oxygen, nitrogen, and hydrogen atoms, and having from 1 to 20 carbon atoms; and
organic groups consisting only of carbon, oxygen, sulfur, and hydrogen atoms, and having from 1 to 20 carbon atoms;
and wherein $R^c$ optionally further comprises one or more polyethylene oxide groups;
each $G^1$, $G^2$, and $G^3$ is independently selected from the group consisting of:
hydrocarbyl groups having from 1 to 20 carbon atoms;
organic groups consisting only of carbon, oxygen, and hydrogen atoms, and having from 1 to 20 carbon atoms;
organic groups consisting only of carbon, oxygen, nitrogen, and hydrogen atoms, and having from 1 to 20 carbon atoms;
and wherein each $G^1$, $G^2$, and $G^3$ may independently further comprise one or more polyethylene oxide groups;
each $R^N$ is independently selected from the group consisting of:
hydrogen;
linear or branched alkyl groups having from 1 to 15 carbon atoms;
alkyl groups comprising an alicyclic structure and having from 1 to 15 carbon atoms;

aromatic groups having from 6 to 20 carbon atoms;
heteroaromatic groups having from 3 to 20 carbon atoms;

each Z is independently selected from the group consisting of:

—H

—C(=O)OR$^{CARB}$

—C(=O)R$^{ESTER}$

—C(=O)NR$^A$R$^B$

—C(=O)NR$^{AB}$ wherein:
each R$^{CARB}$ is independently an organic group comprising from 1 to about 20 carbon atoms;
each R$^{ESTER}$ is independently an organic group comprising from 1 to about 20 carbon atoms;
each monovalent R$^A$ and R$^B$ and each divalent R$^{AB}$ is independently H or an organic group comprising from 1 to 20 carbon atoms, and further comprising a reactive conjugating functional group;
with the proviso that at least one of the R$^c$, G$^1$, G$^2$, or G$^3$ groups comprises a high molecular weight polyethylene oxide group having a molecular weight of greater than about 18,000 Da.

85. A chemically defined valency platform molecule having the structure of one of the following formulae:

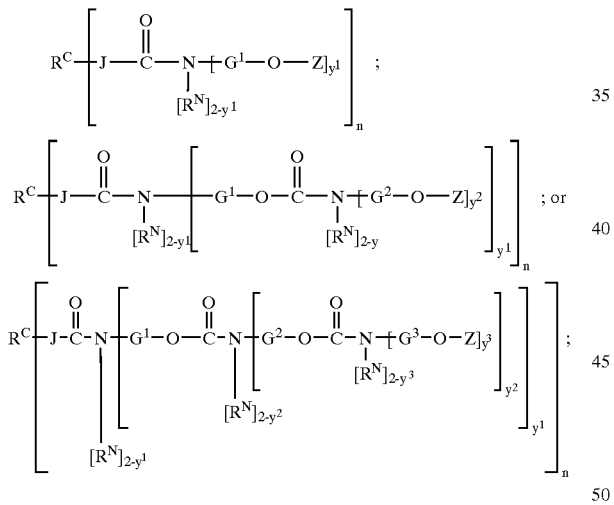

wherein:
n is an integer from 1 to 10;
y$^1$, y$^2$, and y$^3$ are independently 1 or 2;
J independently denotes either an oxygen atom or a covalent bond;
R$^c$ is selected from the group consisting of:
hydrocarbyl groups having from 1 to 20 carbon atoms;
organic groups consisting only of carbon, oxygen, and hydrogen atoms, and having from 1 to 20 carbon atoms;
organic groups consisting only of carbon, oxygen, nitrogen, and hydrogen atoms, and having from 1 to 20 carbon atoms; and
organic groups consisting only of carbon, oxygen, sulfur, and hydrogen atoms, and having from 1 to 20 carbon atoms;

and wherein R$^c$ optionally further comprises one or more polyethylene oxide groups;
each G$^1$, G$^2$, and G$^3$ is independently selected from the group consisting of:
hydrocarbyl groups having from 1 to 20 carbon atoms;
organic groups consisting only of carbon, oxygen, and hydrogen atoms, and having from 1 to 20 carbon atoms;
organic groups consisting only of carbon, oxygen, nitrogen, and hydrogen atoms, and having from 1 to 20 carbon atoms;
organic groups consisting only of carbon, oxygen, nitrogen, and hydrogen atoms, and having from 1 to 20 carbon atoms;
and wherein each G$^1$, G$^2$, and G$^3$ may independently further comprise one or more polyethylene oxide groups;
each R$^N$ is independently selected from the group consisting of:
hydrogen;
linear or branched alkyl groups having from 1 to 15 carbon atoms;
alkyl groups comprising an alicyclic structure and having from 1 to 15 carbon atoms;
aromatic groups having from 6 to 20 carbon atoms;
heteroaromatic groups having from 3 to 20 carbon atoms;
each Z is independently selected from the group consisting of:

—H

—C(=O)OR$^{CARB}$

—C(=O)R$^{ESTER}$

—C(=O)NR$^A$R$^B$

—C(=O)NR$^{AB}$ wherein:
each R$^{CARB}$ is independently an organic group comprising from 1 to about 20 carbon atoms;
each R$^{ESTER}$ is independently an organic group comprising from 1 to about 20 carbon atoms;
each monovalent R$^A$ and R$^B$ and each divalent R$^{AB}$ is independently H or an organic group comprising from 1 to 20 carbon atoms, and further comprising a reactive conjugating functional group;
with the proviso that the valency platform molecule comprises at least 2 polyethylene oxide groups each having a molecular weight of greater than about 5,000 Da, and wherein the total of the molecular weights of all polyethylene oxide groups in the valency platform molecule in combination is greater than about 18,000 Da.

86. A chemically defined valency platform molecule having the structure of one of the following formulae:

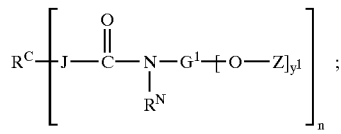

-continued

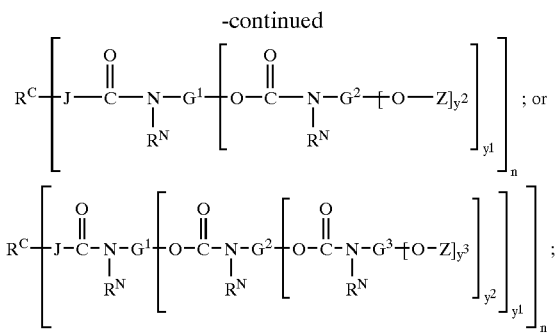

wherein:
n is an integer from 1 to 10;
$y^1$, $y^2$, and $y^3$ are independently 1 or 10;
J independently denotes either an oxygen atom or a covalent bond;
$R^C$ is selected from the group consisting of:
  hydrocarbyl groups having from 1 to 20 carbon atoms;
  organic groups consisting only of carbon, oxygen, and hydrogen atoms, and having from 1 to 20 carbon atoms;
  organic groups consisting only of carbon, oxygen, nitrogen, and hydrogen atoms, and having from 1 to 20 carbon atoms; and
  organic groups consisting only of carbon, oxygen, sulfur, and hydrogen atoms, and having from 1 to 20 carbon atoms;
and wherein $R^C$ optionally further comprises one or more polyethylene oxide groups;
each $G^1$, $G^2$, and $G^3$ is independently selected from the group consisting of:
  hydrocarbyl groups having from 1 to 20 carbon atoms;
  organic groups consisting only of carbon, oxygen, and hydrogen atoms, and having from 1 to 20 carbon atoms;
  organic groups consisting only of carbon, oxygen, nitrogen, and hydrogen atoms, and having from 1 to 20 carbon atoms;
and wherein each $G^1$, $G^2$, and $G^3$ may independently further comprise one or more polyethylene oxide groups;
each $R^N$ is independently selected from the group consisting of:
  hydrogen;
  linear or branched alkyl groups having from 1 to 15 carbon atoms;
  alkyl groups comprising an alicyclic structure and having from 1 to 15 carbon atoms;
  aromatic groups having from 6 to 20 carbon atoms;
  heteroaromatic groups having from 3 to 20 carbon atoms;
each Z is independently selected from the group consisting of:
  —H
  —C(=O)O$R^{CARB}$
  —C(=O)$R^{ESTER}$
  —C(=O)N$R^A R^B$
  —C(=O)N$R^{AB}$ wherein:
  each $R^{CARB}$ is independently an organic group comprising from 1 to about 20 carbon atoms;
  each $R^{ESTER}$ is independently an organic group comprising from 1 to about 20 carbon atoms;
  each monovalent $R^A$ and $R^B$ and each divalent $R^{AB}$ is independently H or an organic group comprising from 1 to 20 carbon atoms, and further comprising a reactive conjugating functional group;
  with the proviso that at least one of the $R^C$, $G^1$, $G^2$, or $G^3$ groups comprises a high molecular weight polyethylene oxide group having a molecular weight of greater than about 18,000 Da.

87. A chemically defined valency platform molecule having the structure of one of the following formulae:

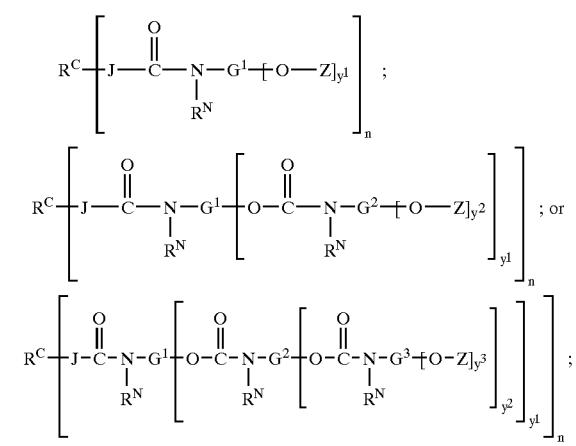

wherein:
n is an integer from 1 to 10;
$y^1$, $y^2$, and $y^3$ are independently a positive integer from 1 to 10;
J independently denotes either an oxygen atom or a covalent bond;
$R^C$ is selected from the group consisting of:
  hydrocarbyl groups having from 1 to 20 carbon atoms;
  organic groups consisting only of carbon, oxygen, and hydrogen atoms, and having from 1 to 20 carbon atoms;
  organic groups consisting only of carbon, oxygen, nitrogen, and hydrogen atoms, and having from 1 to 20 carbon atoms;
  organic groups consisting only of carbon, oxygen, sulfur, and hydrogen atoms, and having from 1 to 20 carbon atoms;
and wherein $R^c$ optionally further comprises one or more polyethylene oxide groups;
each $G^1$, $G^2$, and $G^3$ is independently selected from the group consisting of:
  hydrocarbyl groups having from 1 to 20 carbon atoms;
  organic groups consisting only of carbon, oxygen, and hydrogen atoms, and having from 1 to 20 carbon atoms;
  organic groups consisting only of carbon, oxygen, nitrogen, and hydrogen atoms, and having from 1 to 20 carbon atoms;
and wherein each $G^1$, $G^2$, and $G^3$ may independently further comprise one or more polyethylene oxide groups;
each $R^N$ is independently selected from the group consisting of:

hydrogen;
linear or branched alkyl groups having from 1 to 15 carbon atoms;
alkyl groups comprising an alicyclic structure and having from 1 to 15 carbon atoms;
aromatic groups having from 6 to 20 carbon atoms;
heteroaromatic groups having from 3 to 20 carbon atoms;
each Z is independently selected from the group consisting of:

—H

—C(=O)OR$^{CARB}$

—C(=O)R$^{ESTER}$

—C(=O)NR$^A$R$^B$

—C(=O)NR$^{AB}$ wherein:
each R$^{CARB}$ is independently an organic group comprising from 1 to about 20 carbon atoms;
each R$^{ESTER}$ is independently an organic group comprising from 1 to about 20 carbon atoms;
each monovalent R$^A$ and R$^B$ and each divalent R$^{AB}$ is independently H or an organic group comprising from 1 to 20 carbon atoms, and further comprising a reactive coniugating functional group;
with the proviso that the valency platform molecule comprises at least 2 polyethylene oxide groups each having a molecular weight of greater than about 5,000 Da, and wherein the total of the molecular weights of all polyethylene oxide groups in the valency platform molecule in combination is greater than about 18,000 Da.

88. A chemically defined valency platform molecule having the structure of one of the following formulae:

G$^{[1]}$    {T$^{[1]}$}$_{n[1]}$ ; or

G$^{[2]}$    {L$^{[2]}$—J$^{[2]}$—Z$^{[2]}$(T$^{[2]}$)$_{p[2]}$}$_{n[2]}$;

wherein
each of G$^{[1]}$ and G$^{[2]}$, if present, is independently a linear, branched or multiply-branched chain comprising 1–2,000 chain atoms selected from the group C, N, O, Si, P and S;
and wherein G$^{[1]}$ and G$^{[2]}$, if present, optionally further comprises one or more polyethylene oxide groups;
each T$^{[1]}$ and each T$^{[2]}$, if present, is independently chosen from the group NHR$^{SUB}$, C(=O)NHNHR$^{SUB}$, NHNHR$^{SUB}$, C(=O)OH, C(=O)OR$^{ESTER}$, C(=O)OC(=O)R$^B$, C(=O)X, S(=O)$_2$X, C(=NR$^{SUB}$)OR$^{SUB}$, NCO, NCS, OC(=O)X, C(=O)OC(=NR$^{SUB}$)NHR$^{SUB}$, C(=O)H, C(=O)R$^B$, SH, OH, C(=O)CH$_2$X, R$^{ALK}$X, S(=O)$_2$OR$^{ALK}$X, NR$^1$R$^2$ wherein R$^1$R$^2$ is —C(=O)CH=CHC(=O)—, C(=O)CR$^B$=CR$^B{}_2$, R$^{ALK}$—Hg—X, S(=O)CR$^B$=CR$^B{}_2$, and ONH$_2$;
wherein
each X is independently a halogen of atomic number greater than 16 and less than 54 or other leaving group;
each R$^{ALK}$ is independently a linear, branched, or cyclic alkyl (1–20C) group;
each R$^{SUB}$ is independently H, linear, branched, or cyclic alkyl (1–20C), aryl (6–20C), or alkaryl (7–30C);
each R$^{ESTER}$ is independently N-succinimidyl, p-nitrophenyl, pentafluorophenyl, tetrafluorophenyl, pentachlorophenyl, 2,4,5-trichlorophenyl, 2,4-dinitrophenyl, cyanomethyl, 5-chloro,8-quinolone, 1-piperidine, or N-benzotriazole;
each R$^B$ is independently a radical comprising 1–50 atoms selected from the group C, H, N, O, Si, P and S;
each L$^{[2]}$, if present, is independently chosen from the group O, NR$^{SUB}$ and S;
each J$^{[2]}$, if present, is independently chosen from the group C(=O) and C(=S);
each Z$^{[2]}$, if present, is independently a radical comprising 1–200 atoms selected from the group C, H, N, O, Si, P and S, and forming attachment sites for at least p$^{[2]}$ functional groups, wherein the attachment sites are alkyl, alkenyl, or aromatic carbon atoms;
and wherein Z$^{[2]}$, if present, optionally further comprises one or more polyethylene oxide groups;
n$^{[1]}$, if present, is 1 to 32;
n$^{[2]}$, if present, is 1 to 32; and
p$^{[2]}$, if present, is 1 to 8; with the proviso that the product n$^{[2]}$×p$^{[2]}$ be greater than 1 and less than 33;
with the proviso that at least one of the G$^{[1]}$, G$^{[2]}$, or Z$^{[2]}$ groups comprises a high molecular weight polyethylene oxide group having a molecular weight of greater than about 18,000 Da.

89. A chemically defined valency platform molecule having the structure of one of the following formulae;

G$^{[1]}$    {T$^{[1]}$}$_{n[1]}$ ; or

G$^{[2]}$    {L$^{[2]}$—J$^{[2]}$—Z$^{[2]}$(T$^{[2]}$)$_{p[2]}$}$_{n[2]}$;

wherein
each of G$^{[1]}$ and G$^{[2]}$, if present, is independently a linear, branched or multiply-branched chain comprising 1–2,000 chain atoms selected from the group C, N, O, Si, P and S;
and wherein G$^{[1]}$ and G$^{[2]}$, if present, optionally further comprises one or more polyethylene oxide groups;
each T$^{[1]}$ and each T$^{[2]}$, if present, is independently chosen from the group NHR$^{SUB}$, C(=O)NHNHR$^{SUB}$, NHNHR$^{SUB}$, C(=O)OH, C(=O)OR$^{ESTER}$, C(=O)OC(=O)R$^B$, C(=O)X, S(=O)$_2$X, C(=NR$^{SUB}$)OR$^{SUB}$, NCO, NCS, OC(=O)X, C(=O)OC(=NR$^{SUB}$)NHR$^{SUB}$, C(=O)H, C(=O)R$^B$, SH, OH, C(=O)CH$_2$X, R$^{ALK}$X, S(=O)$_2$OR$^{ALK}$X, NR$^1$R$^2$ wherein R$^1$R$^2$ is —C(=O)CH=CHC(=O)—, C(=O)CR$^B$=CR$^B{}_2$, R$^{ALK}$—Hg—X, S(=O)CR$^B$=CR$^B{}_2$, and ONH$_2$;
wherein
each X is independently a halogen of atomic number greater than 16 and less than 54 or other leaving group;
each R$^{ALK}$ is independently a linear, branched, or cyclic alkyl (1–20C) group;
each R$^{SUB}$ is independently H, linear, branched, or cyclic alkyl (1–20C), aryl (6–20C), or alkaryl (7–30C);
each R$^{ESTER}$ is independently N-succinimidyl, p-nitrophenyl, pentafluorophenyl, tetrafluorophenyl, pentachlorophenyl, 2,4,5-trichlorophenyl, 2,4-dinitrophenyl, cyanomethyl, 5-chloro,8-quinolone, 1-piperidine, or N-benzotriazole;

each $R^B$ is independently a radical comprising 1–50 atoms selected from the group C, H, N, O, Si, P and S;

each $L^{[2]}$, if present, is independently chosen from the group O, $NR^{SUB}$ and S;

each $J^{[2]}$, if present, is independently chosen from the group C(=O) and C(=S);

each $Z^{[2]}$, if present, is independently a radical comprising 1–200 atoms selected from the group C, H, N, O, Si, P and S, and forming attachment sites for at least $p^{[2]}$ functional groups, wherein the attachment sites are alkyl, alkenyl, or aromatic carbon atoms;

and wherein $Z^{[2]}$, if present, optionally further comprises one or more polyethylene oxide groups;

$n^{[1]}$, if present, is 1 to 32;

$n^{[2]}$, if present, is 1 to 32;

$p^{[2]}$, if present, is 1 to 8; with the proviso that the product $n^{[2]} \times p^{[2]}$ be greater than 1 and less than 33;

with the proviso that the valency platform molecule comprises at least 2 polyethylene oxide groups each having a molecular weight of greater than about 5,000 Da, and wherein the total of the molecular weights of all polyethylene oxide groups in the valency platform molecule in combination is greater than about 18,000 Da.

90. A chemically defined valency platform molecule having the structure of one of the following formulae:

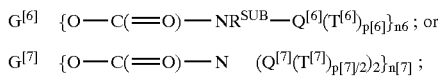

wherein each of $G^{[6]}$ and $G^{[7]}$, if present, is independently a linear, branched or multiply-branched chain comprising 1–2,000 chain atoms selected from the group C, N, O, Si, P and S;

and wherein $G^{[6]}$ and $G^{[7]}$, if present, optionally further comprises one or more polyethylene oxide groups;

each $T^{[6]}$ and each $T^{[7]}$, if present, is independently chosen from the group $NHR^{SUB}$, C(=O)NHNHR$^{SUB}$, NHNHR$^{SUB}$, C(=O)OH, C(=O)OR$^{ESTER}$, C(=O)OC(=O)R$^B$, C(=O)X, S(=O)$_2$X, C(=NR$^{SUB}$)OR$^{SUB}$, NCO, NCS, OC(=O)X, C(=O)OC(=NR$^{SUB}$)NHR$^{SUB}$, C(=O)H, C(=O)R$^B$, SH, OH, C(=O)CH$_2$X, R$^{ALK}$X, S(=O)$_2$OR$^{ALK}$X, NR$^1$R$^2$ wherein R$^1$R$^2$ is —C(=O)CH=CHC(=O)—, C(=O)CR$^B$=CR$^B$$_2$, R$^{ALK}$—Hg—X, S(=O)CR$^B$=CR$^B$$_2$, and ONH$_2$;

wherein each X is independently a halogen of atomic number greater than 16 and less than 54 or other leaving group;

each R$^{ALK}$ is independently a linear, branched, or cyclic alkyl (1–20C) group;

each R$^{SUB}$ is independently H, linear, branched, or cyclic alkyl (1–20C), aryl (1–20C), or alkaryl (1–30C);

each R$^{ESTER}$ is independently N-hydroxysuccinimidyl, p-nitrophenoxy, or pentafluorophenoxy;

each R$^B$ is independently a radical comprising 1–50 atoms selected from the group C, H, N, O, Si, P and S;

$n^{[6]}$, if present, is 1 to 32;

$p^{[6]}$, if present, is 1 to 8;

with the proviso that the product $n^{[6]} \times p^{[6]}$ be greater than 1 and less than 33;

$n^{[7]}$, if present, is 1 to 32;

$p^{[7]}$, if present, is 1 to 8;

with the proviso that the product $n^{[7]} \times p^{[7]}$ be greater than 1 and less than 33;

each $Q^{[6]}$ and each $Q^{[7]}$, if present, is independently a radical comprising 1–100 atoms selected from the group C, H, N, O, Si, P and S, and wherein each $Q^{[6]}$ and $Q^{[8\ 7]}$ moiety, if present, forms attachment sites for at least $p^{[6]}$ or $p^{[7]/2}$ functional groups, respectively, wherein the attachment sites are alkyl, alkenyl, or aromatic carbon atoms;

and wherein $Q^{[6]}$ and $Q^{[7]}$, if present, optionally further comprises one or more polyethylene oxide groups; and wherein $p^{[7]/2}$ is an integer;

with the proviso that at least one of the $G^{[6]}$, $G^{[7]}$, $Q^{[6]}$, or $Q^{[7]}$ groups comprises a high molecular weight polyethylene oxide group having a molecular weight of greater than about 18,000 Da.

91. A chemically defined valency platform molecule having the structure of one of the following formulae:

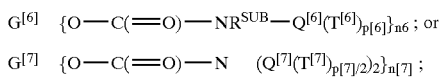

wherein each of $G^{[6]}$ and $G^{[7]}$, if present, is independently a linear, branched or multiply-branched chain comprising 1–2,000 chain atoms selected from the group C, N, O, Si, P and S;

and wherein $G^{[6]}$ and $G^{[7]}$, if present, optionally further comprises one or more polyethylene oxide groups;

each $T^{[6]}$ and each $T^{[7]}$, if present, is independently chosen from the group $NHR^{SUB}$, C(=O)NHNHR$^{SUB}$, NHNHR$^{SUB}$, C(=O)OH, C(=O)OR$^{ESTER}$, C(=O)OC(=O)R$^B$, C(=O)X, S(=O)$_2$X, C(=NR$^{SUB}$)OR$^{SUB}$, NCO, NCS, OC(=O)X, C(=O)OC(=NR$^{SUB}$)NHR$^{SUB}$, C(=O)H, C(=O)R$^B$, SH, OH, C(=O)CH$_2$X, R$^{ALK}$X, S(=O)$_2$OR$^{ALK}$X, NR$^1$R$^2$ wherein R$^1$R$^2$ is —C(=O)CH=CHC(=O)—, C(=O)CR$^B$=CR$^B$$_2$, R$^{ALK}$—Hg—X, S(=O)CR$^B$=CR$^B$$_2$, and ONH$_2$;

wherein each X is independently a halogen of atomic number greater than 16 and less than 54 or other leaving group;

each R$^{ALK}$ is independently a linear, branched, or cyclic alkyl (1–20C) group;

each R$^{SUB}$ is independently H, linear, branched, or cyclic alkyl (1–20C), aryl (1–20C), or alkaryl (1–30C);

each R$^{ESTER}$ is independently N-hydroxysuccinimidyl, p-nitrophenoxy, or pentafluorophenoxy;

each R$^B$ is independently a radical comprising 1–50 atoms selected from the group C, H, N, O, Si, P and S;

$n^{[6]}$, if present, is 1 to 32;

$p^{[6]}$, if present, is 1 to 8;

with the proviso that the product $n^{[6]} \times p^{[6]}$ be greater than 1 and less than 33;

$n^{[7]}$, if present, is 1 to 32;

$p^{[7]}$, if present, is 1 to 8;

with the proviso that the product $n^{[7]} \times p^{[7]}$ be greater than 1 and less than 33;

each $Q^{[6]}$ and each $Q^{[7]}$, if present, is independently a radical comprising 1–100 atoms selected from the group C, H, N, O, Si, P and S, and wherein each $Q^{[6]}$ and $Q^{8\ 7]}$ moiety, if present, forms attachment sites for at least $p^{[6]}$ or $p^{[7]/2}$ functional groups, respectively, wherein the attachment sites are alkyl, alkenyl, or aromatic carbon atoms;

and wherein $Q^{[6]}$ and $Q^{[7]}$, if present, optionally further comprises one or more polyethylene oxide groups; and wherein $p^{[7]/2}$ is an integer;

with the proviso that the valency platform molecule comprises at least 2 polyethylene oxide groups each having a molecular weight of greater than about 5,000 Da, and wherein the total of the molecular weights of all polyethylene oxide groups in the valency platform molecule in combination is greater than about 18,000 Da.

92. A composition comprising conjugates comprising biologically active molecules and the valency platform molecules according to claim 59.

93. The composition of claim 92, wherein the biologically active molecules are β₂GPI domain I polypeptides or analogs thereof that specifically bind to β₂GPI-dependent antiphospholipid antibodies.

94. The composition of claim 93, wherein the biologically active molecules are β₂GPI domain I polypeptides.

95. The composition of claim 92, wherein the biologically active molecules are selected from the group consisting of polysaccharides, polypeptides, nucleic acids, and lipids.

96. The composition of claim 92, wherein the biologically active molecules are polypeptides.

97. A conjugate of a valency platform molecule and a biologically active molecule, having the formula:

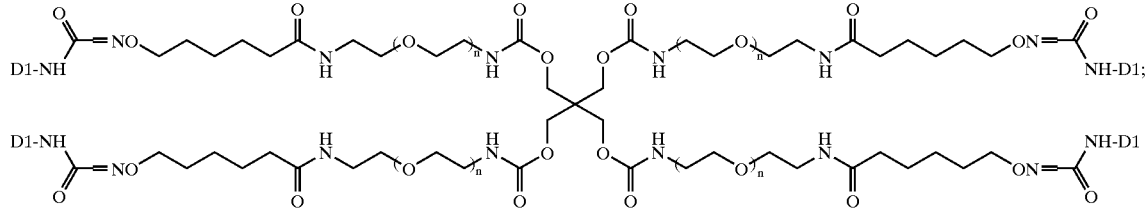

wherein the molecular weight of the polyethylene oxide groups in combination is 26,400–44,000 Da; and wherein D1 in said structures is a polypeptide consisting of amino acids No. 2–63 of SEQ ID NO: 2.

98. A pharmaceutically acceptable composition comprising conjugates comprising biologically active molecules and the valency platform molecules according to any one of claims 80–91 and a pharmaceutically acceptable carrier.

99. The composition of claim 19, wherein the biologically active molecules comprise said nucleic acid.

100. The composition of claim 20, wherein the biologically active molecules are β2GPI domain 1 polypeptides.

101. A pharmaceutically acceptable composition comprising the composition of claim 18 and a pharmaceutically acceptable carrier.

102. A pharmaceutically acceptable composition comprising the composition of claim 19 and a pharmaceutically acceptable carrier.

103. A pharmaceutically acceptable composition comprising the composition of claim 20 and a pharmaceutically acceptable carrier.

104. A pharmaceutically acceptable composition comprising the composition of claim 21 and a pharmaceutically acceptable carrier.

105. A method of making the conjugates according to claim 16 or 92, comprising covalently bonding the biologically active molecules to the valency platform molecules to form conjugates.

106. A method for treating an antibody mediated disease, comprising administering to the individual an effective amount of the composition according to claim 16 or 92.

107. The composition of claim 1, wherein said valency platform molecules have a polydispersity less than 1.07.

108. The composition of claim 9, wherein the valency platform molecules individually comprise at least three carbamate groups and at least three aminooxy groups, wherein the aminooxy groups are protected.

109. The composition of claim 108, wherein the high molecular weight. polyethylene oxide group has a molecular weight greater than about 20,000 Daltons.

110. The composition of claim 108, wherein the high molecular weight polyethylene oxide group has a molecular weight greater than about 22,000 Daltons.

111. The composition of claim 13, wherein the valency platform molecules individually comprise at least three amine reactive conjugating functional groups.

112. The composition of claim 14, wherein the aminooxy groups are protected.

113. The composition of claim 16, wherein the valency platform molecules have a polydispersity less than 1.07.

114. The composition of claim 17, wherein the biologically active molecules are polypeptides.

115. The composition of claim 17, wherein the biologically active molecules are nucleic acids.

116. The composition of claim 52, wherein the valency platform molecules individually comprise at least three carbamate groups, and wherein the valency platform molecules prior to conjugation individually comprise at least 3 aminooxy groups.

117. The composition of claim 116, wherein the biologically active molecules are β2GPI domain 1 polypeptides.

118. The composition of claim 116, wherein the biologically active molecules comprise a nucleic acid which specifically binds to an anti-double stranded DNA antibody.

119. The composition of claim 116, wherein the high molecular weight polyethylene oxide group has a molecular weight of at least about 22,000 Daltons.

120. The composition of claim 119, wherein the biologically active molecules are β2GPl domain 1 polypeptides.

121. The composition of claim 119, wherein the biologically active molecules comprise a nucleic acid which specifically binds to an anti-double stranded DNA antibody.

122. The composition of claim 56, wherein the valency platform molecules prior to conjugation individually comprise at least three amine reactive conjugating functional groups.

123. A composition comprising conjugates according to claim 24, wherein the valency platform molecules have a polydispersity less than 1.2.

124. The conjugate of claim 28, wherein the core group comprises the high molecular weight polyethylene oxide group.

125. The conjugate of claim 28, wherein an arm comprises the high molecular weight polyethylene oxide group.

126. The composition of claim 59, wherein the valency platform molecules individually comprise a core group and at least three arms wherein each arm comprises a terminus.

127. The composition of claim 126, wherein the core group comprises at least one of the first and second polyethylene oxide groups.

128. The composition of claim 126, wherein an arm comprises at least one of the first and second polyethylene oxide groups.

129. The composition of claim 126, wherein at least one of the first and second polyethylene oxide groups is attached to the core or one of said arms.

130. The composition of claim 126, wherein the valency platform molecules individually comprise at least three carbamate groups and at least three aminooxy groups, wherein the aminooxy groups are protected.

131. The composition of claim 130, wherein the total of the molecular weights of all polyethylene oxide groups in each valency platform molecule in combination is greater than about 20,000 Daltons.

132. The composition of claim 130, wherein the total of the molecular weights of all polyethylene oxide groups in each valency platform molecule in combination is greater than about 22,000 Daltons.

133. The composition of claim 130, wherein all polyethylene oxide groups in each valency platform molecule are in the arms.

134. The composition of claim 59, wherein the valency platform molecules individually comprise at least three reactive conjugating groups selected from the group consisting of hydroxyl, thiol, isocyanate, isothiocyanate, amine, alkyl halide, alkylmercurial halide, aldehyde, ketone, carboxylic acid halide, α-halocarbonyl, α,β-unsaturated carbonyl, haloformate ester, carboxylic acid, carboxylic ester, carboxylic anhydride, O-acyl isourea, hydrazide, maleimide, imidate ester, sulfonate ester, sulfonyl halide, α,β-unsaturated sulfone, aminooxy, semicarbazide, and β-aminothiol.

135. The composition of claim 134, wherein the valency platform molecules individually comprise at least three amine reactive conjugating functional groups.

136. The composition of claim 59, wherein the valency platform molecules individually comprise at least 3 aminooxy groups.

137. The composition of claim 136, wherein the aminooxy groups are protected.

138. The composition of claim 59, wherein the valency platform molecules individually comprise at least 3 carbamate groups.

139. The composition of claim 59, wherein the valency platform molecules have a polydispersity less than 1.07.

140. The composition of claim 76, wherein the valency platform molecules individually comprise a core group and four arms, wherein each arm comprises one of said first, second, third, and fourth polyethylene glycol groups.

141. The composition of claim 92, wherein the biologically active molecules are nucleic acids.

142. The composition of claim 92, wherein the biologically active molecules comprise a nucleic acid which specifically binds to an anti-double stranded DNA antibody.

143. A pharmaceutically acceptable composition comprising the composition of claim 142 and a pharmaceutically acceptable carrier.

144. The composition of claim 92, wherein the conjugates are B cell toleragens.

145. A pharmaceutically acceptable composition comprising the composition of claim 144 and a pharmaceutically acceptable carrier.

146. The composition of claim 92, wherein the biologically active molecules are αGal epitopes.

147. The composition of claim 92, wherein the valency platform molecules individually comprise a core group and at least three arms wherein each arm comprises a terminus.

148. The composition of claim 147, wherein the core group comprises at least one of the first and second polyethylene oxide groups.

149. The composition of claim 147, wherein an arm comprises at least one of the polyethylene oxide groups.

150. The composition of claim 147, wherein at least one of the first and second polyethylene oxide groups is attached to the core or one of said arms.

151. The composition of claim 147, wherein the valency platform molecules individually comprise at least three carbamate groups, and wherein the valency platform molecules prior to conjugation individually comprise at least 3 aminooxy groups 152. The composition of claim 151, wherein the biologically active molecules are β2GPI domain 1 polypeptides.

153. The composition of claim 151, wherein the biologically active molecules comprise a nucleic acid which specifically binds to an anti-double stranded DNA antibody.

154. The composition of claim 151, wherein the total of the molecular weights of all polyethylene oxide groups in each valency platform molecule in combination is greater than about 22,000 Daltons.

155. The composition of claim 154, wherein the biologically active molecules are β2GPI domain 1 polypeptides.

156. The composition of claim 154, wherein the biologically active molecules comprise a nucleic acid which specifically binds to an anti-double, stranded DNA antibody.

157. The composition of claim 151, wherein the molecular weight of all polyethylene oxide groups in each valency platform molecule in combination is 26,400-44,000 Da.

158. The composition of claim 157, wherein the biologically active molecules are β2GPI domain 1 polypeptides.

159. The composition of claim 157, wherein the biologically active molecules comprise a nucleic acid which specifically binds to an anti-double stranded DNA antibody.

160. The composition of claim 92, wherein the valency platform molecules prior to conjugation individually comprise at least three reactive conjugating groups selected from the group consisting of hydroxyl, thiol, isocyanate, isothiocyanate, amine, alkyl halide, alkylmercurial halide, aldehyde, ketone, carboxylic acid halide, α-halocarbonyl, α,β-unsaturated carbonyl, haloformate ester, carboxylic acid, carboxylic ester, carboxylic anhydride, O-acyl isourea, hydrazide, maleimide, imidate ester, sulfonate ester, sulfonyl halide, α,β-unsaturated sulfone, aminooxy, semicarbazide, and β-aminothiol.

161. The composition of claim 160, wherein the valency platform molecules prior to conjugation individually comprise at least three amine reactive conjugating functional groups.

162. The composition of claim 92, wherein the valency platform molecules prior to conjugation individually comprise at least 3 aminooxy groups.

163. The composition of claim 92, wherein the valency platform molecules individually comprise at least 3 carbamate groups.

164. The composition of claim 92, wherein the valency platform molecules have a polydispersity less than 1.07.

165. A pharmaceutically acceptable composition comprising the composition of claim 94 and a pharmaceutically acceptable carrier.

166. The composition of claim 94, wherein the conjugates are effective for the treatment of antibody mediated thrombosis.

167. A pharmaceutically acceptable composition comprising the composition of claim 166 and a pharmaceutically acceptable carrier.

168. The composition according to claim 98, wherein the biologically active molecules are polypeptides.

169. The composition according to claim 98, wherein the biologically active molecules are nucleic acids.

170. A method for treating an antibody mediated disease, comprising administering to the individual an effective amount of the composition according to claim 97.

* * * * *

SEQUENCE LISTING

<160> NUMBER OF SEQ ID NOS: 2

<210> SEQ ID NO 1
<211> LENGTH: 192
<212> TYPE: DNA
<213> ORGANISM: Homo Sapien

<400> SEQUENCE: 1

```
ggacggacct gtcccaagcc agatgattta ccattttcca cagtggtccc gttaaaaaca      60
ttctatgagc caggagaaga gattacgtat tcctgcaagc cgggctatgt gtcccgagga     120
gggatgagaa agtttatctg ccctctcaca ggactgtggc ccatcaacac tctgaaatgt     180
acacccagag ta                                                         192
```

<210> SEQ ID NO 2
<211> LENGTH: 64
<212> TYPE: PRT
<213> ORGANISM: Homo Sapien

<400> SEQUENCE: 2

```
Gly Arg Thr Cys Pro Lys Pro Asp Asp Leu Pro Phe Ser Thr Val Val
 1               5                  10                  15

Pro Leu Lys Thr Phe Tyr Glu Pro Gly Glu Glu Ile Thr Tyr Ser Cys
                20                  25                  30

Lys Pro Gly Tyr Val Ser Arg Gly Gly Met Arg Lys Phe Ile Cys Pro
            35                  40                  45

Leu Thr Gly Leu Trp Pro Ile Asn Thr Leu Lys Cys Thr Pro Arg Val
    50                  55                  60
```